(12) United States Patent
Kurasawa et al.

(10) Patent No.: US 9,241,910 B2
(45) Date of Patent: Jan. 26, 2016

(54) ORALLY-DISINTEGRATING SOLID PREPARATION

(75) Inventors: Takashi Kurasawa, Osaka (JP); Yasuko Watanabe, Osaka (JP); Yoshihiro Omachi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/921,731

(22) PCT Filed: Mar. 10, 2009

(86) PCT No.: PCT/JP2009/054983
§ 371 (c)(1),
(2), (4) Date: Sep. 9, 2010

(87) PCT Pub. No.: WO2009/113703
PCT Pub. Date: Sep. 17, 2009

(65) Prior Publication Data
US 2011/0091563 A1    Apr. 21, 2011

(30) Foreign Application Priority Data

Mar. 11, 2008  (JP) ................................ 2008-061673
Dec. 26, 2008  (JP) ................................ 2008-334920

(51) Int. Cl.
| A61K 47/30 | (2006.01) |
| A61K 9/16 | (2006.01) |
| A61K 9/20 | (2006.01) |
| A61K 31/4439 | (2006.01) |
| A61K 47/10 | (2006.01) |
| A61K 47/14 | (2006.01) |
| A61K 47/32 | (2006.01) |
| A61K 47/34 | (2006.01) |
| A61K 47/38 | (2006.01) |
| A61K 9/28 | (2006.01) |
| A61K 9/00 | (2006.01) |
| A61K 9/50 | (2006.01) |

(52) U.S. Cl.
CPC ............. *A61K 9/2886* (2013.01); *A61K 9/0056* (2013.01); *A61K 9/2081* (2013.01); *A61K 9/5026* (2013.01); *A61K 9/5078* (2013.01); *A61K 31/4439* (2013.01)

(58) Field of Classification Search
None
See application file for complete search history.

(56) References Cited

U.S. PATENT DOCUMENTS

| 5,464,632 | A | 11/1995 | Cousin et al. |
| 6,328,994 | B1 | 12/2001 | Shimizu et al. |
| 6,462,058 | B1 | 10/2002 | Fujishima et al. |
| 6,664,276 | B2 | 12/2003 | Fujishima et al. |
| 6,897,205 | B2 | 5/2005 | Beckert et al. |
| 6,939,971 | B2 | 9/2005 | Fujishima et al. |
| 7,339,064 | B2 | 3/2008 | Fujishima et al. |
| 7,438,929 | B2 | 10/2008 | Beckert et al. |
| 7,498,044 | B2 | 3/2009 | Petereit et al. |
| 7,569,697 | B2 | 8/2009 | Fujishima et al. |
| 7,833,546 | B2 | 11/2010 | Petereit et al. |
| 7,932,258 | B2 | 4/2011 | Petereit et al. |
| 2003/0045724 | A1 | 3/2003 | Fujishima et al. |
| 2003/0152627 | A1 | 8/2003 | Beckert et al. |
| 2004/0048898 | A1 | 3/2004 | Fujishima et al. |
| 2004/0219211 | A1 | 11/2004 | Criere et al. |
| 2005/0053660 | A1 | 3/2005 | Beckert et al. |
| 2005/0079216 | A1 | 4/2005 | Petereit et al. |
| 2005/0152977 | A1 | 7/2005 | Petereit et al. |
| 2005/0214372 | A1 | 9/2005 | Di Capua et al. |
| 2005/0228026 | A1 | 10/2005 | Fujishima et al. |
| 2005/0232988 | A1 | 10/2005 | Venkatesh et al. |
| 2005/0287211 | A1 | 12/2005 | Yoshida et al. |
| 2006/0115529 | A1* | 6/2006 | Jeong et al. .................. 424/464 |
| 2007/0141137 | A1 | 6/2007 | Nagahara et al. |
| 2007/0141151 | A1 | 6/2007 | Silver et al. |
| 2007/0202169 | A1 | 8/2007 | Silver et al. |
| 2008/0057123 | A1 | 3/2008 | Grenier et al. |
| 2008/0132547 | A1 | 6/2008 | Fujishima et al. |
| 2008/0193522 | A1 | 8/2008 | Meier et al. |
| 2008/0200482 | A1 | 8/2008 | Petereit et al. |
| 2008/0206324 | A1 | 8/2008 | Gryczke et al. |
| 2008/0206350 | A1* | 8/2008 | Gryczke ....................... 424/501 |
| 2009/0148519 | A1 | 6/2009 | Zaima et al. |

(Continued)

FOREIGN PATENT DOCUMENTS

| EP | 0 237 200 | 9/1987 |
| EP | 1 100 469 | 3/2005 |

(Continued)

OTHER PUBLICATIONS

Khan et al., Journal of Controlled Release, 58: 215-222 (1999).*

(Continued)

*Primary Examiner* — Bethany Barham
*Assistant Examiner* — Lisbeth C Robinson
(74) *Attorney, Agent, or Firm* — Hamre, Schumann, Mueller & Larson, P.C.

(57) ABSTRACT

The present invention provides an orally-disintegrating solid preparation such as a tablet produced by tabletting fine granules showing controlled release of a pharmaceutically active ingredient and an additive, and the like, and the orally-disintegrating solid preparation containing fine granules coated with a coating layer containing a polymer affording a casting film having an elongation at break of about 100-about 700%. With the preparation, breakage of fine granules during tabletting can be suppressed in the production of an orally-disintegrating solid preparation containing fine granules showing controlled release of a pharmaceutically active ingredient.

11 Claims, No Drawings

(56) References Cited

U.S. PATENT DOCUMENTS

| | | |
|---|---|---|
| 2009/0148524 A1 | 6/2009 | Higuchi et al. |
| 2009/0220611 A1 | 9/2009 | Dargelas et al. |
| 2010/0015239 A1 | 1/2010 | Ahmed et al. |
| 2010/0068291 A1 | 3/2010 | Caisse et al. |
| 2010/0151010 A1 | 6/2010 | Petereit et al. |
| 2013/0273157 A1 | 10/2013 | Ishii et al. |
| 2015/0037423 A1 | 2/2015 | Kurasawa et al. |

FOREIGN PATENT DOCUMENTS

| | | |
|---|---|---|
| EP | 1 121 103 | 12/2006 |
| EP | 1 813 275 | 8/2007 |
| EP | 1 837 016 | 9/2007 |
| EP | 2 098 250 | 9/2007 |
| EP | 1 839 650 | 10/2007 |
| EP | 1 967 211 | 9/2008 |
| JP | 62-277322 | 12/1987 |
| JP | 6-502194 | 3/1994 |
| JP | 2000-103731 | 4/2000 |
| JP | 2000-281564 | 10/2000 |
| JP | 2004-292427 | 10/2004 |
| JP | 2004-536855 | 12/2004 |
| JP | 2005-526546 | 9/2005 |
| MX | PA01012642 | 7/2002 |
| WO | 96/01624 | 1/1996 |
| WO | 98/46215 | 10/1998 |
| WO | 99/25323 | 5/1999 |
| WO | 99/59544 | 11/1999 |
| WO | 00/06126 | 2/2000 |
| WO | 00/18374 | 4/2000 |
| WO | 01/37808 | 5/2001 |
| WO | 02/30398 | 4/2002 |
| WO | 02/060415 | 8/2002 |
| WO | 03/072087 | 9/2003 |
| WO | 03/086366 | 10/2003 |
| WO | 2004/035020 | 4/2004 |
| WO | 2004/045580 | 6/2004 |
| WO | 2005/009410 | 2/2005 |
| WO | 2005/030182 | 4/2005 |
| WO | 2005/077342 | 8/2005 |
| WO | 2005/079752 | 9/2005 |
| WO | 2005/084649 | 9/2005 |
| WO | 2006/010394 | 2/2006 |
| WO | 2006/082089 | 8/2006 |
| WO | 2006/105798 | 10/2006 |
| WO | 2006/122925 | 11/2006 |
| WO | 2006/125483 | 11/2006 |
| WO | 2007/006353 | 1/2007 |
| WO | 2007/036671 | 4/2007 |
| WO | 2007/037259 | 4/2007 |
| WO | 2007/074856 | 7/2007 |
| WO | 2007/075980 | 7/2007 |
| WO | 2007/078271 | 7/2007 |
| WO | 2007/086692 | 8/2007 |
| WO | 2007/121537 | 11/2007 |
| WO | 2007/122478 | 11/2007 |
| WO | 2007/129178 | 11/2007 |
| WO | 2007/149801 | 12/2007 |
| WO | 2008/006534 | 1/2008 |
| WO | 2008/014175 | 1/2008 |
| WO | 2008/025535 | 3/2008 |
| WO | 2008/081891 | 7/2008 |
| WO | 2008/101554 | 8/2008 |
| WO | 2008/135090 | 11/2008 |
| WO | 2009/113703 | 9/2009 |

OTHER PUBLICATIONS

Miura, Yakugaku Zusshi, 126: 395-402 (2006).*
Wagner et al., European Journal of Pharmaceutics and Biopharmaceutics, 50: 285-291 (2000).*
http://www.ub.es/legmh/capitols/sunyenegre.pdf—retrieved Jun. 15, 2011.
http://es.wikipedia.org/wiki/Forma_gal%c3%a9nica—retrieved Jun. 15, 2011.
http://intranet.comunidadandina.org/documentos/Gacetas/gace722.pdf—Oct. 2001.
http://intranet.comunidadandina.org/documentos/procesos/21-ip-2000.doc—Oct. 2000.
Authorized officer Sophie Muller, International Search Report issued in Application No. PCT/JP2009/054983, mailed Apr. 20, 2010—3 pages.
Beckert, et al., "Compression of enteric-coated pellets to disintegrating tablets", International Journal of Pharmaceutics, vol. 143, 1996, pp. 13-23.
Degussa. Product Brochures of Eudragit FS30D, 2005—10 pages.
Lehmann, et al., "Fast Disintegrating Controlled Release Tables from Coated Particles", Drugs made in Germany, vol. 37, No. 2, 1994, pp. 53-60.
Reo, et al., "Taste Masking Science and Technology Applied to Compacted Oral Solid Dosage—Part 1", American Pharmaceutical Review, vol. 5, No. 4, 2002, pp. 8-13.
Reo, et al., "Taste Masking Science and Technology Applied to Compacted Oral Solid Dosage Forms—Part", American Pharmaceutical Review, vol. 5, Issue 4, 2002, pp. 8-15.
Shimizu, et al., "Formulation Study for Lansoprazole Fast-disintegrating Tablet. I. Effect of Compression on Dissolution Behavior", Chem. Pharm. Bull., vol. 51, No. 8, 2003, pp. 942-947.
Shimizu, et al., "Formulation Study for Lansoprazole Fast-disintegrating Tablet. III. Design of Rapidly Disintegrating Tablets", Chem. Pharm. Bull., vol. 51, No. 10, 2003, pp. 1121-1127.
Degussa, "EUDRAGIT® NM 30 D: A Poly(meth)acrylate Alternative for Matrix Tablets", News Pharma Polymers, No. 13, issue 2006, pp. 1-4.
Wagner, et al., "Development of disintegrating multiple-unit tablet on a high-speed rotary tablet press", European Journal of Pharmaceutics and Biopharmaceutics, vol. 50, 2000, pp. 285-291.
PTO Form 892 issued in co-pending U.S. Appl. No. 14/519,979, issued Jun. 12, 2015, 1 page.
Lecomte, et al., "pH-Sensitive Polymer Blends Used as Coating Materials to Control Drug Release from Spherical Beads: Elucidation of the Underlying Mass Transport Mechanisms", Pharmaceutical Research, vol. 22, No. 7, Jul. 2005, pp. 1129-1141.
Shimizu, et al., "Formulation Study for Lansoprazole Fast-disintegrating Tablet. II. Effect of Triethyl Citrate on the Quality of the Products", Chemical & Pharmaceutical Bulletin, vol. 51, No. 9, Sep. 2003, pp. 1029-1035.
Schmid, et al., "Enteric Coating of Ibuprofen Crystals Using Modified Methacrylate Copolymers", Drugs made in Germany, vol. 44, No. 1, Jan. 2001, pp. 12-19.
Evonik Industries, "Eudragit FS 30 D", Jul. 31, 2010, pp. 1-3, XP55028678.
Degussa., "Enteric Coating of Mesalazine Pellets with Eudragit FS 30 D", Pharma Polymers, Jan. 2005, pp. 1-2.
Siepmann, et al., "Polymer blends for controlled release coatings", Journal of Controlled Releases 125, 2008, 1-15.

* cited by examiner

ORALLY-DISINTEGRATING SOLID PREPARATION

TECHNICAL FIELD

The present invention relates to an orally-disintegrating solid preparation comprising fine granules coated with a coating layer, which comprises a polymer affording a casting film having an elongation at break of about 100%-about 700%, to control release of a pharmaceutically active ingredient. Moreover, the present invention relates to a method of suppressing breakage of fine granules showing controlled release of a pharmaceutically active ingredient, which are comprised in an orally-disintegrating tablet obtained by tabletting the fine granules and an additive, which method comprises, during production of the tablet, coating the fine granules with a coating layer comprising a polymer affording a casting film having an elongation at break of about 100-about 700%.

BACKGROUND OF THE INVENTION

With an aging population and their changes in life environment, it is desired to develop an orally-disintegrating solid preparation capable of being administered without water, retaining the convenience for use which is a characteristic of a tablet, and being administered on demand easily, anytime and anywhere, without water.

When the pharmaceutically active ingredient has a bitter taste, masking of the bitter taste by coating is preferable for drug compliance. When the pharmaceutically active ingredient is easily decomposed by an acid, it is necessary to coat the ingredient to prevent decomposition by the gastric acid and ensure sufficient delivery to the intestine. To solve these problems, coated tablets, capsules and the like are generally used.

To meet these requirements, tablets containing coated fine granules have conventionally been developed. For example, JP-A-6-502194 (U.S. Pat. No. 5,464,632) discloses a rapidly disintegratable multiparticular tablet comprising a pharmaceutically active ingredient in the form of coated fine particles and the like. In addition, JP-A-2000-281564 and JP-A-2000-103731 disclose orally-disintegrating tablets containing coated fine granules.

During the production of solid preparations such as tablet containing coated fine granules and the like, however, fine granules may be broken during tabletting as evidenced by partial destruction of a coating layer of fine granules and the like, resulting in problems such as a decreased masking effect on the aforementioned bitter taste, acid resistance and the like.

patent document 1: JP-A-6-502194
patent document 2: JP-A-2000-281564
patent document 3: JP-A-2000-103731

DISCLOSURE OF THE INVENTION

Problems to be Solved by the Invention

The present invention aims to provide an orally-disintegrating solid preparation (tablet and the like) containing fine granules showing controlled release of a pharmaceutically active ingredient, which is capable of easy control of the properties such as disintegration property of fine granules, dissolution property of a pharmaceutically active ingredient, and the like, by suppressing breakage of the fine granules during tabletting in the production of the orally-disintegrating solid preparation.

Means of Solving the Problems

The present inventors have found that, in an orally-disintegrating solid preparation such as tablet and the like, which is produced by tabletting fine granules showing controlled release of a pharmaceutically active ingredient and an additive, breakage of the fine granules during the tabletting can be reduced by coating the fine granules with a coating layer containing a polymer affording a casting film having an elongation at break of about 100%-about 700%, which resulted in the completion of the present invention.

Accordingly, the present invention provides the following.
[1] An orally-disintegrating solid preparation comprising fine granules showing controlled release of a pharmaceutically active ingredient, which has a coating layer comprising a polymer affording a casting film having an elongation at break of about 100%-about 700%.
[2] The preparation of [1] further comprising a plasticizer, wherein the polymer is an enteric polymer.
[3] The preparation of [1], wherein the fine granules are obtained by coating fine granules comprising the pharmaceutically active ingredient with a coating layer comprising a polymer affording a casting film having an elongation at break of about 100-about 700%.
[4] The preparation of [3], wherein the fine granules comprising the pharmaceutically active ingredient are enteric fine granules.
[5] The preparation of [1], wherein the polymer is an enteric polymer.
[6] The preparation of any one of [3] to [5], wherein the polymer is coated in an amount of about 5-about 80 wt % of the fine granules comprising the pharmaceutically active ingredient.
[7] The preparation of [1], wherein the fine granules has an average particle size of about 500 μm or below.
[8] The preparation of [1], wherein the coating layer is formed on the outermost layer of the fine granules.
[9] The preparation of [1], further comprising a coating layer comprising a water-soluble sugar alcohol on the outermost layer of the fine granules.
[10] The preparation of [2], wherein the content of the plasticizer is about 1-about 20 wt % of the weight of the solid content of the polymer.
[11] The preparation of [2], wherein the plasticizer is triethyl citrate.
[12] The preparation of [4], wherein the enteric fine granules comprising the pharmaceutically active ingredient are pH-dependent controlled release fine granules.
[13] The preparation of [12], wherein the pH-dependent controlled release fine granules are obtained by coating core granules comprising the pharmaceutically active ingredient with a controlled release film.
[14] The preparation of [13], wherein the controlled release film comprises a polymer substance that dissolves at not less than pH 6.0 and not more than pH 7.5.
[15] The preparation of [13], wherein the core granules further comprise a basic inorganic salt.
[16] The preparation of [13] or [14], wherein the controlled release film is formed via an intermediate coating layer formed on the core granules.
[17] The preparation of [14], wherein the polymer substance comprises a mixture of one or more kinds selected from the group consisting of hypromellose phthalate, cellulose acetate phthalate, carboxymethyl ethyl cellulose, methyl methacrylate-methacrylic acid copolymer, methacrylic acid-ethyl acrylate copolymer, methacrylic acid-methyl acrylate-methyl methacrylate copolymer, hydroxypropyl methylcellulose acetate succinate, polyvinyl acetate phthalate and shellac.
[18] The preparation of [16], wherein the controlled release film has a polymer substance content of about 30-about 100 wt % of the fine granules.
[19] The preparation of [16], wherein the controlled release film has a polymer substance content of about 50-about 100 wt % of the fine granules.
[20] The preparation of [1], wherein the pharmaceutically active ingredient is unstable to acid.
[21] The preparation of [20], wherein the pharmaceutically active ingredient unstable to acid is a proton pump inhibitor (PPI).
[22] The preparation of [21], wherein the PPI is lansoprazole or an optically active form thereof or a salt thereof.
[23] An orally-disintegrating solid preparation comprising (1) fine granules A showing controlled release of a pharmaceutically active ingredient and (2) fine granules B with a different release rate of a pharmaceutically active ingredient from that of the fine granules of (1), which has a coating layer comprising a polymer affording a casting film having an elongation at break of about 100%-about 700%.
[24] The preparation of [23], wherein the pharmaceutically active ingredient of the fine granules A and that of the fine granules B are the same.
[25] The preparation of [23], wherein the fine granules B have an average particle size of about 500 μm or below.
[26] The preparation of [23], wherein the fine granules B are enteric fine granules that dissolve at not less than pH 5.0 and not more than pH 6.0.
[27] The preparation of [23], wherein the fine granules B are coated with a coating layer comprising an enteric polymer that dissolves at not less than pH 5.0 and not more than pH 6.0.
[28] The preparation of [26], wherein the enteric fine granules comprise one or more kinds of aqueous enteric polymer bases selected from hypromellose phthalate, cellulose acetate phthalate, hydroxypropyl methylcellulose acetate succinate, methacrylic acid-ethyl acrylate copolymer, methacrylic acid-methyl acrylate-methyl methacrylate copolymer, carboxymethyl ethyl cellulose and shellac.
[29] The preparation of [24], wherein the fine granules B are pH-dependent controlled release fine granules obtained by coating core granules comprising the pharmaceutically active ingredient with a controlled release film comprising a polymer substance that dissolves at not less than pH 6.0 and not more than pH 7.5, wherein the controlled release film is formed via an intermediate coating layer formed on the core granules, and the controlled release film has a polymer substance content of about 10-about 70 wt % of the fine granules.
[30] The preparation of [24], wherein the fine granules A and the fine granules B comprise the pharmaceutically active ingredient at a weight ratio of 1:10-10:1.
[31] The preparation of [23], further comprising an additive.
[32] The preparation of [31], wherein the additive comprises a water-soluble sugar alcohol.
[33] The preparation of [31], wherein the additive comprises a disintegrant.
[34] The preparation of [31], wherein the fine granules A is comprised at 10-50 wt %, the fine granules B is comprised at 10-30 wt %, and the additive is comprised at 20-80 wt %, each relative to the whole preparation.
[35] The preparation of [1] or [23], wherein the total weight of the preparation is about 1000 mg or below.
[36] The preparation of [1] or [23], wherein the oral disintegration time is about 90 seconds or less.
[37] The preparation of [23], which is capable of achieving an average pH in the stomach of not less than 4 at 0.5 hr after oral administration and maintaining said pH or higher pH for 14 hours or longer.
[38] The preparation of [23], wherein the pharmaceutically active ingredient is R-lansoprazole or a salt thereof, which reaches the maximum blood drug concentration in about 5 hr and maintains the maximum blood drug concentration of not less than 100 ng/mL for about 4 hr or longer, when 30 mg of the pharmaceutically active ingredient is administered orally.
[39] A method of suppressing breakage of fine granules showing controlled release of a pharmaceutically active ingredient, which are comprised in an orally-disintegrating tablet obtained by tabletting the fine granules and an additive, which method comprises, during production of the tablet, coating the fine granules with a coating layer comprising a polymer affording a casting film having an elongation at break of about 100-about 700%.

Effect of the Invention

The orally-disintegrating solid preparation of the present invention shows reduced breakage of fine granules during tabletting. Therefore, with the orally-disintegrating solid preparation comprising fine granules comprising a pharmaceutically active ingredient, particularly, a pharmaceutically active ingredient unstable to acid, the release of the pharmaceutically active ingredient in the presence of acid, for example, in the stomach, can be controlled to achieve a desired elution profile. In addition, variation of elution profiles for preparations or lots (elution variation) can also be improved.

Since the orally-disintegrating solid preparation of the present invention shows suppressed breakage of fine granules, it can control release of the pharmaceutically active ingredient as desired for a long time. Consequently, a treatment effective concentration can be maintained for a prolonged time, administration frequency can be reduced, and an effective treatment with a small dose can be realized. Moreover, effects such as reduction of side effects caused by slow rise of blood concentration and the like can be achieved.

Since the orally-disintegrating solid preparation of the present invention shows superior disintegration property or dissolution property in the oral cavity, it is used for the treatment or prophylaxis of various diseases as a preparation conveniently taken by elderly persons and children even without water. In addition, since the fine granules comprising the pharmaceutically active ingredient having a size preventing dusty texture are blended, the preparation is smooth in the mouth.

DETAILED DESCRIPTION OF THE INVENTION

The present invention relates to an orally-disintegrating solid preparation comprising fine granules coated with a coating layer, which comprises a polymer affording a casting film having an elongation at break of about 100%-about 700%, to control release of a pharmaceutically active ingredient (hereinafter to be also referred to as the preparation of the present invention).

The polymer to be used in the present invention is a polymer affording a casting film having an elongation at break of about 100-about 700%.

When the elongation at break is less than about 100%, the effect of suppressing the breakage of fine granules during tabletting becomes insufficient, and when it exceeds about 700%, problems of easy clogging of spray nozzle, easy coagulation of fine granules and the like occur in the step of applying the coating layer comprising the polymer.

The elongation at break is measured according to JIS-K7127. That is, a test piece (width 10 mm, length 150 mm, thickness 1 mm) is stretched (rate 200 mm/min) in a tensile tester, the length at which the test piece has been broken is determined, and the elongation at break is calculated by the following formula:

elongation at break (%)=$(L-L0)/L0\times 100$

L0: test piece length before test, L: test piece length at breakage.

In a tensile test of a polymer, the elongation of a casting film is partly recovered as an elastic strain after breakage, after which it remains in the material as a permanent strain or residual strain. The elongation at break is obtained by stretching a polymer film by applying a load until the film is finally broken yielding to the load, and expressing the length of elongation as a residual strain in a numerical value, where the unit is %. For example, when a load is applied to a 100 cm film and the film is broken at 130 cm, the elongation at break of the film is 30%.

Examples of the polymer affording a casting film having an elongation at break of about 100-about 700% in the present invention include hypromellose phthalate, cellulose acetate phthalate, carboxymethyl ethyl cellulose, methyl methacrylate-methacrylic acid copolymer, methacrylic acid-ethyl acrylate copolymer, methacrylic acid-methyl acrylate-methyl methacrylate copolymer, ethyl acrylate-methyl methacrylate-trimethylammonioethyl methacrylate chloride copolymer, butyl methacrylate-2-dimethylaminoethyl methacrylate-methyl methacrylate copolymer, ethyl acrylate-methyl methacrylate copolymer, hydroxypropyl methylcellulose acetate succinate, polyvinyl acetate phthalate, shellac and the like. More specific examples thereof include commercially available products such as Eudragit FS30D (methacrylic acid-methyl acrylate-methyl methacrylate copolymer: elongation at break: 300% (when comprising 10 wt % triethyl citrate)), Eudragit RS100 (ethyl acrylate-methyl methacrylate-trimethylammonioethyl methacrylate chloride copolymer, aminoalkylmethacrylate copolymer RS: elongation at break: 250% (when comprising 20 wt % triethyl citrate)), Eudragit E100 (methyl methacrylate-butyl methacrylate-dimethylaminoethyl methacrylate copolymer, aminoalkylmethacrylate copolymer E: elongation at break: 200%), Eudragit NE30D (methyl methacrylate-ethyl acrylate copolymer: elongation at break: 600%) and the like.

Among those mentioned above, an enteric polymer is preferable, and a methacrylic acid-methyl acrylate-methyl methacrylate copolymer is particularly preferable.

The aforementioned polymer may be a combination of two or more kinds (preferably 2-3 kinds).

When plural kinds of polymers are mixed for use in the present invention, the elongation at break means that of a mixed polymer.

The layer comprising a polymer may contain a plasticizer. Examples of the plasticizer include triethyl citrate, polyethylene glycol, diethyl phthalate, triacetine, glycerol, glycerol fatty acid ester, sesame oil, castor oil and the like.

The content of the plasticizer in the aforementioned film layer comprising a polymer is about 1-about 20 wt %, preferably about 3-about 15 wt %, more preferably about 5-about 12 wt %, relative to the weight of the solid content of the polymer.

When a plasticizer is added to a polymer in the present invention, the elongation at break means that of a polymer containing a plasticizer.

An active pharmaceutical active ingredient used in the present invention may be in any form of a solid, a powder, a crystal, oil, a solution and the like. The efficacy thereof is not particularly limited. Examples of the active pharmaceutical active ingredient include a tonic, an antipyretic analgesic antiphlogistic, a psychotropic agent, an antianxiety agent, an antidepressant, a hypnotic sedative, an anticonvulsant, a central nervous system drug, a brain metabolism improving agent, a brain circulation improving agent, an antiepileptic agent, a sympathomimetic stimulant, a gastrointestinal agent, an antacid, an antiulcer agent, an antitussive expectorant, an antiemetic, a respiratory accelerator, a bronchodilator, an antiallergy agent, a dental agent for oral use, an antihistamine, an inotropic agent, an agent for arrhythmia, a diuretic, a blood pressure lowering agent, a vasoconstrictor, a coronary vasodilator, a peripheral vasodilator, an agent for hyperlipemia, a cholagogue, an antibiotic, a chemotherapeutic agent, an agent for diabetes, an agent for osteoporosis, an antirheumatic, a skeletal muscle relaxant, a hormone agent, an alkaloidal narcotic, a sulfa drug, a gout remedy, a blood coagulation inhibitor, an anti-malignant tumor agent, an Alzheimer's disease remedy and the like, and one or more selected from the aforementioned ingredients are used.

Examples of the tonic include vitamins such as vitamin A, vitamin D, vitamin E (d-α-tocopherol acetate, etc.), vitamin B1 (dibenzoylthiamine, fursultiamine hydrochloride, etc.), vitamin B2 (riboflavin butyrate, etc.), vitamin B6 (pyridoxine hydrochloride, etc.), vitamin C (ascorbic acid, sodium L-ascorbate, etc.), and vitamin B12 (hydroxocobalamin acetate, cyanocobalamin, etc.), minerals such as calcium, magnesium and iron, proteins, amino acids, oligosaccharides, galenicals, and the like.

Examples of the antipyretic analgesic antiphlogistic include aspirin, acetaminophen, ethenzamide, ibuprofen, diphenhydramine hydrochloride, dl-chlorphenylamine maleate, dihydrocodeine phosphate, noscapine, methylephedrine hydrochloride, phenylpropanolamine hydrochloride, caffeine, caffeine anhydride, serrapeptase, lysozyme chloride, tolfenamic acid, mefenamic acid, diclofenac sodium, flufenamic acid, salicylamide, aminopyrine, ketoprofen, indometacin, bucolome, pentazocine, and the like.

Examples of the psychotropic agent include chlorpromazine, reserpine, and the like.

Examples of the antianxiety agent include alprazolam, chlordiazepoxide, diazepam, and the like.

Examples of the antidepressant include imipramine, maprotiline hydrochloride, amphetamine, and the like.

Examples of the hypnotic sedative include estazolam, nitrazepam, diazepam, perlapine, phenobarbital sodium, and the like.

Examples of the anticonvulsant include scopolamine hydrobromide, diphenhydramine hydrochloride, papaverine hydrochloride, meclizine hydrochloride, dimenthydrinate and the like.

Examples of the central nervous system drug include citicoline, and the like.

Examples of the brain metabolism improving agent include meclofenoxate hydrochloride, and the like.

Examples of the brain circulation improving agent include vinpocetine, and the like.

Examples of the antiepileptic include phenyloin, carbamazepine, and the like.

Examples of the sympathomimetic stimulant include isoproterenol hydrochloride, and the like.

Examples of the gastrointestinal agent include stomachic digestive agents such as diastase, sugar-comprising pepsine, scopolia extract, cellulase AP3, lipase AP, and cinnamic oil, and agents for controlling intestinal function such as berberine chloride, resistant lactobacillus, bifidobacteria, and the like.

Examples of the antacid include magnesium carbonate, sodium hydrogen carbonate, magnesium aluminate metasilicate, synthetic hydrotalcite, precipitated calcium carbonate, magnesium oxide, and the like.

Examples of the antiulcer agent include lansoprazole, omeprazole, rabeprazole, pantoprazole, ilaprazole, tenatoprazole, famotidine, cimetidine, ranitidine hydrochloride, and the like.

Examples of the antitussive expectorant include cloperastine hydrochloride, dextromethorphan hydrobromide, theophylline, potassium guaiacolsulfonate, guaifenesin, codeine phosphate, and the like.

Examples of the antiemetic include difenidol hydrochloride, metoclopramide, and the like.

Examples of the respiratory accelerator include levallorphan tartrate, and the like.

Examples of the bronchodilator include theophylline, salbutamol sulfate, and the like.

Examples of the antiallergy agent include amlexanox, seratrodust, and the like.

Examples of the dental agent for oral use include oxytetracycline, triamcinolone acetonide, chlorhexidine hydrochloride, lidocaine, and the like.

Examples of the antihistamine include diphenhydramine hydrochloride, promethazine, isothipendyl hydrochloride, dl-chlorphenylamine maleate, and the like.

Examples of the inotropic agent include caffeine, digoxin, and the like.

Examples of the agent for arrhythmia include procainamide hydrochloride, propranolol hydrochloride, pindolol, and the like.

Examples of the diuretic include isosorbide, furosemide, a thiazide agent such as HCTZ, and the like.

Examples of the blood pressure lowering agent include delapril hydrochloride, captopril, hexamethonium bromide, hydralazine hydrochloride, labetalol hydrochloride, manidipine hydrochloride, candesartan cilexetil, methyldopa, losartan, valsartan, eposartan, irbesartan, tasosartan, telmisartan, and the like.

Examples of the vasoconstrictor include phenylephrine hydrochloride, and the like.

Examples of the coronary vasodilator include carbochromen hydrochloride, molsidomine, verapamil hydrochloride, and the like.

Examples of the peripheral vasodilator include cinnarizine, and the like.

Examples of the agent for hyperlipemia include cerivastatin sodium, simvastatin, pravastatin sodium, and the like.

Examples of the cholagogue include dehydrocholic acid, trepibutone, and the like.

Examples of the antibiotic include cephem antibiotics such as cephalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefmenoxime hydrochloride, and cefsulodin sodium, synthetic antibacterial agents such as ampicillin, ciclacillin, sulbenicillin sodium, nalidixic acid, and enoxacin, monobactam antibiotics such as carumonam sodium, penem antibiotics, carbapenem antibiotics, and the like.

Examples of the chemotherapeutic agent include sulfamethizole, sulfamethizole hydrochloride, thiazosulfone, and the like.

Examples of the agent for diabetes include tolbutamide, pioglitazone hydrochloride, voglibose, glibenclamide, troglitazone, rosiglitazone maleate, acarbose, miglitol, emiglitate, and the like.

Examples of the agent for osteoporosis include ipriflavone, and the like.

Examples of the skeletal muscle relaxant include methocarbamol, and the like.

Examples of the anti-rheumatic drug include methotrexate, bucillamine and the like.

Examples of the hormone agent include liothyronine sodium, dexamethasone sodium phosphate, predonisolone, oxendolone, leuprorelin acetate, and the like.

Examples of the alkaloidal narcotic include opium, morphine hydrochloride, ipecac, oxycodone hydrochloride, opium alkaloid hydrochloride, cocaine hydrochloride, and the like.

Examples of the sulfa drug include sulfamine, sulfisomidine, sulfamethizole, and the like.

Examples of the gout remedy include allopurinol, colchicine, and the like.

Examples of the blood coagulation inhibitor include dicoumarol, and the like.

Examples of the anti-malignant tumor agent include 5-fluorouracil, uracil, mitomycin, and the like.

Examples of the Alzheimer's disease remedy include idebenone, vinpocetine, and the like.

Among the aforementioned active pharmaceutical ingredients, an antiulcer agent is preferably used.

A pharmaceutically active ingredient that can particularly enjoy the effect of the present invention is a pharmaceutical active ingredient unstable to acid.

Examples of the "pharmaceutical active ingredient unstable to acid" include compounds which are labile in an acidic region and/or inactivated by an acid, and specific examples thereof include vitamin compounds (vitamin B12, fursultiamine, folic acid, vitamin A, vitamin D, etc.), proton pump inhibitor (PPI) and the like. It is particularly preferably PPI, and a benzimidazole compound represented by the formula (I) and having a known antiulcer activity, an optically active form thereof and a salt thereof and the like can be mentioned.

A compound represented by the formula (I)

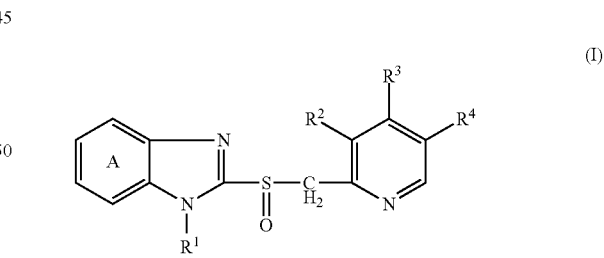

wherein
ring A is a benzene ring or a pyridine ring, each of which optionally has substituent(s),
$R^1$ is a hydrogen atom, an aralkyl group optionally having substituent(s), an acyl group or an acyloxy group, and
$R^2$, $R^3$ and $R^4$ are the same or different and each is a hydrogen atom, an alkyl group optionally having substituent(s), an alkoxy group optionally having substituent(s) or an amino group optionally having substituent(s),
or an optically active form thereof or a salt thereof.

The compound is preferably a compound wherein, in the formula (I), ring A is a benzene ring or a pyridine ring, each of which optionally has substituent(s) selected from a halogen atom, an optionally halogenated $C_{1-4}$ alkyl group, an optionally halogenated $C_{1-4}$ alkoxy group and a 5- or 6-membered heterocyclic group, $R^1$ is a hydrogen atom, $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^3$ is a hydrogen atom, a $C_{1-6}$ alkoxy-$C_{1-6}$ alkoxy group or an optionally halogenated $C_{1-6}$ alkoxy group, and $R^4$ is a hydrogen atom or a $C_{1-6}$ alkyl group.

In the above-mentioned compound represented by the formula (I), examples of the "substituent" of the "benzene ring or pyridine ring, each of which optionally has substituent(s)" for ring A include a halogen atom, a cyano group, a nitro group, an alkyl group optionally having substituent(s), a hydroxy group, an alkoxy group optionally having substituent(s), an aryl group, an aryloxy group, a carboxy group, an acyl group, an acyloxy group, a 5- to 10-membered heterocyclic group and the like. The benzene ring or pyridine ring optionally has 1 to 3 of these substituents. When the number of the substituents is not less than 2, respective substituents may be the same or different. Of these substituents, a halogen atom, an alkyl group optionally having substituent(s), an alkoxy group optionally having substituent(s) and the like are preferable.

Examples of the halogen atom include fluorine, chlorine, bromine atom and the like. Of these, fluorine is preferable.

Examples of the "alkyl group" of the "alkyl group optionally having substituent(s)" include a $C_{1-7}$ alkyl group (e.g., a methyl, ethyl, propyl, isopropyl, butyl, isobutyl, sec-butyl, tert-butyl, pentyl, hexyl, heptyl group etc.). Examples of the "substituent" of the "alkyl group optionally having substituent(s)" include a halogen atom, a hydroxy group, a $C_{1-6}$ alkoxy group (e.g., methoxy, ethoxy, propoxy, butoxy etc.), a $C_{1-6}$ alkoxy-carbonyl group (e.g., a methoxycarbonyl, ethoxycarbonyl, propoxycarbonyl group etc.), a carbamoyl group and the like. The number of the substituents may be 1 to 3. When the number of the substituents is not less than 2, respective substituents may be the same or different.

Examples of the "alkoxy group" of the "alkoxy group optionally having substituent(s)" include a $C_{1-6}$ alkoxy group (e.g., methoxy, ethoxy, propoxy, isopropoxy, butoxy, isobutoxy, pentoxy etc.) and the like. Examples of the "substituent" of the "alkoxy group optionally having substituent(s)" include those similar to the "substituent" of the above-mentioned "alkyl group optionally having substituent(s)". The number of the substituents is the same as in the above-mentioned "alkyl group optionally having substituent(s)".

Examples of the "aryl group" include a $C_{6-14}$ aryl group (e.g., a phenyl, 1-naphthyl, 2-naphthyl, biphenyl, 2-anthryl group etc.) and the like.

Examples of the "aryloxy group" include a $C_{6-14}$ aryloxy group (e.g., a phenyloxy, 1-naphthyloxy, 2-naphthyloxy group etc.) and the like.

Examples of the "acyl group" include a formyl, alkylcarbonyl, alkoxycarbonyl, carbamoyl, alkylcarbamoyl, alkylsulfinyl, alkylsulfonyl group and the like.

Examples of the "alkylcarbonyl group" include a $C_{1-6}$ alkyl-carbonyl group (e.g., an acetyl, propionyl group etc.) and the like.

Examples of the "alkoxycarbonyl group" include a $C_{1-6}$ alkoxy-carbonyl group (e.g., a methoxycarbonyl, ethoxycarbonyl, propoxycarbonyl, butoxycarbonyl group etc.) and the like.

Examples of the "alkylcarbamoyl group" include an N—$C_{1-6}$ alkyl-carbamoyl group (e.g., a methylcarbamoyl, ethylcarbamoyl group etc.), an N,N-di-$C_{1-6}$ alkyl-carbamoyl group (e.g., a N,N-dimethylcarbamoyl, N,N-diethylcarbamoyl group etc.) and the like.

Examples of the "alkylsulfinyl group" include a $C_{1-7}$ alkylsulfinyl group (e.g., a methylsulfinyl, ethylsulfinyl, propylsulfinyl, isopropylsulfinyl group etc.) and the like.

Examples of the "alkylsulfonyl group" include a $C_{1-7}$ alkylsulfonyl group (e.g., a methylsulfonyl, ethylsulfonyl, propylsulfonyl, isopropylsulfonyl group etc.) and the like.

Examples of the "acyloxy group" include an alkylcarbonyloxy group, an alkoxycarbonyloxy group, a carbamoyloxy group, an alkylcarbamoyloxy group, an alkylsulfinyloxy group, an alkylsulfonyloxy group and the like.

Examples of the "alkylcarbonyloxy group" include a $C_{1-6}$ alkyl-carbonyloxy group (e.g., an acetyloxy, propionyloxy group etc.) and the like.

Examples of the "alkoxycarbonyloxy group" include a $C_{1-6}$ alkoxy-carbonyloxy group (e.g., a methoxycarbonyloxy, ethoxycarbonyloxy, propoxycarbonyloxy, butoxycarbonyloxy group etc.) and the like.

Examples of the "alkylcarbamoyloxy group" include a $C_{1-6}$ alkyl-carbamoyloxy group (e.g., a methylcarbamoyloxy, ethylcarbamoyloxy group etc.) and the like.

Examples of the "alkylsulfinyloxy group" include a $C_{1-7}$ alkylsulfinyloxy group (e.g., methylsulfinyloxy, ethylsulfinyloxy, propylsulfinyloxy, isopropylsulfinyloxy group etc.) and the like.

Examples of the "alkylsulfonyloxy group" include a $C_{1-7}$ alkylsulfonyloxy group (e.g., methylsulfonyloxy, ethylsulfonyloxy, propylsulfonyloxy, isopropylsulfonyloxy group etc.) and the like.

Examples of the "5- to 10-membered heterocyclic group" include a 5- to 10-membered (preferably 5- or 6-membered) heterocyclic group containing, besides carbon atoms, one or more to 4 (e.g., 1 to 3) heteroatoms selected from a nitrogen atom, a sulfur atom and an oxygen atom. Specific examples include a 2- or 3-thienyl group, a 2-, 3- or 4-pyridyl group, a 2- or 3-furyl group, a 1-, 2- or 3-pyrrolyl group, a 2-, 3-, 4-, 5- or 8-quinolyl group, a 1-, 3-, 4- or 5-isoquinolyl group, a 1-, 2- or 3-indolyl group and the like. Of these, a 5- or 6-membered heterocyclic group such as a 1-, 2- or 3-pyrrolyl group is preferable.

Ring A is preferably a benzene ring or a pyridine ring, each of which optionally has 1 or 2 substituents selected from a halogen atom, an optionally halogenated $C_{1-4}$ alkyl group, an optionally halogenated $C_{1-4}$ alkoxy group and 5- or 6-membered heterocyclic group.

Examples of the "aralkyl group" of the "aralkyl group optionally having substituent(s)" for $R^1$ include a $C_{7-16}$ aralkyl group (e.g., a $C_{6-10}$ aryl-$C_{1-6}$ alkyl group such as benzyl, phenethyl etc.) and the like. Examples of the "substituent" of the "aralkyl group optionally having substituent(s)" include those similar to the "substituent" of the above-mentioned "alkyl group optionally having substituent(s)". The number of the substituents is 1 to 4. When the number of the substituents is not less than 2, respective substituents may be the same or different.

Examples of the "acyl group" for $R^1$ include those similar to the "acyl group" exemplified as the substituent of the above-mentioned ring A.

Examples of the "acyloxy group" for $R^1$ include those similar to the "acyloxy group" exemplified as the substituent of the above-mentioned ring A.

$R^1$ is preferably a hydrogen atom.

Examples of the "alkyl group optionally having substituent(s)" for $R^2$, $R^3$ or $R^4$ include those similar to the "alkyl group optionally having substituent(s)" exemplified as the substituent of the above-mentioned ring A.

Examples of the "alkoxy group optionally having substituent(s)" for $R^2$, $R^3$ or $R^4$ include those similar to the "alkoxy group optionally having substituent(s)" exemplified as the substituent of the above-mentioned ring A.

Examples of the "amino group optionally having substituent(s)" for $R^2$, $R^3$ or $R^4$ include an amino group, a mono-$C_{1-6}$ alkylamino group (e.g., methylamino, ethylamino etc.), a mono-$C_{6-14}$ arylamino group (e.g., phenylamino, 1-naphthylamino, 2-naphthylamino etc.), a di-$C_{1-6}$ alkylamino group (e.g., dimethylamino, diethylamino etc.), a di-$C_{6-14}$ arylamino group (e.g., diphenylamino etc.) and the like.

$R^2$ is preferably a $C_{1-6}$ alkyl group, a $C_{1-6}$ alkoxy group, a $C_{1-6}$ alkoxy-$C_{1-6}$ alkoxy group or a di-$C_{1-6}$ alkylamino group. $R^2$ is more preferably a $C_{1-3}$ alkyl group or a $C_{1-3}$ alkoxy group.

$R^3$ is preferably a hydrogen atom, a $C_{1-6}$ alkoxy-$C_{1-6}$ alkoxy group or an optionally halogenated $C_{1-6}$ alkoxy group. $R^3$ is more preferably a $C_{1-3}$ alkoxy group which is halogenated or optionally substituted by a $C_{1-3}$ alkoxy group.

$R^4$ is preferably a hydrogen atom or a $C_{1-6}$ alkyl group. $R^4$ is more preferably a hydrogen atom or a $C_{1-3}$ alkyl group (it is particularly preferably a hydrogen atom).

Specific examples of the compound represented by the formula (I) include
2-[[[3-methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole, 2-[(RS)-[(4-methoxy-3-methylpyridin-2-yl)methyl]sulfinyl]-5-(1H-pyrrol-1-yl)-1H-benzimidazole and the like.

In the present invention, more specifically, benzimidazole compounds such as lansoprazole, omeprazole, S-omeprazole, Pantoprazole, rabeprazole, tenatoprazole, ilaprazole and the like and imidazopyridine compounds are preferably used as the compound represented by the formula (I) which is PPI.

Of these compounds, lansoprazole, i.e., 2-[[[3-methyl-4-(2,2,2-trifluoroethoxy)-2-pyridinyl]methyl]sulfinyl]-1H-benzimidazole is particularly preferable.

The aforementioned compound (I) may be a racemate or an optically active form such as R-form, S-form. For example, it may be an optically active form of lansoprazole, i.e. a R-form or S-form of lansoprazole, and the like. It is particularly preferable an optically active form such as (R)-2-[[[3-methyl-4-(2,2,2-trifluoroethoxy)-2-pyridinyl]methyl]sulfinyl]-1H-benzimidazole and the like.

In the present invention, PPI may be a pharmaceutically acceptable salt of the compound represented by the formula (I) or an optically active form thereof. The salt is preferably a pharmaceutically acceptable salt. Examples thereof include salts with inorganic base, salts with organic base, salts with basic amino acid, and the like.

Preferable examples of the salt with inorganic base include alkali metal salts such as sodium salt, potassium salt and the like; alkaline earth metal salts such as calcium salt, magnesium salt and the like; ammonium salt and the like.

Preferable examples of the salt with organic base include salts with alkylamines (trimethylamine, triethylamine etc.), heterocyclic amines (pyridine, picoline etc.), alkanol amines (ethanolamine, diethanolamine, triethanolamine etc.), dicyclohexylamine, N,N'-dibenzylethylenediamine and the like.

Preferable examples of the salt with basic amino acid include salts with arginine, lysine, ornithine and the like.

Of these salts, alkali metal salts and alkaline earth metal salts are preferable. Sodium salt is particularly preferable.

The compound represented by the formula (I) can be produced according to a method known per se, for example, the method described in JP-A-61-50978, U.S. Pat. No. 4,628,098, JP-A-10-195068, WO 98/21201 or the like or a method analogous thereto. In addition, the optically active compound represented by the formula (I) can be produced according to a method such as optical resolution (fractional recrystallization, chiral column method, diastereomer method, a method using microorganism or enzyme, and the like), asymmetric oxidation and the like. For example, R form lansoprazole can also be produced according to the method described in WO 00/78745, WO 01/83473, WO 01/87874 and WO 02/44167 or the like.

The aforementioned pharmaceutically active ingredient contained in the solid preparation of the present invention may be of one kind, or two or more kinds (preferably 2-3 kinds).

The pharmaceutically active ingredient may be diluted with a diluent and the like generally used in the fields of medicine, food and the like. In addition, the pharmaceutically active ingredient to be used may be treated for masking of a bitter taste.

The total amount of the aforementioned pharmaceutically active ingredient is, for example, about 0.01-about 50 parts by weight, preferably about 0.05-about 30 parts by weight, per 100 parts by weight of the preparation of the present invention.

In the present invention, the "fine granules" is as defined in the Japanese Pharmacopoeia, the 15th edition (a powder wherein 10% or less of the total amount of the powder passes a 75 μm sieve). The average particle size of the fine granules (fine granules showing controlled release of a pharmaceutically active ingredient) in the preparation of the present invention desirably has an average particle size of about 500 μm or below, preferably about 400 μm or below, in order to prevent rough or powdery texture during administration of the preparation of the present invention. For example, it is about 100-about 500 μm, preferably about 100-about 400 μm.

Unless otherwise specified, the "average particle size" means a volume median diameter (median diameter: a particle diameter corresponding to 50% of cumulative distribution). Examples include a laser diffraction particle size distribution measuring method, specifically, a method using a laser diffraction particle size distribution analyzer HEROS RODOS (manufactured by Sympatec, Germany).

In the present invention, "controlled release of a pharmaceutically active ingredient" means control of a release rate of a pharmaceutically active ingredient such that not more than 80% of the pharmaceutically active ingredient contained in the preparation is released within 1 hour and not less than 80% of the pharmaceutically active ingredient contained in the preparation is released in 2 to 6 hours, in a dissolution test according to the Japanese Pharmacopoeia Dissolution Test Method 2 and using 50 mM phosphate buffer (pH 7.0) free of a surfactant as a test solution.

One embodiment of the "fine granules" in the preparation of the present invention is fine granules showing controlled release of a pharmaceutically active ingredient (hereinafter sometimes to be referred to as controlled release fine granules), which has a coating layer comprising a polymer affording a casting film having an elongation at break of about 100-about 700%. Hence, the controlled release fine granules of the present invention are (1) fine granules obtained by coating the enteric fine granules comprising the pharmaceutically active ingredient with the aforementioned polymer or (2) fine granules obtained by coating cardinal remedy fine granules comprising a pharmaceutically active ingredient with an enteric polymer comprising the aforementioned polymer.

When the "fine granules" are obtained by coating the enteric fine granules comprising the pharmaceutically active ingredient with the aforementioned polymer, a coating layer comprising a polymer affording a casting film having an elongation at break of about 100-about 700% is preferably the outermost layer of the fine granules. The amount of the aforementioned polymer to be coated is about 5-about 30 wt %, preferably about 5-about 25 wt %, more preferably about 5-about 20 wt %, relative to the enteric fine granules comprising the pharmaceutically active ingredient.

One embodiment of the enteric fine granules comprising the pharmaceutically active ingredient comprises a "pharmaceutically active ingredient layer" on the "core", upon which an "intermediate layer", and further an "enteric film layer" thereon. The "core" and "intermediate layer" are mentioned below.

In the present invention, the "core granule" means, for example, a "core" and layers such as a "pharmaceutically active ingredient layer", an "intermediate layer" and the like covering the core, and refers to the granules before applying a controlled release film.

The enteric fine granules in the present invention are preferably pH-dependent controlled release fine granules that release a pharmaceutically active ingredient in a pH-dependent manner. The pH-dependent controlled release fine granules are, for example, those obtained by coating core granules comprising the pharmaceutically active ingredient with fine granules coated with a controlled release film (enteric coating layer, diffusion control coating layer or a combination of these and the like), or fine granules comprising a pharmaceutically active ingredient dispersed in a controlled release matrix and the like. The release of a pharmaceutically active ingredient is controlled by coating fine granules comprising the pharmaceutically active ingredient with a film capable of controlling release of the pharmaceutically active ingredient, or dispersing the pharmaceutically active ingredient in a controlled release matrix.

The pH-dependent manner means dissolution/elution in an environment with a pH of a given level or higher. With general enteric coating, the enteric fine granules are dissolved/eluted and release pharmaceutically active ingredients starts at a pH of about 5.5. In the present invention, elution preferably starts at a higher pH (preferably not less than pH 6.0 and not more than 7.5, more preferably not less than pH 6.5 and less than 7.2) and release of the pharmaceutically active ingredient in the stomach is preferably well controlled. That is, examples of the controlled release film in the present invention include a general enteric film that dissolves at about pH 5.5, as well as films having a more superior release delaying function or a release-sustaining function of a pharmaceutically active ingredient such as a film that dissolves at a higher pH region and a pH-dependent manner, or a diffusion control coating layer wherein the film itself is not dissolved but a pharmaceutically active ingredient is released through the film itself or fine pores formed in the film and the like.

The film in the controlled release film includes not only a film-like coating layer but also a coating layer having a greater thickness, and further, not only a coating layer that completely covers core granules or layers inside, but also a coating layer that covers most of the core granules or layers inside, though partially not covering them. The coating layer that covers most of the core granules or layers inside covers at least 80% or more of the core granules or surface of the layers inside, preferably the entirety thereof.

In the present invention, the polymer to be comprised in the enteric film preferably shows release control property. Examples thereof include hypromellose phthalate, cellulose acetate phthalate, carboxymethyl ethyl cellulose, methyl methacrylate-methacrylic acid copolymer, methacrylic acid-ethyl acrylate copolymer, methacrylic acid-methyl acrylate-methyl methacrylate copolymer, hydroxypropyl methylcellulose acetate succinate, polyvinyl acetate phthalate and shellac and the like. Specific examples of commercially available products include polymers such as hypromellose phthalate (HP-55, HP-50, manufactured by Shin-Etsu Chemical Co., Ltd.), cellulose acetate phthalate, carboxymethyl ethyl cellulose (CMEC, manufactured by Freund Corporation), methyl methacrylate-methacrylic acid copolymer (Eudragit L100 (methacrylic acid copolymer L) or Eudragit S100 (methacrylic acid copolymer S), manufactured by Evonik Roehm), methacrylic acid-ethyl acrylate copolymer (Eudragit L100-55 (dried methacrylic acid copolymer LD) or Eudragit L30D-55 (methacrylic acid copolymer LD), manufactured by Evonik Roehm), methacrylic acid-methyl acrylate-methyl methacrylate copolymer (Eudragit FS30D, manufactured by Evonik Roehm), hydroxypropyl methylcellulose acetate succinate (HPMCAS manufactured by Shin-Etsu Chemical Co., Ltd.), polyvinyl acetate phthalate, shellac and the like, preferably methyl methacrylate-methacrylic acid copolymer, methacrylic acid-ethyl acrylate copolymer, methacrylic acid-methyl acrylate-methyl methacrylate copolymer and the like. These polymer substances may be used in a mixture of two or more kinds (preferably 2-3 kinds).

Preferable embodiment of use in a mixture include a mixed polymer of a methacrylic acid-methyl acrylate-methyl methacrylate copolymer and a methacrylic acid-ethyl acrylate copolymer.

A preferable mixing ratio of the methacrylic acid-methyl acrylate-methyl methacrylate copolymer and methacrylic acid-ethyl acrylate copolymer is 50-100:50-0, preferably 85-100:15-0, in a weight ratio.

In a particularly preferable embodiment of the fine granules showing controlled release of a pharmaceutically active ingredient, the core granule comprising at least one pharmaceutically active ingredient is coated with a controlled release film.

Such core granule is obtained by coating an inactive carrier as a core with a pharmaceutically active ingredient, or by granulation using a pharmaceutically active ingredient and excipient generally used for preparation making. For example, it can be produced by the method described in JP-A-63-301816.

The average particle size of the "core" may be about 40 to about 350 µm, preferably about 50 to about 250 µm, more preferably 100 to 250 µm, particularly preferably about 100 to about 200 µm. The cores having the above-described average particle size include particles all of which pass through a No. 48 (300 µm) sieve, about 5 w/w % or less of the entirety of which remains on a No. 60 (250 µm) sieve, and about 10 w/w % or less of the entirety of which passes through a No. 270 (53 µm) sieve. The specific volume of the "core" is 5 ml/g or less, preferably 4 ml/g or less, more preferably 3 ml/g or less.

Examples of the inactive carrier to be used as the "core" include (1) a spherical granule of crystalline cellulose and lactose, (2) a spherical granule having a size of 75 to 300 µm of crystalline cellulose (manufactured by Asahi Kasei Corporation, CELPHERE), (3) a granule having a size of 50 to 250 µm produced from lactose (9 parts) and α-starch (1 part)

by stirring granulation, (4) a micro particle having a size of 250 μm or smaller obtained by classification of microcrystalline cellulose spherical granules described in JP-A 61-213201, (5) a processed product of wax which is formed into a sphere by spray chilling or melt granulation, (6) a processed product such as a gelatin bead comprising an oil ingredient, (7) calcium silicate, (8) starch, (9) a porous particle such as chitin, cellulose, chitosan or the like, (10) a bulk powder of granulated sugar, crystalline lactose, crystalline cellulose, sodium chloride or the like, and a processed preparation thereof. Further, these cores may be produced by a per se known grinding method or granulation method, and then sieved to prepare particles having the desired particle diameter.

Examples of the "spherical granule of crystalline cellulose and lactose" include (i) a spherical granule having a size of 100 to 200 μm produced from crystalline cellulose (3 parts) and lactose (7 parts) (e.g., Nonpareil 105 (70-140) (particle diameter: 100 to 200 μm), manufactured by Freund Corporation), (ii) a spherical granule having a size of 150 to 250 μm produced from crystalline cellulose (3 parts) and lactose (7 parts) (e.g., Nonpareil NP-7:3, manufactured by Freund Corporation), (iii) a spherical granule having a size of 100 to 200 μm produced from crystalline cellulose (4.5 parts) and lactose (5.5 parts) (e.g., Nonpareil 105T (70-140) (particle diameter: 100 to 200 μm), manufactured by Freund Corporation), (iv) a spherical granule having a size of 150 to 250 μm produced from crystalline cellulose (5 parts) and lactose (5 parts) (e.g., Nonpareil NP-5:5, manufactured by Freund Corporation) and the like.

In order to produce a preparation retaining a suitable strength and having excellent solubility, the "core" is preferably a spherical granule of crystalline cellulose and lactose, and more preferably a spherical granule of crystalline cellulose and lactose which contains 50% by weight or more of lactose. A spherical granule comprising about 20-about 50 wt %, preferably about 40-about 50 wt %, of crystalline cellulose and about 50-about 80 wt %, preferably about 50-about 60 wt %, of lactose is also preferable.

Examples of the "spherical crystalline cellulose" include CELPHERE CP-203 (particle size 150-300 μm), CP-102 (particle size 106-212 μm), SCP-100 (particle size 75-212 μm) (each manufactured by Asahi Kasei Chemicals Co., Ltd.) and the like.

As the core to be used in the present invention, spherical crystalline cellulose or a spherical granulation product of crystalline cellulose and lactose is preferable, and a 100-200 μm spherical granulation product of 100-250 μm of spherical crystalline cellulose or crystalline cellulose (4.5 parts) and lactose (5.5 parts) is more preferable.

When core granules are obtained by coating a pharmaceutically active ingredient on the core of an inactive carrier, as in the below-mentioned (1) fine granules having an enteric coating layer on core granules, and (2) fine granules having a diffusion control coating layer on core granules, or fine granules having an enteric coating layer and a diffusion control coating layer in combination on core granules and the like, for example, core granules can be prepared by wet granulation using a rotary fluidized bed granulator (SPIR-A-FLOW (manufactured by Freund Corporation), MP-10 TOKU-2 type (manufactured by POWREX Corporation), a centrifugation rolling granulator (CF-mini, CF-360, manufactured by Freund Corporation) or a rotary fluidized bed granulator (MP-10, manufactured by POWREX Corporation) and the like. Alternatively, a pharmaceutically active ingredient may be sprayed for coating on while adding a spray solution comprising a binder and the like on the core of an inactive carrier, and the like. While the production apparatus is not limited, for example, a centrifugation rolling granulator and the like are preferably used for production by the latter coating. The coating using the aforementioned two kinds of apparatuses may be combined to apply a pharmaceutically active ingredient in two steps. When the core of an inactive carrier is not used, core granules are obtained by the use of an excipient such as lactose, sucrose, mannitol, cornstarch, crystalline cellulose and the like and a pharmaceutically active ingredient, a binder such as hypromellose (HPMC), hydroxypropyl cellulose, methylcellulose, polyvinyl alcohol, macrogol, pluronic F68, gum arabic, gelatin, starch and the like, and adding, where necessary, a disintegrant such as carboxymethylcellulose sodium, calcium carboxymethylcellulose, croscarboxymethylcellulose sodium (Ac-Di-Sol, manufactured by FMC International), polyvinylpyrrolidone, low-substituted hydroxypropyl cellulose (L-HPC) and the like in a stirring granulator, a wet extrusion-granulator, a fluid bed granulator and the like. The aforementioned coating method can also be utilized for coating of particles other than core granules.

In the present invention, a basic inorganic salt is preferably added to granules, specifically, core granules comprising a pharmaceutically active ingredient, so as to stabilize the pharmaceutically active ingredient (particularly, a pharmaceutically active ingredient unstable to acid) in a preparation. The basic inorganic salt is preferably contacted with a pharmaceutically active ingredient, and preferably uniformly mixed with a pharmaceutically active ingredient.

Examples of the "basic inorganic salt" include basic inorganic salts of sodium, potassium, magnesium and/or calcium (e.g., sodium carbonate, sodium hydrogen carbonate, potassium carbonate, potassium hydrogen carbonate, heavy magnesium carbonate, magnesium carbonate, magnesium oxide, magnesium hydroxide and the like).

The amount of the basic inorganic salt to be used is appropriately determined according to the kind of the basic inorganic salt, and, for example, about 0.3-about 200 wt %, preferably about 1-about 100 wt %, more preferably about 10-about 50 wt %, most preferably about 20-about 40 wt %, of the pharmaceutically active ingredient.

Core granules (granulates comprising a pharmaceutically active ingredient) may be coated with a polymer substance to form an intermediate coating layer before applying the below-mentioned controlled release film. Such granules may be used as core granules. For example, when the pharmaceutically active ingredient is unstable to acid such as PPI and the like, an intermediate coating layer may be formed to shut off a direct contact between the core granules and the controlled release film, which is preferable for improving the stability of the pharmaceutically active ingredient. Such an intermediate coating layer may be formed with a plurality of layers. The content of a polymer substance in the controlled release film is about 30-about 100 wt %, preferably about 35-about 90 wt %, more preferably about 40-about 80 wt %, of the granules coated with an intermediate coating layer. The content of a polymer substance in the controlled release film is preferably about 50-about 100 wt % of the particles coated with an intermediate coating layer.

Examples of the coating substance for an intermediate coating layer include a polymer substance such as L-HPC, hydroxypropyl cellulose, HPMC (e.g., TC-5 etc.), polyvinylpyrrolidone, polyvinyl alcohol, methylcellulose, hydroxyethylmethylcellulose and the like, sucrose [purified sucrose (pulverized (powder sugar), non-pulverized) etc.], starch sugar such as cornstarch and the like, which are appropriately added with saccharides such as lactose, honey and sugar alcohol (D-mannitol, erythritol and the like) and the like, and the like. Preferred are L-HPC, HPMC, D-mannitol, and a mixture of these. The intermediate coating layer may appropriately contain, besides these, an excipient (e.g., masking agent (titanium oxide etc.), an antistatic agent (titanium oxide, talc etc.)) added, where necessary, for the production of a preparation.

The amount of the intermediate coating layer to be applied is generally about 0.02 part by weight-about 1.5 parts by weight, preferably about 0.05-about 1 part by weight, per 1 part by weight of the "granules comprising a pharmaceutically active ingredient".

The coating can be performed by a conventional method. For example, in a preferable method, the aforementioned intermediate coating layer component is diluted with purified water and the like, and sprayed as a liquid. In this case, a binder such as hydroxypropyl cellulose and the like is preferably sprayed concurrently.

The fine granules showing controlled release of a pharmaceutically active ingredient and comprised in the preparation of the present invention are desirably fine granules having an enteric coating layer and/or a diffusion control coating layer on the aforementioned core granules, or fine granules wherein a pharmaceutically active ingredient is dispersed in a controlled release matrix.

In the controlled release film of the present invention, an enteric coating layer or a diffusion control coating layer may be applied. Moreover, the controlled release film of the present invention may comprise an enteric coating layer and a diffusion control coating layer in combination.

(1) Fine Granules Having Enteric Coating Layer on Core Granules

In an embodiment of such fine granules, controlled release film is formed on the aforementioned core granule, and the film is preferably fine granules having an enteric coating layer. The enteric coating layer in the present invention comprises a coating substance (a polymer substance) which dissolves/elutes in a pH-dependent manner to control release of a pharmaceutically active ingredient, and the substance forms an enteric coating layer. The "pH-dependent manner" means dissolution/elution in an environment with a pH of a given level or higher to release a pharmaceutically active ingredient, as mentioned above.

The enteric coating layer comprises a polymer affording a casting film having an elongation at break of about 100-about 700%.

Moreover, two or more kinds (preferably 2-3 kinds) of polymers as coating substances for the aforementioned enteric coating layer may be sequentially coated to form a multi-layer. To form two or more kinds of film that dissolve in different pH ranges, for example, a polymer that dissolves at not less than pH 6.0 and a polymer that dissolves at not less than pH 7.0 may be used in combination. For example, a polymer that dissolves at not less than pH 6.0 and a polymer that dissolves at not less than pH 7.0 may be used in combination at a ratio of 1:0.5-1:5.

Furthermore, the enteric coating layer in the present invention may contain, where necessary, plasticizer such as polyethylene glycol, dibutyl sebacate, diethyl phthalate, triacetine, triethyl citrate and the like, stabilizer, and the like. For example, when the plasticizer is triethyl citrate and the amount of triethyl citrate is increased, the amount of the enteric coating layer decreases, whereby the fine granules are downsized, thus realizing downsizing of the whole preparation. The amount of the coating substance used for release control is about 20-about 100 wt %, preferably about 30-about 90 wt %, more preferably about 40-about 80 wt %, relative to the fine granules with a controlled release film layer. The elution of the pharmaceutically active ingredient from the thus-obtained fine granules showing controlled release of the pharmaceutically active ingredient is desirably not more than 10% in 2 hr as expressed by the dissolution ratio of a pH 1.2 solution, and not more than 5% in 1 hr and not less than 60% in 8 hr as expressed by the dissolution ratio of a pH 6.8 solution.

The thus-obtained fine granules having a controlled release film may be coated with a substance that becomes viscous on contact with water, such as polyethylene oxide (PEO, for example, Polyox WSR303 (molecular weight 7000000), Polyox WSR Coagulant (molecular weight 5000000), Polyox WSR 301% (molecular weight 4000000), Polyox WSR N-60K (molecular weight 2000000), Polyox WSR 205 (molecular weight 600000); manufactured by Dow Chemical), hypromellose (HPMC, Metlose 90SH10000, Metlose 90SH50000, Metlose 90SH30000, manufactured by Shin-Etsu Chemical Co., Ltd.), carboxymethyl cellulose (CMC-Na, Sanlose F-1000MC), hydroxypropyl cellulose (HPC, for example, HPC-H, manufactured by Nippon Soda Co., Ltd.), hydroxyethyl cellulose (HEC), carboxyvinyl polymer (Hibiswako (R)103, 104, 105, manufactured by Wako Pure Chemical Industries, Ltd.; carbopol943, manufactured by Goodrich), chitosan, sodium alginate, pectin and the like.

(2) Fine Granules Having Diffusion Control Coating Layer on Core Granules

The fine granules showing controlled release of a pharmaceutically active ingredient are fine granules having a controlled release film on the core granules comprising the pharmaceutically active ingredient. As the film, fine granules having a diffusion control coating layer can be mentioned. The diffusion control coating layer in the present invention is a layer that controls release of a pharmaceutically active ingredient by diffusion. Such a diffusion control coating layer contains a diffusion control film-forming polymer. Examples of the diffusion control film-forming polymer include ethyl acrylate-methyl methacrylate-trimethylammonioethyl methacrylate chloride copolymer (Eudragit RS (aminoalkyl-methacrylate copolymer RS) and Eudragit RL (aminoalkyl-methacrylate copolymer RL), manufactured by Evonik Roehm), methyl methacrylate-ethyl acrylate copolymer (Eudragit NE30D, manufactured by Evonik Roehm), ethylcellulose and the like. Preferably, ethyl acrylate-methyl methacrylate-trimethylammonioethyl methacrylate chloride copolymer and methyl methacrylate-ethyl acrylate copolymer can be mentioned. These diffusion control film-forming polymers can also be used as a mixture of one or more kinds thereof.

Two or more kinds of diffusion control film-forming polymers in the diffusion control coating layer may be a mixture at a suitable ratio, and can also be used as a mixture with hydrophilic pore-forming substance HPMC, HPC, carboxyvinyl polymer, polyethylene glycol 6000, lactose, mannitol, organic acid and the like at a given ratio.

The controlled release film in the present invention may be a film comprising an enteric coating layer and a diffusion control coating layer in combination. The fine granules showing controlled release of a pharmaceutically active ingredient may be coated with a controlled release film comprising the aforementioned diffusion control coating layer and the enteric coating layer of the aforementioned (1) in combination. Examples thereof include (i) a form wherein core granules comprising the pharmaceutically active ingredient are coated with an enteric coating layer, and then a diffusion control coating layer, (ii) a form wherein core granules comprising the pharmaceutically active ingredient are coated with a diffusion control coating layer, and then an enteric coating layer, and (iii) a form wherein core granules comprising the pharmaceutically active ingredient are coated with a mixture of a coating substance to control release of a pharmaceutically active ingredient in a pH-dependent manner, which forms the aforementioned enteric coating layer, and the aforementioned diffusion control film-forming polymer to form a diffusion control coating layer and the like.

The coating layers of the aforementioned (i) and (ii) may be form a multi-layer as necessary. The coating substance to control release of a pharmaceutically active ingredient in a pH-dependent manner, and the diffusion control film-forming polymer of the aforementioned (iii) may be uniformly mixed or partly nonuniform. The mixing ratio of the mixture of a coating substance to control release of a pharmaceutically active ingredient in a pH-dependent manner and the diffusion control film-forming polymer is 1:10-10:1, more preferably 1:5-10:1, still more preferably 1:1-9:1.

To provide fine granules controlled to release a pharmaceutically active ingredient after a given lag time, a swellable substance such as disintegrant and the like may be coated before coating the aforementioned diffusion control coating layer so as to form a disintegrant layer between the core granules and the controlled release film. For example, a swellable substance such as croscarmellose sodium (Ac-Di-Sol, manufactured by FMC International), carmellose calcium (ECG505, manufactured by Gotoku Yakuhin), crospovidone (ISP Inc), low-substituted hydroxypropyl cellulose (L-HPC, manufactured by Shin-Etsu Chemical Co., Ltd.) and the like may be primarily applied onto the core granules comprising a pharmaceutically active ingredient, and ethyl acrylate-methyl methacrylate-trimethylammonioethyl methacrylate chloride copolymer (Eudragit RS or Eudragit RL, manufactured by Evonik Roehm), methyl methacrylate-ethyl acrylate copolymer (Eudragit NE30D, manufactured by Evonik Roehm), ethylcellulose and the like alone or in a mixture, or a diffusion control film obtained by mixing with a hydrophilic pore-forming substance HPMC, HPC, carboxyvinyl polymer, polyethylene glycol 6000, lactose, mannitol, organic acid and the like at a given ratio is preferably coated secondarily.

Such coating substance for secondary coating may be an enteric polymer that releases a pharmaceutically active ingredient in a pH-dependent manner such as hypromellose phthalate (HP-55, HP-50, manufactured by Shin-Etsu Chemical Co., Ltd.), cellulose acetate phthalate, carboxymethyl ethyl cellulose (CMEC, manufactured by Freund Corporation), methyl methacrylate-methacrylic acid copolymer (Eudragit L100 (methacrylic acid copolymer L) or Eudragit S100 (methacrylic acid copolymer S), manufactured by Evonik Roehm), methacrylic acid-ethyl acrylate copolymer (Eudragit L100-55 (dried methacrylic acid copolymer LD) or Eudragit L30D-55% (methacrylic acid copolymer LD), manufactured by Evonik Roehm), methacrylic acid-methyl acrylate-methyl methacrylate copolymer (Eudragit FS30D, manufactured by Evonik Roehm), hydroxypropyl methylcellulose acetate succinate (HPMCAS manufactured by Shin-Etsu Chemical Co., Ltd.), polyvinyl acetate phthalate, shellac and the like.

The amount of the coating substance used for release control by diffusion control is desirably about 1-about 200%, preferably about 2-about 100%, more preferably about 5-about 60%, relative to the core granules.

The coating may contain, where necessary, a plasticizer such as polyethylene glycol, dibutyl sebacate, diethyl phthalate, triacetine, triethyl citrate and the like, a stabilizer and the like. The thus-obtained fine granules showing controlled release of a pharmaceutically active ingredient may be coated with a substance that becomes viscous on contact with water, such as polyethylene oxide (PEO, for example, Polyox WSR303 (molecular weight 7000000), Polyox WSR Coagulant (molecular weight 5000000), Polyox WSR 301 (molecular weight 4000000), Polyox WSR N-60K (molecular weight 2000000), Polyox WSR 205 (molecular weight 600000); manufactured by Dow Chemical), hypromellose (HPMC, Metlose 90SH10000, Metlose 90SH50000, Metlose 90SH30000, manufactured by Shin-Etsu Chemical Co., Ltd.), carboxymethyl cellulose (CMC-Na, Sanlose F-1000MC), hydroxypropyl cellulose (HPC, for example, HPC-H, manufactured by Nippon Soda Co., Ltd.), hydroxyethyl cellulose (HEC), carboxyvinyl polymer (Hibiswako (R)103, 104, 105, manufactured by Wako Pure Chemical Industries, Ltd.; carbopol943, manufactured by Goodrich), chitosan, sodium alginate, pectin and the like, and the resulting fine granules may be used as controlled release fine granules.

When the aforementioned (1) fine granules having enteric coating layer on core granules and (2) fine granules having a diffusion control coating layer on the core granules are fine granules having two or more kinds of controlled release films with different release conditions of the pharmaceutically active ingredient, a layer comprising a pharmaceutically active ingredient may be formed between the controlled release films. An embodiment of the multi-layer structure comprising a pharmaceutically active ingredient between the controlled release films includes fine granules obtained by coating fine granules showing controlled release of a pharmaceutically active ingredient due to the controlled release film with a pharmaceutically active ingredient and then with the aforementioned controlled release film.

(3) Fine Granules with Pharmaceutically Active Ingredient Dispersed in Release Control Matrix Another form of the fine granules showing controlled release of a pharmaceutically active ingredient includes fine granules with a pharmaceutically active ingredient dispersed in a release control matrix. Such controlled release fine granules can be produced by uniformly dispersing a pharmaceutically active ingredient in wax such as hydrogenated castor oil, hydrogenated rapeseed oil, stearic acid, stearyl alcohol and the like, or a hydrophobicity carrier such as polyglycerin fatty acid ester and the like. The release control matrix is a composition wherein a pharmaceutically active ingredient is uniformly dispersed in a carrier and, where necessary, an excipient such as lactose, mannitol, cornstarch, crystalline cellulose and the like, generally used for formulation of preparations, may be dispersed together with the pharmaceutically active ingredient. Furthermore, a powder that produces viscose gel upon contact with water, such as polyoxyethyleneoxide, crosslinking type acrylic acid polymer (Hibiswako (R)103, 104, 105, carbopol), HPMC, HPC, chitosan and the like may be dispersed in the release control matrix together with a pharmaceutically active ingredient and an excipient.

For preparation, a method known per se such as spray drying, spray chilling, melt granulation and the like can be employed.

The thus-obtained fine granules showing controlled release of a pharmaceutically active ingredient may be coated with a substance that becomes viscous upon contact with water, such as polyethylene oxide (PEO, for example, Polyox WSR303 (molecular weight 7000000), Polyox WSR Coagulant (molecular weight 5000000), Polyox WSR 301 (molecular weight 4000000), Polyox WSR N-60K (molecular weight 2000000), Polyox WSR 205 (molecular weight 600000); manufactured by Dow Chemical), hypromellose (HPMC, Metlose 90SH10000, Metlose 90SH50000, Metlose 90SH30000, manufactured by Shin-Etsu Chemical Co., Ltd.), carboxymethyl cellulose (CMC-Na, Sanlose F-1000MC), hydroxypropyl cellulose (HPC, for example, HPC-H, manufactured by Nippon Soda Co., Ltd.), hydroxyethyl cellulose (HEC), carboxyvinyl polymer (Hibiswako (R)103, 104, 105, manufactured by Wako Pure Chemical Industries, Ltd.; carbopol943, manufactured by Goodrich), chitosan, sodium alginate, pectin and the like and the obtained fine granules may be used as controlled release fine granules.

The controlled release fine granules may have the aforementioned various release control films, a release control matrix and the like in combination.

By forming an overcoat with a coating layer comprising a polymer affording a casting film having an elongation at break of about 100%-about 700% after obtaining the aforementioned enteric fine granules, "fine granules" showing suppressed breakage during tabletting can be obtained.

Preferably, the coating layer comprising the polymer is the outermost layer.

On the other hand, when the aforementioned "(1) fine granules having enteric coating layer on core granules" wherein the enteric coating layer comprises a polymer affording a casting film having an elongation at break of about 100-about 700% are used, "fine granules" showing suppressed breakage during tabletting can be obtained even without formation of an overcoat with a coating layer comprising a polymer affording a casting film having an elongation at break of about 100-about 700% after obtaining the enteric fine granules.

For example, when the aforementioned polymer affording a casting film having an elongation at break of about 100-about 700% is used alone, a mixture of the polymer and other enteric polymer may be used.

Examples of other enteric polymer include aqueous enteric polymer bases such as hypromellose phthalate, cellulose acetate phthalate, hydroxypropyl methylcellulose acetate succinate, methacrylic acid copolymer [for example, Eudragit L30D-55 (trade name; manufactured by Evonik Roehm), Kollicoat MAE30DP (trade name; manufactured by BASF), POLYQUID PA30 (trade name; manufactured by Sanyo Chemical Industry) and the like], carboxymethyl ethyl cellulose, shellac and the like, and the like. Particularly, a methacrylic acid copolymer is preferable.

A preferable embodiment to achieve the effect of the present invention with enteric fine granules without the polymer overcoat is the use of a polymer affording a casting film having an elongation at break of about 100-about 700% in the enteric coating layer in a proportion of 1-100 wt %, preferably 5-80 wt %, relative to the core granules comprising a pharmaceutically active ingredient.

A preferable embodiment of a mixture with other enteric polymers is a mixed polymer of a methacrylic acid-methyl acrylate-methyl methacrylate copolymer and a methacrylic acid-ethyl acrylate copolymer.

A preferable mixing ratio of the methacrylic acid-methyl acrylate-methyl methacrylate copolymer and the methacrylic acid-ethyl acrylate copolymer is 50-100:50-0, preferably 85-100:15-0, in a weight ratio.

The enteric coating layer may contain a plasticizer. As the plasticizer, triethyl citrate, polyethylene glycol, diethyl phthalate, triacetine, glycerol, glycerol fatty acid ester, sesame oil, castor oil and the like can be mentioned, with preference given to triethyl citrate.

The content of the plasticizer in the enteric film layer is about 1-about 20 wt %, preferably about 3-about 15 wt %, more preferably about 5-about 12 wt %, of the weight of the polymer solid content.

The enteric fine granules may further form a coating layer comprising a water-soluble sugar alcohol (mannitol and the like), irrespective of with or without an overcoat with a coating layer comprising a polymer affording a casting film having an elongation at break of about 100-about 700%. When such water-soluble sugar alcohol is added, (I) since mannitol is used as a preparation additive other than fine granules, affinity with fine granules can be enhanced, and (II) coagulation of fine granules can be prevented.

In an attempt to achieve a faster rise of blood concentration after dosing, earlier efficacy expression, sustained therapeutically effective concentration for a long time, reduced administration frequency, an effective treatment with a small dose, and reduction of side effects caused by the rise of the blood concentration, the orally-disintegrating solid preparation of the present invention may contain two or more kinds (preferably 2-3 kinds) of fine granules with different release rates of the pharmaceutically active ingredient.

The size of the fine granules in the present invention is about 500 µm or below, preferably about 400 µm or below (e.g., about 100 µm-about 500 µm, preferably about 100 µm-about 400 µm). Using two or more kinds of fine granules with different release rates, a preparation controlling release of a pharmaceutically active ingredient from fine granules continuously or in a pulse-like manner can also be designed. The fine granules with different release rates of a pharmaceutically active ingredient may contain the same pharmaceutically active ingredient, or a combination agent comprising other pharmaceutically active ingredient may be produced.

That is, the present invention provide an orally-disintegrating solid preparation comprising a combination of (1) fine granules showing controlled release of a pharmaceutically active ingredient, which have a coating layer comprising a polymer affording a casting film having an elongation at break of about 100-about 700% and (2) fine granules with different release rate of a pharmaceutically active ingredient from that of the fine granules of (1).

For example, the preparation of the present invention is, for example, an orally-disintegrating solid preparation comprising (1) fine granules A showing controlled release of a pharmaceutically active ingredient, which have a coating layer comprising a polymer affording a casting film having an elongation at break of about 100-about 700% and (2) fine granules B with different release rate of a pharmaceutically active ingredient from that of the fine granules of (1). While this preparation is explained in detail as one embodiment, the preparation is not limited thereto.

The fine granules A are fine granules showing controlled release of a pharmaceutically active ingredient and having a coating layer comprising a polymer affording a casting film having an elongation at break of about 100-about 700%, as mentioned above. Preferably, the aforementioned coating layer is the outermost layer of fine granules A. When desired, a coating layer comprising a water-soluble sugar alcohol (mannitol and the like) can also be formed.

One embodiment of fine granules B in the aforementioned preparation of the present invention is shown in the following.

The average particle size of the fine granules B in the present invention is about 500 µm or below, preferably about 400 µm or below (e.g., about 100 µm-about 500 µm, preferably about 100 µm-about 400 µm), in order to prevent rough or powdery texture during administration of the orally-disintegrating solid preparation of the present invention.

The pharmaceutically active ingredient in fine granules B is contained, for example, in a proportion of 1-50 parts by weight, preferably 2-20 parts by weight, per the weight of 100 parts by weight of the fine granules B.

The pharmaceutically active ingredient in fine granules A and fine granules B in the preparation of the present invention may be the same. In this case, the weight ratio of the pharmaceutically active ingredient is 1:10-10:1.

When the pharmaceutically active ingredient is unstable to acid, such as PPI and the like, a basic inorganic salt is preferably added to stabilize the pharmaceutically active ingredient in the preparation. Examples of the basic inorganic salt include those similar to fine granules A.

The amount of the basic inorganic salt to be used is appropriately determined according to the kind of the basic inorganic salt, and is, for example, 0.3-200 wt %, preferably 1-100 wt %, more preferably 10-50 wt %, most preferably 20-40 wt %, relative to the pharmaceutically active ingredient.

The fine granules B may comprise a core with or without a pharmaceutically active ingredient. The core is similar to the inactive carrier that fine granules A may contain.

The core is coated with a pharmaceutically active ingredient and the like, and may be coated by a method known per se for the purpose of masking of taste and odor, enteric property or sustained release. Examples of the coating agent here include an aqueous enteric polymer base, such as hypromellose phthalate, cellulose acetate phthalate, hydroxypropyl methylcellulose acetate succinate, methacrylic acid copolymer [for example, Eudragit L30D-55 (trade name; manufactured by Evonik Roehm), Kollicoat MAE30DP (trade name; manufactured by BASF), POLYQUID PA30 (trade name; manufactured by Sanyo Chemical Industry) and the like], methacrylic acid-methyl acrylate-methyl methacrylate copolymer (e.g., Eudragit FS30D and the like), carboxymethyl ethyl cellulose, shellac and the like; sustained-release substance such as methacrylic acid copolymer [for example, Eudragit NE30D (trade name), Eudragit RL30D (trade name), Eudragit RS30D (trade name) and the like] and the like; water-soluble polymer; plasticizers such as triethyl citrate, polyethylene glycol, acetylation monoglyceride, triacetine, castor oil and the like, and the like.

These can also be used as a mixture of one or more kinds thereof.

Specific examples of fine granules B in the present invention include a form wherein an enteric coating layer is formed on the core granules comprising the pharmaceutically active ingredient. The enteric coating layer in fine granules B in the present invention contains one or more kinds of aqueous enteric polymer bases selected from hypromellose phthalate, cellulose acetate phthalate, hydroxypropyl methylcellulose acetate succinate, methacrylic acid copolymer, methacrylic acid-methyl acrylate-methyl methacrylate copolymer, carboxymethyl ethyl cellulose and shellac.

As the enteric coating layer in fine granules B, a mixed polymer of a methacrylic acid-ethyl acrylate copolymer (e.g., Eudragit L30D-55) and a methacrylic acid-methyl acrylate-methyl methacrylate copolymer (e.g., Eudragit FS30D) is preferable. A preferable mixing ratio of the methacrylic acid-methyl acrylate-methyl methacrylate copolymer and the methacrylic acid-ethyl acrylate copolymer is 0-85:100-15, preferably 70-85:30-15, in a weight ratio.

The fine granules B are preferably pH-dependent controlled release fine granules comprising a pharmaceutically active ingredient coated with a controlled release film comprising a polymer substance that dissolves at not less than pH 6.0 and not more than pH 7.5. The controlled release film is generally formed on the core granules via an intermediate coating layer, and the content of the polymer substance in the controlled release film is about 10-about 70 wt %, preferably about 15-about 65 wt %, more preferably about 20-about 60 wt %, relative to fine granules coated with the intermediate coating layer. By controlling the polymer substance content, the releaseability of the pharmaceutically active ingredient of such fine granules B can be controlled and, as a result, can be more rapidly released than fine granules A.

The enteric coating layer of fine granules B can contain a polymer substance that dissolves generally at not less than pH 5.0 and not more than pH 6.0. As a result, fine granule B is more rapidly released than fine granules A.

The enteric coating layer is preferably formed using an aqueous enteric polymer base and a sustained-release substrate and, where necessary, a plasticizer and the like in combination.

Preferred as an aqueous enteric polymer base are methacrylic acid-methyl acrylate-methyl methacrylate copolymer, methacrylic acid-ethyl acrylate copolymer, hydroxypropyl methylcellulose acetate succinate and carboxymethyl ethyl cellulose.

The enteric coating layer of fine granules B in the present invention may contain a sustained-release substrate. The sustained-release substrate is preferably a methyl methacrylate-ethyl acrylate copolymer or ethylcellulose.

The amount of the aforementioned sustained-release substrate to be used is about 5-about 30 parts by weight, preferably about 5-about 15 parts by weight, per 100 parts by weight of the aqueous enteric polymer base.

The fine granules B can also be produced by a known granulation method, as in the case of fine granules A.

The "granulation method" includes, for example, rotary granulation method (e.g., centrifugal rolling granulation, etc.), fluidized-bed granulation (e.g., rotary fluidized bed granulation, fluidized granulation, etc.), stirring granulation and the like. Among others, preferred is fluidized-bed granulation method, more preferred is rotary fluidized-bed granulation method.

Concrete example of the "rotary granulation method" includes a method using "CF apparatus" manufactured by Freund Corporation and the like. Concrete examples of the "rotary fluidized-bed granulation method" include methods using "SPIR-A-FLOW", "multi plex" manufactured by Powrex Corporation, "New-Marumerizer" manufactured by Fuji Paudal Co., Ltd., and the like. The method for spraying the mixture can be suitably selected in accordance with the kind of granulator, and may be, for example, any one of a top spray method, a bottom spray method, a tangential spray method, and the like. Among others, a tangential spray method is preferred.

More specifically, for example, using the production method (coating method) described in JP-A-5-092918, and by a method of coating a core comprising crystalline cellulose and lactose with a pharmaceutically active ingredient (e.g., a pharmaceutically active ingredient unstable to acid) and, where necessary, a basic inorganic salt, a binder, a lubricant, an excipient, a water-soluble polymer and the like, core granules comprising the pharmaceutically active ingredient are obtained.

As the basic inorganic salt, binder, lubricant and excipient, those mentioned above and the like are used.

While the core may contain a pharmaceutically active ingredient, since a coating layer comprising a pharmaceutically active ingredient can control releaseability of the pharmaceutically active ingredient, the core may not contain a pharmaceutically active ingredient.

The core is preferably as uniformly spherical as possible so as to minimize variation of coating amount.

The proportion of the coating layer to the core can be selected from the range permitting control of the dissolution property of the pharmaceutically active ingredient and the granule size of the composition and is, for example, generally about 50-about 400 parts by weight per 100 parts by weight of the core.

The coating layer may be formed by a plurality of coating layers. A combination of various coating layers, such as a coating layer free of a pharmaceutically active ingredient, coating layer for base, enteric coating layer and the like, constituting the plural coating layers can be appropriately selected.

For coating of the core, for example, a mixture of the aforementioned pharmaceutically active ingredient and water-soluble polymer is used. The mixture may be a solution or a dispersion, which can be prepared using water or an organic solvent such as ethanol and the like, or a mixture thereof.

While the concentration of the water-soluble polymer in the mixture varies depending on the proportion of the pharmaceutically active ingredient and the additive, it is generally about 0.1-about 50 wt %, preferably about 0.5-about 10 wt %, so as to maintain the binding force of the pharmaceutically active ingredient to the core, as well as to maintain the viscosity of the mixture to prevent decreased workability.

When the coating layer comprises a plurality of layers, the concentration of the pharmaceutical active ingredient in each layer may be changed successively or gradually by selecting the content of the water-soluble polymer or the viscosity grade of a mixture or by coating successively using mixtures which are different in the proportions of the pharmaceutical active ingredient and the other additives in the mixtures. In this case, coating may be performed using a mixture comprising the water-soluble polymer in an amount out of the range of about 0.1 to about 50% by weight, as long as coating layers in total contain about 0.1 to about 50% by weight of the water-soluble polymer. Further, the coating layer comprising a plurality of layers may comprise inert film layers formed by a known method so that the inert film layer can block each layer comprising the pharmaceutical active ingredient.

When two or more kinds of pharmaceutical active ingredient which are incompatible are used, the core may be coated with each mixture of each pharmaceutical active ingredient together or separately.

The coated core is dried, and then passed through a sieve to obtain a core granule having uniform particle size. The shape of the core granule usually corresponds to the core, and thus a nearly spherical composition can be obtained. As the sieve, for example, a No. 50 (300 μm) round sieve can be used. The core granule is obtained by selecting from particles which pass through the No. 50 round sieve.

The aforementioned fine granule is produced by coating a core granule with an enteric coating layer for the purpose of protecting the pharmaceutical active ingredient or imparting enteric dissolution, in accordance with the same manner as the aforementioned granulation method. If necessary, the fine granule may be further coated with a water-soluble sugar alcohol (preferably mannitol). When coated with a water-soluble sugar alcohol, the strength of an orally-disintegrating tablet comprising the fine granules is improved.

The enteric coating layer comprises, for example, a combination of the aqueous enteric polymer base, the sustained-release base, the plasticizer and the like as described above, and is preferably a layer having a thickness of about 20 to about 70 μm, preferably about 30 to about 50 μm and coating the whole surface of a composition comprising the pharmaceutical active ingredient. Therefore, when the particle diameter of the composition is smaller, the weight percent of the enteric coating layer in the whole fine granules is higher. In the fine granule of the present invention, the enteric coating layer is about 30 to about 70% by weight, preferably about 50 to about 70% by weight of the whole fine granules.

The enteric coating layer may be composed of a plurality of layers (e.g., 2 to 3 layers). An example of a coating method comprises coating a composition with an enteric coating layer comprising polyethylene glycol, with an enteric coating layer comprising triethyl citrate, and then with an enteric coating layer comprising polyethylene glycol.

The outermost layer of fine granules B may also be coated with a coating layer comprising a polymer affording a casting film having an elongation at break of about 100-about 700%, as in the case of fine granules A. The outermost layer can be coated with a coating layer comprising a polymer affording a casting film having an elongation at break of about 100-about 700% by a method similar to that for the aforementioned fine granules A.

The solid preparation (e.g. tablet) of the present invention can be produced in accordance with a conventional method in the pharmaceutical field.

Such methods include, for instance, a method which comprises blending the aforementioned fine granules (single fine granules, or 2-3 kinds of fine granules such as the aforementioned fine granules A and fine granules B and the like) and the "additives", and molding, if necessary followed by drying. Concretely mentioned is a method which comprises blending the fine granules and the additives, if necessary with water, and molding, if necessary followed by drying.

The "blending procedure" can be carried out by any of the conventional blending techniques such as admixing, kneading, granulating, etc. The above "blending procedure" is carried out, for instance, by using an apparatus such as Vertical Granulator GV10 (manufactured by Powrex Corporation), Universal Kneader (manufactured by Hata Iron Works Co., Ltd.), fluidized bed coater LAB-1 and FD-3S (manufactured by Powrex Corporation), V-shape mixer, tumbling mixer, and the like.

A production method by wet tabletting is preferably the method described in JP-A-5-271054 and the like. They may also be produced by drying after humidifying. The method is preferably the method described in JP-A-9-48726, JP-A-8-291051 and the like. That is, it is effective to enhance hardness by humidifying before or after tabletting and drying thereafter.

When the solid preparation is a tablet, for example, "molding" can be performed by punching at a pressure of about 0.5-about 3 ton/cm$^2$, preferably about 1-about 2 ton/cm$^2$ and using a single punch tableting machine (manufactured by KIKUSUI SEISAKUSHO LTD.), rotary tableting machine (manufactured by KIKUSUI SEISAKUSHO LTD.) and the like.

The "drying" may be performed by any method generally used for drying preparations, such as vacuum drying, fluidized bed drying and the like.

As the additive to be blended with fine granules, for example, water-soluble sugar alcohol, crystalline cellulose or L-HPC can be used. The orally-disintegrating solid perpetration for oral administration can be produced by further adding and mixing a binder, an acidulant, an effervescent agent, an artificial sweetener, a flavor, a lubricant, a colorant, a stabilizing agent, an excipient, a disintegrant, and the like, and then compression molding the mixture. Alternatively, a dispersion of the pharmaceutical active ingredient in water can be placed in a mold (e.g., PTP molded pocket), dried with a lyophilizer or a circulation dryer, and then heat-sealed to obtain a molded tablet.

The term "water-soluble sugar alcohol" means a sugar alcohol which requires less than 30 ml of water for dissolution within about 30 minutes when 1 g of the sugar alcohol is added to water and then strongly shaken at 20° C. for 30 seconds every 5 minutes.

Examples of the "water-soluble sugar alcohol" include mannitol, sorbitol, maltitol, a hydrogenated starch hydrolysate, xylitol, reduced palatinose, erythritol, and the like. Preferable examples of the "water-soluble sugar alcohol" include mannitol, xylitol and erythritol. The water-soluble sugar alcohol may be a mixture of two or more kinds of them at an appropriate ratio. Erythritol is conventionally produced by fermentation of glucose as a starting material with yeast or the like. In the present invention, erythritol having a particle size of 50 mesh or less is used. The erythritol is commercially available (Nikken Chemicals Co., Ltd., etc.).

The amount of the "water-soluble sugar alcohol" is usually about 3 to about 50 parts by weight, preferably about 5 to about 30 parts by weight based on 100 parts by weight of a total preparation.

The "crystalline cellulose" may be obtained by partial depolymerization of α-cellulose followed by purification. The "crystalline cellulose" also includes microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-591 (crystalline cellulose/carmellose sodium) and the like. Preferred is so-called high-compatible Avicel including Ceolus KG 801 and Ceolus KG 802. These crystalline celluloses may be used alone, or two or more kinds may be used in combination. These crystalline celluloses are commercially available (Asahi Kasei Corporation).

The crystalline cellulose may be incorporated in an amount of about 3 to about 50 parts by weight, preferably about 5 to about 40 parts by weight, most preferably about 5 to about 20 parts by weight into 100 parts by weight of a total preparation.

As the "low-substituted hydroxypropyl cellulose", LH-11, LH-21, LH-22, LH-B1, LH-31, LH-32, LH-33 and the like can be mentioned. These low-substituted hydroxypropyl celluloses can be obtained as commercially available products [manufactured by Shin-Etsu Chemical Co., Ltd.].

The low-substituted hydroxypropyl cellulose can be added in a proportion of about 1-about 50 parts by weight, preferably about 3-about 40 parts by weight, most preferably, about 3-about 20 parts by weight, per 100 parts by weight of the whole preparation.

The L-HPC having an HPC group content of 5.0-7.0 wt % or 7.0-9.9% to be used as an additive other than fine granules is added in a proportion of generally about 1-about 50 parts by weight, preferably about 1-about 40 parts by weight, more preferably about 1-about 20 parts by weight, per 100 parts by weight of the whole preparation, so as to afford sufficient disintegration property in the oral cavity and sufficient preparation strength.

Examples of the binder include hydroxypropyl cellulose, HPMC, crystalline cellulose, pregelatinized starch, polyvinylpyrrolidone, gum arabic powder, gelatin, pullulan, and the like. Two or more kinds of these binders may be used as a mixture at an appropriate ratio. When crystalline cellulose is used as the binder, a solid preparation having a higher strength and retaining an excellent orally rapidly disintegrating property can be obtained. The crystalline cellulose may be obtained by partial depolymerization of α-cellulose followed by purification. The "crystalline cellulose" also includes a cellulose referred to as microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-A591NF (crystalline cellulose/carmellose sodium), Avicel RC-591 (crystalline cellulose/carmellose sodium) and the like. Preferred is so-called high-compatible crystalline cellulose including Ceolus KG 801 and Ceolus KG 802. These crystalline celluloses may be used alone, or two or more kinds may be used in combination. These crystalline celluloses are commercially available (Asahi Kasei Corporation). In the case of a solid preparation not comprising fine granules, the crystalline cellulose is used in an amount of for example about 1 to about 50 parts by weight, preferably of about 2 to about 40 parts by weight, further preferably about 2 to about 20 parts by weight based on 100 parts by weight of the total preparation.

Examples of the acidulant include citric acid (anhydrous citric acid), tartaric acid, malic acid and the like.

Examples of the effervescent agent include sodium bicarbonate and the like.

Examples of the artificial sweetener include saccharine sodium, dipotassium glycyrrhizinate, aspartame, sucralose, acesulfame-K, stevia, thaumatin and the like.

The flavor may be synthetic or natural, and examples thereof include lemon, lemon lime, orange, menthol, strawberry and the like.

Examples of the lubricant include magnesium stearate, a sucrose fatty acid ester, polyethylene glycol, talc, stearic acid and the like. When polyethylene glycol is used as the lubricant, a stable solid preparation in which degradation with time of a pharmaceutically active ingredient is suppressed can be obtained. In this case, polyethylene glycol is used in an amount of for example about 0.01 to about 10 parts by weight, preferably about 0.1 to about 5 parts by weight based on 100 parts by weight of the total preparation.

Examples of the colorant include edible dyes such as food Yellow No. 5, food Red No. 2, and food Blue No. 2; an edible lake dye, ferric oxide and the like.

Examples of the stabilizing agent include a basic substance in the case of a basic pharmaceutically active ingredient, and an acidic substance in the case of an acidic pharmaceutically active ingredient.

Examples of the excipient include lactose, white sugar, D-mannitol (β-D-mannitol, etc.), starch, corn starch, crystalline cellulose, light anhydrous silicic acid, titanium oxide and the like.

Examples of the disintegrant include so-called super disintegrants such as crospovidone [manufactured by ISP Inc. (USA), or BASF (Germany)], croscarmellose sodium (FMC-Asahi Kasei Corporation) and carmellose calcium (GO-TOKU CHEMICAL COMPANY LTD.); hydroxypropyl cellulose, L-HPC; carboxymethyl starch sodium (Matsutani Chemical Industry Co., Ltd.); corn starch, and the like. Among them, crospovidone is preferably used. Two or more kinds of these disintegrants may be used as a mixture at an appropriate ratio.

The crospovidone may be any crosslinked polymer referred to as 1-ethenyl-2-pyrrolidinone homopolymer, including polyvinyl polypyrrolidone (PVPP) and 1-vinyl-2-pyrrolidinone homopolymers, and usually, the crospovidone having a molecular weight of 1,000,000 or more is used. Specific examples of commercially available crospovidone include crosslinked povidone, Kollidon CL [manufactured by BASF (Germany)], Polyplasdone XL, Polyplasdone XL-10, INF-10 [manufactured by ISP Inc. (USA)], polyvinylpyrrolidone, PVPP, 1-vinyl-2-pyrrolidinone homopolymers and the like.

These disintegrants may be used alone, or two or more kinds of them may be used in combination. For example, crospovidone may be used alone or in combination with other disintegrants.

The disintegrant is used in an amount of for example about 0.1 to about 20 parts by weight, preferably about 1 to about 10 parts by weight, further preferably about 3 to about 7 parts by weight based on 100 parts by weight of a total preparation.

Preferably, the preparation of the present invention does not contain an acid neutralizing agent.

Starting material powders and granules may be punched at room temperature, or may be heat tabletted at a temperature not lower than room temperature (about 25-about 40° C.). In the present specification, the "room temperature" refers to the temperature in the room where tabletting is performed in general tablet production, which is generally about 20-about 25° C.

The solid preparation of the present invention comprises fine granules preferably having an average granule size of about 500 μm or below, and the solid preparation can be produced by punching fine granules having an average granule size of about 500 μm or below.

The dosage form of the preparation of the present invention is preferably a tablet (an orally-disintegrating tablet, a disintegrating tablet in water). Particularly preferred is an orally rapidly disintegrating tablet.

Tablets such as orally-disintegrating tablet and the like has a diameter of about 6.5-about 20 mm, preferably about 8-about 14 mm, to facilitate handling for administration.

In the case of a preparation comprising two or more kinds (preferably 2-3 kinds) of fine granules having different release rates of the pharmaceutically active ingredient, the contents of each fine granules and other additives are not particularly limited as long as the size thereof permits easy ingestion.

The solid preparation of the present invention comprising (1) fine granules A showing controlled release of a pharmaceutically active ingredient, which are coated with a coating layer comprising a polymer affording a casting film having an elongation at break of about 100-about 700%, and (2) fine granules B with a different release rate of a pharmaceutically active ingredient from that of the fine granules of (1) may further comprise an additive. In this case, a preparation comprising about 10-about 50 wt % of fine granules A, about 10-about 30 wt % of fine granules B and about 20-about 80 wt % of an additive, relative to the whole preparation is preferable.

As the additive to be used for the aforementioned a solid preparation comprising fine granules A and fine granules B, those mentioned above can be mentioned. Particularly, a water-soluble sugar alcohol, a disintegrant and the like are preferably used. The definition, specific examples, content and the like of the water-soluble sugar alcohol and disintegrant are mentioned above.

The total weight of the solid preparation of the present invention is about 1000 mg or below, preferably about 300-about 900 mg, when 30 mg of a pharmaceutically active ingredient is contained.

The oral disintegration time (a time until a solid preparation is completely disintegrated with saliva alone in the oral cavity of a healthy adult man or woman) of the preparation of the present invention is usually within about 90 seconds, preferably within about 1 minute, more preferably about 5 to about 50 seconds, further preferably about 5 to about 40 seconds, particularly preferably about 5 to about 35 seconds.

The disintegration time in water of the preparation of the present invention is usually within about 90 seconds, preferably within about 1 minute, more preferably about 5 to about 40 seconds, further preferably about 5 to about 30 seconds, particularly preferably about 5 to about 25 seconds.

The strength (a value measured with a tablet hardness tester) of the preparation of the present invention is usually about 10 N to about 150 N (about 1 kg to about 15 kg).

The solid preparation of the present invention is administered without water or together with water. Examples of an administration method include (1) a method comprising holding the preparation of the present invention in the mouth and not swallowing the preparation as it is, and then dissolving or disintegrating the preparation with a small amount of water or with saliva in the oral cavity without water and (2) a method comprising swallowing a preparation as it is together with water. Alternatively, the tablet of the present invention may be dissolved or disintegrated with water, and then be administered.

A dose of the solid preparation varies depending on a pharmaceutically active ingredient, a subject to be administered, the kind of a disease and the like, and may be selected from such a range that the dose of a pharmaceutically active ingredient can be an effective amount.

For example, when the pharmaceutically active ingredient is lansoprazole, the solid preparation of the present invention is useful for treatment and prevention of a peptic ulcer (e.g., stomach ulcer, duodenal ulcer, anastomomic ulcer, Zollinger-Ellinson syndrome, etc.), gastritis, reflux esophagitis, symptomatic Gastroesophageal Reflex Disease (symptomatic GERD) and the like; elimination or assistance in elimination of *H. pylori*; suppression of upper gastrointestinal tract bleeding caused by peptic ulcer, acute stress ulcer or hemorrhagic gastritis; suppression of upper gastrointestinal tract bleeding caused by invasive stress (stress caused by major operation which requires central control after operation, or cerebrovascular disorder, head trauma, multiple organ failure or extensive burn which requires intensive care); treatment and prevention of an ulcer caused by a non-steroidal antiinflammatory agent; treatment and prevention of gastric hyperacidity and an ulcer caused by postoperative stress; administration before anesthesia and the like. The dose of the preparation is about 0.5 to about 1500 mg/day, preferably about 5 to about 500 mg/day, more preferably about 5 to about 150 mg/day per adult (60 kg body weight) of lansoprazole or optical isomers. Lansoprazole or an optically active form thereof may be used in combination with other pharmaceutical agents (antitumor agent, antibacterial agent etc.). Particularly, a combined use with an antibacterial agent selected from erythromycin antibiotics (e.g., clarithromycin etc.), penicillin antibiotics (e.g., amoxicillin etc.) and imidazole compounds (e.g., metronidazole etc.) affords a superior effect for eradication of *H. pylori*.

When a PPI such as lansoprazole, an optically active form thereof and the like is used as a pharmaceutically active ingredient for the preparation of the present invention, a preparation capable of controlled release to achieve an average pH in the stomach at 0.5 hr after dosing of not less than 4, and pH 4 or above maintained for 14 hours or longer is desirable.

The preparation of the present invention is, for example, a preparation comprising R-lansoprazole or a salt thereof as a pharmaceutically active ingredient, which reaches the maximum blood drug concentration in about 5 hours and maintains blood drug concentration of 100 ng/mL or above for about 4 hours or longer, when 30 mg of the pharmaceutically active ingredient is administered orally.

When the pharmaceutically active ingredient is voglibose, the preparation of the present invention is useful for the treatment and prophylaxis of obesity, adipositas, hyperlipemia, diabetes and the like, and the dose thereof is, as voglibose, about 0.01-about 30 mg/day, preferably about 0.01-about 10 mg/day, more preferably about 0.1-about 3 mg/day, for an adult (60 kg body weight). The tablet may be administered once a day or in 2-3 portions a day.

The present invention provides a method of suppressing breakage of fine granules showing controlled release of a pharmaceutically active ingredient, which are comprised in an orally-disintegrating tablet obtained by tabletting the fine granules and an additive, which method comprises, during production of the tablet, coating the fine granules with a coating layer comprising a polymer affording a casting film having an elongation at break of about 100-about 700%. According to this method, decreased masking effect of the bitter taste of the pharmaceutically active ingredient and decreased acid resistance due to the breakage of fine granules can be prevented.

EXAMPLES

The present invention is explained in detail in the following by referring to Production Examples, Examples, Comparative Examples and Experimental Examples, which are not to be construed as limitative.

The components used in the following Examples and Comparative Examples were the Japanese Pharmacopoeia 15th Edition compatible products. Unless otherwise specified, % used hereafter means wt %. In the following Examples and Comparative Examples, compound X is (R)-2-[[[3-methyl-4-(2,2,2-trifluoroethoxy)-2-pyridinyl]methyl]sulfinyl]-1H-benzimidazole. The properties of the tablets obtained in the Examples were measured by the following test methods.

(1) hardness Test
Tablet hardness was measured using a tablet hardness tester (manufactured by Toyama Sangyo Co., Ltd.). The test was run 10 times and the average thereof is shown.

(2) Disintegration Test in Oral Cavity
The time necessary for a tablet to be completely disintegrated in the oral cavity with saliva alone was measured. Four subjects performed the test and the average thereof is shown.

Production Example 1

Production of Fine Granules Coated with Pharmaceutically Active Ingredient

Core granules to be the core of controlled release fine granules A were produced as follows. Hypromellose (TC-5EW, 60 g) was dissolved in purified water (780 g), low-substituted hydroxypropyl cellulose (L-HPC-32, 30 g) and magnesium carbonate (60 g) were dispersed in this solution. Compound X (180 g) was uniformly dispersed in the obtained dispersion to give a coating solution. A predetermined amount (971 g) of the compound X-containing coating solution (1110 g) was applied to lactose-crystalline cellulose spheres (Nonpareil 105T, 150 g) using a rotary fluidized bed coater (SPIR-A-FLOW, manufactured by Freund Corporation). The coating conditions were: inlet temperature about 37° C., spray air pressure about 1 kgf/cm$^2$, exhaust air gauge 100, BED pressure about 250 mmHg, rotor speed about 300 rpm, spray rate about 3 g/min, spray gun position lower side. After the completion of coating, the obtained fine granules were dried in vacuo at 40° C. for 16 hr and passed through a round sieve to give core granules with a particle size of 150 μm-500 μm.

| [Composition of fine granules coated with pharmaceutically active ingredient (85 mg)] | |
|---|---|
| lactose-crystalline cellulose spheres (Nonpareil 105T) | 30 mg |
| compound X | 30 mg |
| magnesium carbonate | 10 mg |
| low-substituted hydroxypropyl cellulose | 5 mg |
| hypromellose | 10 mg |
| total | 85 mg |

Production Example 2

Production of Fine Granules Coated with Intermediate Layer

The pharmaceutically active ingredient-coated fine granules obtained in Production Example 1 was coated with an intermediate layer coating solution using a rotary fluidized bed coater (SPIR-A-FLOW, manufactured by Freund Corporation), and directly dried to give fine granules with the following composition. The intermediate layer coating solution was produced by dissolving hypromellose (TC-5EW, 39.5 g) and mannitol (39.5 g) in purified water (620.4 g), and dispersing titanium oxide (11.3 g), talc (16.9 g) and low-substituted hydroxypropyl cellulose (L-HPC-32, 28.2 g) in the obtained solution. A predetermined amount (661 g) of the intermediate layer coating solution (755.8 g) was applied to the fine granules coated with pharmaceutically active ingredient (400 g), which were obtained in Production Example 1, using a rotary fluidized bed coater (SPIR-A-FLOW, manufactured by Freund Corporation). The coating conditions were: inlet temperature about 60° C., spray air pressure about 1 kgf/cm$^2$, exhaust air gauge 100, BED pressure about 250 mmHg, rotor speed about 300 rpm, spray rate about 2.5 g/min, spray gun position lower side. After the completion of coating, the obtained fine granules were dried in vacuo at 40° C. for 16 hr and passed through a round sieve to give fine granules coated with intermediate layer with a particle size of 150 μm-500 μm.

| [Composition of fine granules coated with intermediate layer (110 mg)] | |
|---|---|
| fine granules coated with pharmaceutically active ingredient (Production Example 1) | 85 mg |
| hypromellose | 7 mg |
| low-substituted hydroxypropyl cellulose | 5 mg |
| talc | 3 mg |
| titanium oxide | 3 mg |
| mannitol | 7 mg |
| total | 110 mg |

Production Example 3

Production of Enteric Fine Granules

Methyl methacrylate-methacrylic acid copolymer (Eudragit S100, manufactured by Evonik Roehm) (184.8 g) and triethyl citrate (37.2 g) were dissolved in a mixture of purified water (283.2 g) and anhydrous ethanol (2545 g), and talc (92.4 g) was dispersed in the obtained solution to give a coating solution. A predetermined amount (2749 g) of the aforementioned coating solution (3142.6 g) was applied to the fine granules coated with intermediate layer (220 g), which were obtained in Production Example 2, using a rotary fluidized bed coater (SPIR-A-FLOW, manufactured by Freund Corporation). The coating conditions were: inlet temperature about 35° C., spray air pressure about 1 kgf/cm$^2$, exhaust air gauge 100, BED pressure about 250 mmHg, rotor speed about 300 rpm, spray rate about 2.0 g/min, spray gun position lower side. As a result, a controlled-release film which dissolves in a pH-dependent manner (pharmaceutically active ingredient is released in the environment of certain pH or above) was formed. The obtained fine granules were dried in vacuo at 40° C. for 16 hr and passed through a round sieve to give enteric fine granules with a particle size of 150 μm-500 μm.

| [Composition of enteric fine granules (240.9 mg)] | |
|---|---|
| fine granules coated with intermediate layer (Production Example 2) | 110 mg |
| methyl methacrylate-methacrylic acid copolymer | 77 mg |
| talc | 38.5 mg |
| triethyl citrate | 15.4 mg |
| total | 240.9 mg |

Production Example 4

Production of Polymer-Coated Fine Granules

Purified water (190 g) was heated to 80° C., and polysorbate 80 (1.84 g), glycerol monostearate (4.6 g) and triethyl citrate (4.6 g) were dispersed therein. The suspension was cooled to room temperature, and added to methacrylic acid-methyl acrylate-methyl methacrylate copolymer dispersion (Eudragit FS30D, manufactured by Evonik Roehm) (307 g) and uniformly mixed to give a coating solution. A predetermined amount (116 g) of the aforementioned coating solution (508.04 g) was applied to the enteric fine granules (200 g), which were obtained in Production Example 3, using a rotary fluidized bed coater (SPIR-A-FLOW, manufactured by Freund Corporation). The coating conditions were: inlet temperature about 32° C., spray air pressure about 1 kgf/cm$^2$, exhaust air gauge 100, BED pressure about 250 mmHg, rotor speed about 300 rpm, spray rate about 2.0 g/min, spray gun position lower side. The obtained fine granules were dried in vacuo at 40° C. for 16 hr and passed through a round sieve to give polymer-coated fine granules with a particle size of 150 μm-500 μm.

| [Composition of polymer-coated fine granules (267.87 mg)] | |
|---|---|
| enteric fine granules (Production Example 3) | 240.9 mg |
| methacrylic acid-methyl acrylate-methyl methacrylate copolymer | 24.09 mg |
| polysorbate 80 | 0.48 mg |
| glycerol monostearate | 1.2 mg |
| triethyl citrate | 1.2 mg |
| total | 267.87 mg |

Production Example 5

Production of Outer Layer Component-Granulated Powder

Mannitol (414 g), low-substituted hydroxypropyl cellulose (L-HPC-33, 60 g), crystalline cellulose (60 g) and crospovidone (30 g) were charged in a fluid bed granulator (LAB-1, manufactured by POWREX CORPORATION), and they were granulated while spraying an aqueous solution of mannitol (24 g) in purified water (136 g) and dried to give an outer layer component-granulated powder (573 g).

Example 1

Production of Orally-Disintegrating Solid Preparation

The polymer-coated fine granules (54.0 g) obtained in Production Example 4, the outer layer component-granulated powder (58.8 g) obtained in Production Example 5 and magnesium stearate (1.2 g) were mixed in a bag to give a mixed powder. The obtained mixed powder (114 g) was tabletted using Autograph (trade name, manufactured by SHIMADZU Corporation) (565.5 mg/tablet, a 13 mmϕ punch, flat-faced with beveled edge, tabletting pressure 20 kN/cm$^2$) to give the orally-disintegrating solid preparation (565.5 mg) containing compound X (30 mg) of the present invention.

Production Example 6

Production of Polymer-Coated Fine Granules

Purified water (190 g) was heated to 80° C., and polysorbate 80 (1.68 g), glycerol monostearate (4.2 g) and triethyl citrate (8.4 g) were dispersed therein. The suspension was cooled to room temperature, and added to methacrylic acid-methyl acrylate-methyl methacrylate copolymer dispersion (Eudragit FS30D, manufactured by Evonik Roehm) (280 g) and uniformly mixed to give a coating solution. A predetermined amount (121 g) of the aforementioned coating solution (484.28 g) was applied to the enteric fine granules (200 g), which were obtained in Production Example 3, using a rotary fluidized bed coater (SPIR-A-FLOW, manufactured by Freund Corporation). The coating conditions were: inlet temperature about 32° C., spray air pressure about 1 kgf/cm$^2$, exhaust air gauge 100, BED pressure about 250 mmHg, rotor speed about 300 rpm, spray rate about 2.0 g/min, spray gun position lower side. The obtained fine granules were dried in vacuo at 40° C. for 16 hr and passed through a round sieve to give polymer-coated fine granules with a particle size of 150 μm-500 μm.

| [Composition of polymer-coated fine granules (269.08 mg)] | |
|---|---|
| enteric fine granules (Production Example 3) | 240.9 mg |
| methacrylic acid-methyl acrylate-methyl methacrylate copolymer | 24.09 mg |
| polysorbate 80 | 0.48 mg |
| glycerol monostearate | 1.2 mg |
| triethyl citrate | 2.41 mg |
| total | 269.08 mg |

Example 2

Production of Orally-Disintegrating Solid Preparation

The polymer-coated fine granules (54.0 g) obtained in Production Example 6, the outer layer component-granulated powder (58.8 g) obtained in Production Example 5 and magnesium stearate (1.2 g) were mixed in a bag to give a mixed powder. The obtained mixed powder (568.0 mg) was tabletted using Autograph (trade name, manufactured by SHIMADZU Corporation) (568.0 mg/tablet, a 13 mmϕ punch, flat-faced with beveled edge, tabletting pressure 20 kN/cm$^2$) to give the orally-disintegrating solid preparation (568.0 mg) containing compound X (30 mg) of the present invention.

Production Example 7

Production of Fine Granules Coated with Pharmaceutically Active Ingredient

Core granules to be the core of controlled release fine granules B were produced as follows. Hydroxypropyl cellulose (HPC-L, 50 g) and mannitol (37.5 g) was dissolved in purified water (640 g), talc (37.5 g), low-substituted hydroxypropyl cellulose (L-HPC-32W, 25 g) and magnesium carbonate (50 g) were dispersed in this solution. Compound X (75 g) was uniformly dispersed in the obtained dispersion to give a coating solution. A predetermined amount (793 g) of the compound X-containing coating solution (915 g) was applied to lactose-crystalline cellulose spheres (Nonpareil 105T, 130 g) using a rotary fluidized bed coater (SPIR-A-FLOW, manufactured by Freund Corporation). The coating conditions were: inlet temperature about 40° C., spray air pressure about 1 kgf/cm$^2$, exhaust air gauge 100, BED pressure about 250 mmHg, rotor speed about 300 rpm, spray rate about 6 g/min, spray gun position lower side. After the completion of coating, the obtained fine granules were dried in vacuo at 40° C. for 16 hr and passed through a round sieve to give core granules with a particle size of 125 μm-500 μm.

| [Composition of fine granules coated with pharmaceutically active ingredient (85 mg)] | |
| --- | --- |
| lactose-crystalline cellulose spheres (Nonpareil 105T) | 30 mg |
| compound X | 15 mg |
| mannitol | 7.5 mg |
| talc | 7.5 mg |
| magnesium carbonate | 10 mg |
| low-substituted hydroxypropyl cellulose | 5 mg |
| hydroxypropyl cellulose | 10 mg |
| total | 85 mg |

Production Example 8

Production of Fine Granules Coated with Intermediate Layer

The pharmaceutically active ingredient-coated fine granules obtained in Production Example 7 was coated with an intermediate layer coating solution using a rotary fluidized bed coater (SPIR-A-FLOW, manufactured by Freund Corporation), and directly dried to give fine granules with the following composition. The intermediate layer coating solution was produced by dissolving hypromellose (substitution type 2910, 16.8 g) and mannitol (16.8 g) in purified water (540 g), and dispersing titanium oxide (7.2 g), talc (7.2 g) and low-substituted hydroxypropyl cellulose (L-HPC-32W, 12 g) in the obtained solution. A predetermined amount (500 g) of the intermediate layer coating solution (600 g) was applied to the fine granules coated with pharmaceutically active ingredient (170 g), which were obtained in Production Example 7, using a rotary fluidized bed coater (SPIR-A-FLOW, manufactured by Freund Corporation). The coating conditions were: inlet temperature about 60° C., spray air pressure about 1 kgf/cm$^2$, exhaust air gauge 100, BED pressure about 250 mmHg, rotor speed about 300 rpm, spray rate about 2.5 g/min, spray gun position lower side. After the completion of coating, the obtained fine granules were dried in vacuo at 40° C. for 16 hr and passed through a round sieve to give fine granules coated with intermediate layer with a particle size of 125 μm-500 μm.

| [Composition of fine granules coated with intermediate layer (110 mg)] | |
| --- | --- |
| fine granules coated with pharmaceutically active ingredient (Production Example 7) | 85 mg |
| hypromellose | 7 mg |
| low-substituted hydroxypropyl cellulose | 5 mg |
| talc | 3 mg |
| titanium oxide | 3 mg |
| mannitol | 7 mg |
| total | 110 mg |

Production Example 9

Production of Enteric Fine Granules

Glycerol monostearate (2.4 g), polysorbate 80 (0.72 g) and ferric oxide (0.05 g) were added to purified water (73.7 g), and the mixture was heated in a homomixer (T.K. AUTOHOMO-MIXER, manufactured by Tokushu Kika Kogyo) to 70° C., and cooled to room temperature to give a glycerol monostearate emulsion. Macrogol 6000 (4.08 g) and citric acid (0.05 g) were dissolved in purified water (50 g), and methacrylic acid-ethyl acrylate copolymer dispersion (Eudragit L30D-55, manufactured by Evonik Roehm) (122.08 g) and methyl methacrylate-ethyl acrylate copolymer dispersion (Eudragit NE30D, manufactured by Evonik Roehm) (13.6 g) were added. A glycerol monostearate emulsion was added to the obtained solution to give a coating solution. A predetermined amount (111.1 g) of the aforementioned coating solution (266.68 g) was applied to the fine granules coated with intermediate layer (110 g), which were obtained in Production Example 8, using a rotary fluidized bed coater (SPIR-A-FLOW, manufactured by Freund Corporation). The coating conditions were: inlet temperature about 35° C., spray air pressure about 1 kgf/cm$^2$, exhaust air gauge 100, BED pressure about 250 mmHg, rotor speed about 150 rpm, spray rate about 2.0 g/min, spray gun position lower side. As a result, a controlled-release film was formed. The obtained fine granules were dried in vacuo at 40° C. for 16 hr and passed through a round sieve to give enteric fine granules with a particle size of 125 μm-500 μm.

| [Composition of enteric fine granules (130 mg)] | |
| --- | --- |
| fine granules coated with intermediate layer (Production Example 8) | 110 mg |
| methacrylic acid-ethyl acrylate copolymer | 15.26 mg |
| methyl methacrylate-ethyl acrylate copolymer | 1.7 mg |
| macrogol 6000 | 1.7 mg |
| glycerol monostearate | 1.0 mg |
| polysorbate 80 | 0.3 mg |
| citric acid | 0.02 mg |
| ferric oxide | 0.02 mg |
| total | 130 mg |

Production Example 10

Production of Enteric Fine Granules

Glycerol monostearate (14.4 g), polysorbate 80 (4.32 g) and ferric oxide (0.29 g) were added to purified water (470 g), and the mixture was heated in a homomixer (T.K. AUTO-HOMOMIXER, manufactured by Tokushu Kika Kogyo) to 70° C., and cooled to room temperature to give a glycerol monostearate emulsion. Triethyl citrate (44.88 g) and citric acid (0.12 g) were dissolved in purified water (319.4 g), and methacrylic acid-ethyl acrylate copolymer dispersion (Eudragit L30D-55, manufactured by Evonik Roehm) (672 g) and methyl methacrylate-ethyl acrylate copolymer dispersion (Eudragit NE30D, manufactured by Evonik Roehm) (74.64 g) were added. A glycerol monostearate emulsion was added to the obtained solution to give a coating solution. A predetermined amount (666.7 g) of the aforementioned coating solution (1600.05 g) was applied to the enteric fine granules (130 g), which were obtained in Production Example 9, using a rotary fluidized bed coater (SPIR-A-FLOW, manufactured by Freund Corporation). The coating conditions were: inlet temperature about 35° C., spray air pressure about 1 kgf/cm$^2$, exhaust air gauge 100, BED pressure about 250 mmHg, rotor speed about 150 rpm, spray rate about 2.0 g/min, spray gun position lower side. As a result, a controlled-release film was formed. The obtained fine granules were dried in vacuo at 40° C. for 16 hr and passed through a round sieve to give enteric fine granules with a particle size of 125 μm-500 μm.

| [Composition of enteric fine granules (250 mg)] | |
| --- | --- |
| enteric fine granules (Production Example 9) | 130 mg |
| methacrylic acid-ethyl acrylate copolymer | 84 mg |
| methyl methacrylate-ethyl acrylate copolymer | 9.33 mg |
| triethyl citrate | 18.7 mg |
| glycerol monostearate | 6.0 mg |
| polysorbate 80 | 1.8 mg |
| citric acid | 0.05 mg |
| ferric oxide | 0.12 mg |
| total | 250 mg |

Production Example 11

Production of Enteric Fine Granules

Glycerol monostearate (1.2 g), polysorbate 80 (0.36 g) and ferric oxide (0.02 g) were added to purified water (36.8 g), and the mixture was heated in a homomixer (T.K. AUTOHOMO-MIXER, manufactured by Tokushu Kika Kogyo) to 70° C., and cooled to room temperature to give a glycerol monostearate emulsion. Macrogol 6000 (2.04 g) and citric acid (0.02 g) were dissolved in purified water (25 g), and methacrylic acid-ethyl acrylate copolymer dispersion (Eudragit L30D-55, manufactured by Evonik Roehm) (61.04 g) and methyl methacrylate-ethyl acrylate copolymer dispersion (Eudragit NE30D, manufactured by Evonik Roehm) (6.8 g) were added. A glycerol monostearate emulsion was added to the obtained solution to give a coating solution. A predetermined amount (55.53 g) of the aforementioned coating solution (133.28 g) was applied to the enteric fine granules (250 g), which were obtained in Production Example 10, using a rotary fluidized bed coater (SPIR-A-FLOW, manufactured by Freund Corporation). The coating conditions were: inlet temperature about 35° C., spray air pressure about 1 kgf/cm$^2$, exhaust air gauge 100, BED pressure about 250 mmHg, rotor speed about 150 rpm, spray rate about 2.0 g/min, spray gun position lower side. As a result, a controlled-release film was formed. The obtained fine granules were dried in vacuo at 40° C. for 16 hr and passed through a round sieve to give enteric fine granules with a particle size of 125 μm-500 μm.

| [Composition of enteric fine granules (260 mg)] | |
| --- | --- |
| enteric fine granules (Production Example 10) | 250 mg |
| methacrylic acid-ethyl acrylate copolymer | 7.63 mg |
| methyl methacrylate-ethyl acrylate copolymer | 0.85 mg |
| macrogol 6000 | 0.85 mg |
| glycerol monostearate | 0.5 mg |
| polysorbate 80 | 0.15 mg |
| citric acid | 0.01 mg |
| ferric oxide | 0.01 mg |
| total | 260 mg |

Production Example 12

Production of Mannitol-Overcoated Enteric Fine Granules

Mannitol (24 g) was dissolved in purified water (216 g) to give a coating solution. A predetermined amount (100 g) of the aforementioned coating solution (240 g) was applied to the enteric fine granules (260 g), which were obtained in Production Example 11, using a rotary fluidized bed coater (SPIR-A-FLOW, manufactured by Freund Corporation). The coating conditions were: inlet temperature about 40° C., spray air pressure about 1 kgf/cm$^2$, exhaust air gauge 100, BED pressure about 250 mmHg, rotor speed about 150 rpm, spray rate about 3.0 g/min, spray gun position lower side. Mannitol was overcoated. The obtained fine granules were dried in vacuo at 40° C. for 16 hr and passed through a round sieve to give the outermost layer-coated fine granules with a particle size of 125 μm-500 μm.

| [Composition of mannitol-overcoated enteric fine granules (270 mg)] | |
| --- | --- |
| enteric fine granules (Production Example 11) | 260 mg |
| mannitol | 10 mg |
| total | 270 mg |

Production Example 13

Production of Outer Layer Component-Granulated Powder

Mannitol (401 g), low-substituted hydroxypropyl cellulose (L-HPC-33, 60 g), crystalline cellulose (60 g) and crospovidone (30 g), anhydrous citric acid (6 g), aspartame (6 g) and flavor (STRAWBERRY DURAROME, Nihon Firmenich K.K.) (0.9 g) were charged in a fluid bed granulator (LAB-1, manufactured by POWREX CORPORATION), and they were granulated while spraying an aqueous solution of mannitol (24 g) in purified water (136 g) and dried to give an outer layer powder (588 g). Magnesium stearate (12 g) was further added, and the mixture was mixed in a bag to give an outer layer component-granulated powder (600 g).

Example 3

Production of Orally-Disintegrating Solid Preparation

The polymer-coated fine granules (200.9 g) obtained in Production Example 4, the enteric fine granules (135 g) obtained in Production Example 12 and the outer layer component-granulated powder (373.2 g) obtained in Production Example 13 were mixed in a bag to give a mixed powder. A predetermined amount (350 g) of the obtained mixed powder (709.1 g) was tabletted using a rotary tabletting machine (Correct 19K AWC) (709.1 mg/tablet, a 13 mmϕ punch, flat-faced with beveled edge, tabletting pressure 20 kN) to give the orally-disintegrating solid preparation (709.1 mg) containing compound X (30 mg) of the present invention.

Example 4

Production of Orally-Disintegrating Solid Preparation

The polymer-coated fine granules (201.8 g) obtained in Production Example 6, the enteric fine granules (135 g) obtained in Production Example 12 and the outer layer component-granulated powder (374.3 g) obtained in Production Example 13 were mixed in a bag to give a mixed powder. A predetermined amount (350 g) of the obtained mixed powder (711.1 g) was tabletted using a rotary tabletting machine (Correct 19K AWC) (711.1 mg/tablet, a 13 mmϕ punch, flat-faced with beveled edge, tabletting pressure 20 kN) to give the orally-disintegrating solid preparation (711.1 mg) containing compound X (30 mg) of the present invention.

Comparative Example 1

Production of Orally-Disintegrating Solid Preparation

The enteric fine granules (54.0 g) obtained in Production Example 3, the outer layer component-granulated powder (58.8 g) obtained in Production Example 5 and magnesium stearate (1.2 g) were mixed in a bag to give a mixed powder. The obtained mixed powder (114 g) was tabletted using Autograph (trade name, manufactured by SHIMADZU Corporation) (508.7 mg/tablet, a 13 mmϕ punch, flat-faced with beveled edge, tabletting pressure 20 kN/cm$^2$) to give the orally-disintegrating solid preparation (508.7 mg) containing compound X (30 mg).

Comparative Example 2

Production of Capsule Preparation of Enteric Fine Granules

The enteric fine granules (240.9 mg) obtained in Production Example 3 were filled in a HPMC capsule to give a capsule containing 30 mg of compound X per capsule.

Experimental Example 1

The hardness of the tablets obtained in Comparative Example 1, Example 1 and Example 2 was measured by a tablet hardness tester (manufactured by Toyama Sangyo Co., Ltd.). According to the Japanese Pharmacopoeia dissolution test, Method 2, a dissolution test was performed using 0.1N HCl (500 mL) at 100 rpm for 2 hr. The eluates were recovered and filtered through a 0.45 μm membrane filter. The absorbance was measured and the drug dissolution rate in 0.1N HCl was calculated. The results are shown below. The hardness test was performed 6 times and the dissolution test was performed 2 times, and the average values are shown.

TABLE 1

| preparation | hardness (N) | dissolution rate (%) |
|---|---|---|
| Comparative Example 1 | 33 | 9.7 |
| Example 1 | 57 | 3.7 |
| Example 2 | 64 | 1.8 |

As is clear from Table 1, the tablets of Example 1 and Example 2 showed sufficiently high tablet hardness as compared to the tablet of Comparative Example 1, and the dissolution rate was low. Therefore, it was confirmed that the tablet hardness and acid resistance after tabletting were improved by coating the enteric fine granules with a coating layer containing a polymer.

Experimental Example 2

The capsule obtained in Comparative Example 2, and the tablets obtained in Example 1 and Example 2 were orally administered to fasted beagle dogs at a dose of 30 mg (amount equivalent to compound X). After administration, the concentration of compound X in plasma was measured at 1 hr, 2 hr, 4 hr, 6 hr, 8 hr, 10 hr and 12 hr later, and the area under the blood concentration-time curve [AUC (μg·h/mL)] was calculated by the trapezium rule. In addition, the maximum blood concentration [Cmax (μg/mL)] and time-to-maximum blood concentration [Tmax (h)] were also measured. The results are shown below. In the Table, the values show average value±SD.

TABLE 2

| preparation | AUC (μg · h/mL) | Cmax (μg/mL) | Tmax (h) |
|---|---|---|---|
| Comparative Example 2 | 3.645 ± 0.180 | 1.328 ± 0.276 | 3.5 ± 1.0 |
| Example 1 | 2.661 ± 1.144 | 0.959 ± 0.383 | 3.5 ± 1.0 |
| Example 2 | 3.097 ± 1.285 | 1.097 ± 0.514 | 4.0 ± 0.0 |

As is clear from Table 2, the absorbability of the tablets of Example 1 and Example 2 did not decrease markedly, as compared to the capsule of Comparative Example 2.

From the results of Experimental Example 1 and Experimental Example 2, it was confirmed that the tablet hardness and acid resistance after tabletting were improved, without marked decrease in the absorbability after oral administration, by coating the enteric fine granules with a coating layer containing a polymer.

Production Example 14

Production of Fine Granules Coated with Pharmaceutically Active Ingredient

Core granules to be the core of controlled release fine granules A were produced as follows. Hydroxypropyl cellulose (HPC-SL-T, 360 g) was dissolved in purified water (4680 g), low-substituted hydroxypropyl cellulose (L-HPC-32, 180 g) and magnesium carbonate (360 g) were dispersed in this solution. Compound X (1080 g) was uniformly dispersed in the obtained dispersion to give a coating solution. A predetermined amount (5550 g) of the compound X-containing coating solution (6660 g) was applied to lactose-crystalline cellulose spheres (Nonpareil 105T, 945 g) using a rotary fluidized bed coater (MP-10 TOKU-2 type, manufactured by POWREX CORPORATION). The coating conditions were: inlet air temperature about 85° C., product temperature about 31° C., spray air volume about 80 NL/min, rotor speed about 500 rpm, spray rate about 17 g/min, spray gun position tangential. After the completion of coating, the obtained fine granules were dried for about 50 min to give core granules (2550 g).

| [Composition of fine granules coated with pharmaceutically active ingredient (85 mg)] | |
| --- | --- |
| lactose-crystalline cellulose spheres (Nonpareil 105T) | 30 mg |
| compound X | 30 mg |
| magnesium carbonate | 10 mg |
| low-substituted hydroxypropyl cellulose | 5 mg |
| hydroxypropyl cellulose | 10 mg |
| total | 85 mg |

Production Example 15

Production of Fine Granules Coated with Intermediate Layer

The pharmaceutically active ingredient-coated fine granules obtained in Production Example 14 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5EW, 252 g) and mannitol (252 g) in purified water (3960 g), and dispersing titanium oxide (108 g), talc (108 g) and low-substituted hydroxypropyl cellulose (L-HPC-32, 180 g) in the obtained solution. A predetermined amount (4050 g) of the intermediate layer coating solution (4860 g) was applied to the fine granules coated with pharmaceutically active ingredient (2550 g), which were obtained in Production Example 14, using a rotary fluidized bed coater (MP-10 TOKU-2 type, manufactured by POWREX CORPORA-TION). The coating conditions were: inlet air temperature about 85° C., product temperature about 41° C., spray air volume about 100 NL/min, rotor speed about 550 rpm, spray rate about 16 g/min, spray gun position tangential. After the completion of coating, the obtained fine granules were dried for about 30 min and passed through a round sieve to give fine granules coated with intermediate layer with a particle size of 150 µm-355 µm.

| [Composition of fine granules coated with intermediate layer (110 mg)] | |
| --- | --- |
| fine granules coated with pharmaceutically active ingredient (Production Example 14) | 85 mg |
| hypromellose | 7 mg |
| low-substituted hydroxypropyl cellulose | 5 mg |
| talc | 3 mg |
| titanium oxide | 3 mg |
| mannitol | 7 mg |
| total | 110 mg |

Production Example 16

Production of Enteric Fine Granules

Methyl methacrylate-methacrylic acid copolymer (Eudragit S100, manufactured by Evonik Roehm) (832 g) and triethyl citrate (166 g) were dissolved in a mixture of purified water (1272 g) and anhydrous ethanol (11451 g), and talc (416 g) was dispersed in the obtained solution to give a coating solution. A predetermined amount (12370 g) of the aforementioned coating solution (14137 g) was applied to the fine granules coated with intermediate layer (990 g), which were obtained in Production Example 15, using a rotary fluidized bed coater (MP-10 TOKU-2 type, manufactured by POWREX CORPORATION). The coating conditions were: inlet air temperature about 55° C., product temperature about 30° C., spray air volume about 100 NL/min, rotor speed about 600 rpm, spray rate about 18 g/min, spray gun position tangential. As a result, a controlled-release film which dissolves in a pH-dependent manner (pharmaceutically active ingredient is released in the environment of certain pH or above) was formed. The obtained fine granules were dried in vacuo at 40° C. for 16 hr and passed through a round sieve to give enteric fine granules with a particle size of 250 µm-425 µm.

| [Composition of enteric fine granules (240.9 mg)] | |
| --- | --- |
| fine granules coated with intermediate layer (Production Example 15) | 110 mg |
| methyl methacrylate-methacrylic acid copolymer | 77 mg |
| talc | 38.5 mg |
| triethyl citrate | 15.4 mg |
| total | 240.9 mg |

Production Example 17

Production of Polymer-Coated Fine Granules

Purified water (587.5 g) was heated to 80° C., and polysorbate 80 (5.18 g), glycerol monostearate (12.96 g) and triethyl citrate (12.96 g) were dispersed therein. The suspension was cooled to room temperature, and added to methacrylic acid-methyl acrylate-methyl methacrylate copolymer dispersion (Eudragit FS30D, manufactured by Evonik Roehm) (867.2 g) and uniformly mixed to give a coating solution. A predetermined amount (624 g) of the aforementioned coating solution (1485.8 g) was applied to the enteric fine granules (1040 g), which were obtained in Production Example 16, using a rotary fluidized bed coater (MP-10 TOKU-2 type, manufactured by POWREX CORPORATION). The coating conditions were: inlet air temperature about 60° C., product temperature about 26° C., spray air volume about 120 NL/min, rotor speed about 550 rpm, spray rate about 9 g/min, spray gun position tangential. After the completion of coating, polymer-coated fine granules (1156 g) were obtained.

| [Composition of polymer-coated fine granules (267.87 mg)] | |
| --- | --- |
| enteric fine granules (Production Example 16) | 240.9 mg |
| methacrylic acid-methyl acrylate-methyl methacrylate copolymer | 24.09 mg |
| polysorbate 80 | 0.48 mg |

-continued

[Composition of polymer-coated fine granules (267.87 mg)]

| | |
|---|---|
| glycerol monostearate | 1.2 mg |
| triethyl citrate | 1.2 mg |
| total | 267.87 mg |

Production Example 18

Production of Mannitol Coated Fine Granules

Mannitol (108 g) was dissolved in purified water (648 g) to give a coating solution. A predetermined amount (302 g) of the aforementioned coating solution (756 g) was applied to the polymer-coated fine granules (1156 g), which were obtained in Production Example 17, using a rotary fluidized bed coater (MP-10 TOKU-2 type, manufactured by POWREX CORPORATION). The coating conditions were: inlet air temperature about 85° C., product temperature about 34° C., spray air volume about 120 NL/min, rotor speed about 550 rpm, spray rate about 12 g/min, spray gun position tangential. After the completion of coating, the obtained fine granules were dried for about 2 min and passed through a round sieve to give mannitol-coated fine granules with a particle size of 250 μm-425 μm.

[Composition of mannitol-coated fine granules (277.9 mg)]

| | |
|---|---|
| polymer-coated fine granules (Production Example 17) | 267.9 mg |
| mannitol | 10.0 mg |
| total | 277.9 mg |

Production Example 19

Production of Fine Granules Coated with Intermediate Layer

The pharmaceutically active ingredient-coated fine granules obtained in Production Example 14 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5EW, 504 g) and mannitol (504 g) in purified water (5400 g), and dispersing titanium oxide (216 g), talc (216 g) and low-substituted hydroxypropyl cellulose (L-HPC-32, 360 g) in the obtained solution. A predetermined amount (6000 g) of the intermediate layer coating solution (7200 g) was applied to the fine granules coated with pharmaceutically active ingredient (2550 g), which were obtained in Production Example 14, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 17 g/min, spray gun position tangential. After the completion of coating, the obtained fine granules were dried for 30 min and passed through a round sieve to give fine granules coated with intermediate layer with a particle size of 150 μm-355 μm.

[Composition of fine granules coated with intermediate layer (135 mg)]

| | |
|---|---|
| fine granules coated with pharmaceutically active ingredient (Production Example 14) | 85 mg |
| hypromellose | 14 mg |
| low-substituted hydroxypropyl cellulose | 10 mg |
| talc | 6 mg |
| titanium oxide | 6 mg |
| mannitol | 14 mg |
| total | 135 mg |

Production Example 20

Production of Polymer-Coated Fine Granules

Purified water (1881.8 g) was heated to 80° C., and polysorbate 80 (17.5 g), glycerol monostearate (43.74 g), triethyl citrate (43.74 g), yellow ferric oxide (0.49 g) and ferric oxide (0.49 g) were dispersed therein. The suspension was cooled to room temperature, added to mixed dispersion (2916 g) of methacrylic acid-methyl acrylate-methyl methacrylate copolymer dispersion (Eudragit FS30D, manufactured by Evonik Roehm) (2857.68 g) and methacrylic acid-ethyl acrylate copolymer dispersion (Eudragit L30D-55, manufactured by Evonik Roehm) (58.32 g), and uniformly mixed to give a coating solution. A predetermined amount (4291 g) of the aforementioned coating solution (4903.76 g) was applied to the fine granules coated with intermediate layer (1215 g), which were obtained in Production Example 19, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (2032 g) were obtained.

[Composition of polymer-coated fine granules (225.81 mg)]

| | |
|---|---|
| fine granules coated with intermediate layer (Production Example 19) | 135 mg |
| methacrylic acid-methyl acrylate-methyl methacrylate copolymer | 79.38 mg |
| methacrylic acid-ethyl acrylate copolymer | 1.62 mg |
| polysorbate 80 | 1.62 mg |
| glycerol monostearate | 4.05 mg |
| triethyl citrate | 4.05 mg |
| yellow ferric oxide | 0.045 mg |
| ferric oxide | 0.045 mg |
| total | 225.81 mg |

Production Example 21

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (2032 g), which were obtained in Production Example 20, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 3 min and passed through a round sieve to give mannitol-coated fine granules with a particle size of 250 μm-425 μm.

| [Composition of mannitol-coated fine granules (235.8 mg)] | |
|---|---|
| polymer-coated fine granules (Production Example 20) | 225.8 mg |
| mannitol | 10.0 mg |
| total | 235.8 mg |

Production Example 22

Production of Polymer-Coated Fine Granules

Purified water (1881.8 g) was heated to 80° C., and polysorbate 80 (17.5 g), glycerol monostearate (43.74 g) and triethyl citrate (43.74 g), yellow ferric oxide (0.49 g) and ferric oxide (0.49 g) were dispersed therein. The suspension was cooled to room temperature, and added to methacrylic acid-methyl acrylate-methyl methacrylate copolymer dispersion (Eudragit FS30D, manufactured by Evonik Roehm) (2916 g) and uniformly mixed to give a coating solution. A predetermined amount (4291 g) of the aforementioned coating solution (4903.76 g) was applied to the fine granules coated with intermediate layer (1215 g), which were obtained in Production Example 19, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (2032 g) were obtained.

| [Composition of polymer-coated fine granules (225.81 mg)] | |
|---|---|
| fine granules coated with intermediate layer (Production Example 19) | 135 mg |
| methacrylic acid-methyl acrylate-methyl methacrylate copolymer | 81 mg |
| polysorbate 80 | 1.62 mg |
| glycerol monostearate | 4.05 mg |
| triethyl citrate | 4.05 mg |
| yellow ferric oxide | 0.045 mg |
| ferric oxide | 0.045 mg |
| total | 225.81 mg |

Production Example 23

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (2032 g), which were obtained in Production Example 22, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 3 min and passed through a round sieve to give mannitol-coated fine granules with a particle size of 250 μm-425 μm.

| [Composition of mannitol-coated fine granules (235.8 mg)] | |
|---|---|
| polymer-coated fine granules (Production Example 22) | 225.8 mg |
| mannitol | 10.0 mg |
| total | 235.8 mg |

Production Example 24

Production of Polymer-Coated Fine Granules

Purified water (1028.4 g) was heated to 80° C., and polysorbate 80 (8.75 g), glycerol monostearate (21.87 g) and triethyl citrate (43.74 g), yellow ferric oxide (0.256 g) and ferric oxide (0.256 g) were dispersed therein. The suspension was cooled to room temperature, and added to methacrylic acid-methyl acrylate-methyl methacrylate copolymer dispersion (Eudragit FS30D, manufactured by Evonik Roehm) (1458 g) and uniformly mixed to give a coating solution. A predetermined amount (2241 g) of the aforementioned coating solution (2561.272 g) was applied to the fine granules coated with intermediate layer (1215 g), which were obtained in Production Example 19, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1642 g) were obtained.

| [Composition of polymer-coated fine granules (182.4324 mg)] | |
|---|---|
| fine granules coated with intermediate layer (Production Example 19) | 135 mg |
| methacrylic acid-methyl acrylate-methyl methacrylate copolymer | 40.5 mg |
| polysorbate 80 | 0.81 mg |
| glycerol monostearate | 2.025 mg |
| triethyl citrate | 4.05 mg |
| yellow ferric oxide | 0.0237 mg |
| ferric oxide | 0.0237 mg |
| total | 182.4324 mg |

Production Example 25

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (1642 g), which were obtained in Production Example 24, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 3 min and passed through a round sieve to give mannitol-coated fine granules with a particle size of 250 µm-425 µm.

| [Composition of mannitol-coated fine granules (192.4 mg)] | |
|---|---|
| polymer-coated fine granules (Production Example 24) | 182.4 mg |
| mannitol | 10.0 mg |
| total | 192.4 mg |

Production Example 26

Production of Polymer-Coated Fine Granules

Purified water (1714.1 g) was heated to 80° C., and polysorbate 80 (14.58 g), glycerol monostearate (36.45 g), triethyl citrate (72.9 g), yellow ferric oxide (0.427 g) and ferric oxide (0.427 g) were dispersed therein. The suspension was cooled to room temperature, and added to methacrylic acid-methyl acrylate-methyl methacrylate copolymer dispersion (Eudragit FS30D, manufactured by Evonik Roehm) (2430 g) and uniformly mixed to give a coating solution. A predetermined amount (3735 g) of the aforementioned coating solution (4268.884 g) was applied to the fine granules coated with intermediate layer (1215 g), which were obtained in Production Example 19, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1926 g) were obtained.

| [Composition of polymer-coated fine granules (214.054 mg)] | |
|---|---|
| fine granules coated with intermediate layer (Production Example 19) | 135 mg |
| methacrylic acid-methyl acrylate-methyl methacrylate copolymer | 67.5 mg |
| polysorbate 80 | 1.35 mg |
| glycerol monostearate | 3.375 mg |
| triethyl citrate | 6.75 mg |
| yellow ferric oxide | 0.0395 mg |
| ferric oxide | 0.0395 mg |
| total | 214.054 mg |

Production Example 27

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (1926 g), which were obtained in Production Example 26, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for 3 min and passed through a round sieve to give mannitol-coated fine granules with a particle size of 250 µm-425 µm.

| [Composition of mannitol-coated fine granules (224.1 mg)] | |
|---|---|
| polymer-coated fine granules (Production Example 26) | 214.1 mg |
| mannitol | 10.0 mg |
| total | 224.1 mg |

Production Example 28

Production of Fine Granules Coated with Pharmaceutically Active Ingredient

Core granules to be the core of controlled release fine granules B were produced as follows. Hydroxypropyl cellulose (HPC-SL-T, 360 g) and mannitol (270 g) were dissolved in purified water (4680 g), talc (270 g), low-substituted hydroxypropyl cellulose (L-HPC-32, 180 g) and magnesium carbonate (360 g) were dispersed in this solution. Compound X (540 g) was uniformly dispersed in the obtained dispersion to give a coating solution. A predetermined amount (5550 g) of the compound X-containing coating solution (6660 g) was applied to lactose-crystalline cellulose spheres (Nonpareil 105T, 945 g) using a rotary fluidized bed coater (MP-10 TOKU-2 type, manufactured by POWREX CORPORATION). The coating conditions were: inlet air temperature about 85° C., product temperature about 31° C., spray air volume about 80 NL/min, rotor speed about 500 rpm, spray rate about 14 g/min, spray gun position tangential. After the completion of coating, core granules (2550 g) were obtained.

| [Composition of fine granules coated with pharmaceutically active ingredient (85 mg)] | |
|---|---|
| lactose-crystalline cellulose spheres (Nonpareil 105T) | 30 mg |
| compound X | 15 mg |
| mannitol | 7.5 mg |
| talc | 7.5 mg |
| magnesium carbonate | 10 mg |
| low-substituted hydroxypropyl cellulose | 5 mg |
| hydroxypropyl cellulose | 10 mg |
| total | 85 mg |

Production Example 29

Production of Fine Granules Coated with Intermediate Layer

The pharmaceutically active ingredient-coated fine granules obtained in Production Example 28 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5EW, 504 g) and mannitol (504 g) in purified water (5400 g), and dispersing titanium oxide (216 g), talc (216 g) and low-substituted hydroxypropyl cellulose (L-HPC-32, 360 g) in the obtained solution. A predetermined amount (6000 g) of the intermediate layer coating solution (7200 g)

was applied to the fine granules coated with pharmaceutically active ingredient (2550 g), which were obtained in Production Example 28, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 17 g/min, spray gun position tangential. After the completion of coating, the obtained fine granules were dried for about 30 min and passed through a round sieve to give fine granules coated with intermediate layer with a particle size of 150 μm-355 μm.

| [Composition of fine granules coated with intermediate layer (135 mg)] | |
|---|---|
| fine granules coated with pharmaceutically active ingredient (Production Example 28) | 85 mg |
| hypromellose | 14 mg |
| low-substituted hydroxypropyl cellulose | 10 mg |
| talc | 6 mg |
| titanium oxide | 6 mg |
| mannitol | 14 mg |
| total | 135 mg |

Production Example 30

Production of Polymer-Coated Fine Granules

Purified water (1568.2 g) was heated to 80° C., and polysorbate 80 (14.58 g), glycerol monostearate (36.45 g), triethyl citrate (36.45 g), yellow ferric oxide (0.409 g) and ferric oxide (0.409 g) were dispersed therein. The suspension was cooled to room temperature, added to mixed dispersion (2430 g) of methacrylic acid-methyl acrylate-methyl methacrylate copolymer dispersion (Eudragit FS30D, manufactured by Evonik Roehm) (2187 g) and methacrylic acid-ethyl acrylate copolymer dispersion (Eudragit L30D-55, manufactured by Evonik Roehm) (243 g), and uniformly mixed to give a coating solution. A predetermined amount (3576 g) of the aforementioned coating solution (4086.498 g) was applied to the fine granules coated with intermediate layer (1215 g), which were obtained in Production Example 29, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1896 g) were obtained.

| [Composition of polymer-coated fine granules (210.676 mg)] | |
|---|---|
| fine granules coated with intermediate layer (Production Example 29) | 135 mg |
| methacrylic acid-methyl acrylate-methyl methacrylate copolymer | 60.75 mg |
| methacrylic acid-ethyl acrylate copolymer | 6.75 mg |
| polysorbate 80 | 1.35 mg |
| glycerol monostearate | 3.375 mg |
| triethyl citrate | 3.375 mg |
| yellow ferric oxide | 0.038 mg |
| ferric oxide | 0.038 mg |
| total | 210.676 mg |

Production Example 31

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (1896 g), which were obtained in Production Example 30, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for 3 min and passed through a round sieve to give mannitol-coated fine granules with a particle size of 250 μm-425 μm.

| [Composition of mannitol-coated fine granules (220.7 mg)] | |
|---|---|
| polymer-coated fine granules (Production Example 30) | 210.7 mg |
| mannitol | 10.0 mg |
| total | 220.7 mg |

Production Example 32

Production of Polymer-Coated Fine Granules

Purified water (1028.4 g) was heated to 80° C., and polysorbate 80 (8.75 g), glycerol monostearate (21.87 g), triethyl citrate (43.74 g), yellow ferric oxide (0.256 g) and ferric oxide (0.256 g) were dispersed therein. The suspension was cooled to room temperature, added to mixed dispersion (1458 g) of methacrylic acid-methyl acrylate-methyl methacrylate copolymer dispersion (Eudragit FS30D, manufactured by Evonik Roehm) (1312 g) and methacrylic acid-ethyl acrylate copolymer dispersion (Eudragit L30D-55, manufactured by Evonik Roehm) (146 g), and uniformly mixed to give a coating solution. A predetermined amount (2241 g) of the aforementioned coating solution (2561.272 g) was applied to the fine granules coated with intermediate layer (1215 g), which were obtained in Production Example 29, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1642 g) were obtained.

| [Composition of polymer-coated fine granules (182.4324 mg)] | |
|---|---|
| fine granules coated with intermediate layer (Production Example 29) | 135 mg |
| methacrylic acid-methyl acrylate-methyl methacrylate copolymer | 36.45 mg |
| methacrylic acid-ethyl acrylate copolymer | 4.05 mg |
| polysorbate 80 | 0.81 mg |
| glycerol monostearate | 2.025 mg |
| triethyl citrate | 4.05 mg |
| yellow ferric oxide | 0.0237 mg |
| ferric oxide | 0.0237 mg |
| total | 182.4324 mg |

Production Example 33

Production of Mannitol-Coated Fine Granules

Mannitol (135 g) was dissolved in purified water (810 g) to give a coating solution. A predetermined amount (630 g) of the aforementioned coating solution (945 g) was applied to the polymer-coated fine granules (1642 g), which were obtained in Production Example 32, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 3 min and passed through a round sieve to give mannitol-coated fine granules with a particle size of 250 μm-425 μm.

| [Composition of mannitol-coated fine granules (192.4 mg)] | |
|---|---|
| polymer-coated fine granules (Production Example 32) | 182.4 mg |
| mannitol | 10.0 mg |
| total | 192.4 mg |

Production Example 34

Production of Outer Layer Component-Granulated Powder

Mannitol (1890 g), low-substituted hydroxypropyl cellulose (L-HPC-33, 300 g), crystalline cellulose (300 g), crospovidone (150 g) and aspartame (90 g) were charged in a fluid bed granulator (FD-3S, manufactured by POWREX CORPORATION), and they were granulated while spraying an aqueous solution of mannitol (150 g) and anhydrous citric acid (30 g) in purified water (820 g) and dried to give an outer layer component-granulated powder (2910 g).

Example 5

Production of Orally-Disintegrating Solid Preparation

The polymer-coated fine granules (346.3 g) obtained in Production Example 25, the polymer-coated fine granules (230.9 g) obtained in Production Example 33, the outer layer component-granulated powder (607.6 g) obtained in Production Example 34, flavor (STRAWBERRY DURAROME, Nihon Firmenich K.K.) (6.1 g) and magnesium stearate (9.1 g) were mixed in a bag to give a mixed powder. The obtained mixed powder (1200 g) was tabletted using a rotary tabletting machine (Correct 19K AWC) (500 mg/tablet, a 12 mmϕ punch, flat-faced with beveled edge, tabletting pressure 13 kN) to give the orally-disintegrating solid preparation (500 mg) containing compound X (30 mg) of the present invention.

Example 6

Production of Orally-Disintegrating Solid Preparation

The polymer-coated fine granules (346.3 g) obtained in Production Example 25, the polymer-coated fine granules (230.9 g) obtained in Production Example 33, the outer layer component-granulated powder (841.8 g) obtained in Production Example 34, flavor (STRAWBERRY DURAROME, Nihon Firmenich K.K.) (8.4 g) and magnesium stearate (12.6 g) were mixed in a bag to give a mixed powder. The obtained mixed powder (1440 g) was tabletted using a rotary tabletting machine (Correct 19K AWC) (600 mg/tablet, a 12 mmϕ punch, flat-faced with beveled edge, tabletting pressure 11 kN) to give the orally-disintegrating solid preparation (600 mg) containing compound X (30 mg) of the present invention.

Example 7

Production of Orally-Disintegrating Solid Preparation

The polymer-coated fine granules (346.3 g) obtained in Production Example 25, the polymer-coated fine granules (230.9 g) obtained in Production Example 33, the outer layer component-granulated powder (1075.9 g) obtained in Production Example 34, flavor (STRAWBERRY DURAROME, Nihon Firmenich K.K.) (10.8 g) and magnesium stearate (16.1 g) were mixed in a bag to give a mixed powder. The obtained mixed powder (1680 g) was tabletted using a rotary tabletting machine (Correct 19K AWC) (700 mg/tablet, a 12 mmϕ punch, flat-faced with beveled edge, tabletting pressure 9 kN) to give the orally-disintegrating solid preparation (700 mg) containing compound X (30 mg) of the present invention.

Example 8

Production of Orally-Disintegrating Solid Preparation

The polymer-coated fine granules (403.4 g) obtained in Production Example 27, the polymer-coated fine granules (230.9 g) obtained in Production Example 33, the outer layer component-granulated powder (669.0 g) obtained in Production Example 34, flavor (STRAWBERRY DURAROME, Nihon Firmenich K.K.) (6.7 g) and magnesium stearate (10.0 g) were mixed in a bag to give a mixed powder. The obtained mixed powder (1320 g) was tabletted using a rotary tabletting machine (Correct 19K AWC) (550 mg/tablet, a 12 mmϕ punch, flat-faced with beveled edge, tabletting pressure 12 kN) to give the orally-disintegrating solid preparation (550 mg) containing compound X (30 mg) of the present invention.

Example 9

Production of Orally-Disintegrating Solid Preparation

The polymer-coated fine granules (403.4 g) obtained in Production Example 27, the polymer-coated fine granules (230.9 g) obtained in Production Example 33, the outer layer component-granulated powder (903.2 g) obtained in Production Example 34, flavor (STRAWBERRY DURAROME, Nihon Firmenich K.K.) (9.0 g) and magnesium stearate (13.5 g) were mixed in a bag to give a mixed powder. The obtained mixed powder (1560 g) was tabletted using a rotary tabletting machine (Correct 19K AWC) (650 mg/tablet, a 12 mmϕ punch, flat-faced with beveled edge, tabletting pressure 10 kN) to give the orally-disintegrating solid preparation (650 mg) containing compound X (30 mg) of the present invention.

Example 10

Production of Orally-Disintegrating Solid Preparation

The polymer-coated fine granules (403.4 g) obtained in Production Example 27, the polymer-coated fine granules (230.9 g) obtained in Production Example 33, the outer layer component-granulated powder (1137.3 g) obtained in Production Example 34, flavor (STRAWBERRY DURAROME, Nihon Firmenich K.K.) (11.4 g) and magnesium stearate (17.1 g) were mixed in a bag to give a mixed powder. The obtained mixed powder (1800.1 g) was tabletted using a rotary tabletting machine (Correct 19K AWC) (750 mg/tablet, a 12 mmϕ punch, flat-faced with beveled edge, tabletting pressure 9 kN) to give the orally-disintegrating solid preparation (750 mg) containing compound X (30 mg) of the present invention.

Production Example 35

Production of Fine Granules Coated with Pharmaceutically Active Ingredient

Core granules to be the core of controlled release fine granules A were produced as follows. Hydroxypropyl cellulose (HPC-SL-T, 360 g) was dissolved in purified water (4680 g), low-substituted hydroxypropyl cellulose (L-HPC-32, 180 g) and magnesium carbonate (360 g) were dispersed in this solution. Compound X (1080 g) was uniformly dispersed in the obtained dispersion to give a coating solution. A predetermined amount (5550 g) of the compound X-containing coating solution (6660 g) was applied to lactose-crystalline cellulose spheres (Nonpareil 105T, 900 g) using a rotary fluidized bed coater (MP-10 TOKU-2 type, manufactured by POWREX CORPORATION). The coating conditions were: inlet air temperature about 70° C., product temperature about 31° C., spray air volume about 80 NL/min, rotor speed about 500 rpm, spray rate about 17 g/min, spray gun position tangential. After the completion of coating, core granules (2550 g) were obtained.

[Composition of fine granules coated with pharmaceutically active ingredient (63.75 mg)]

| | |
|---|---|
| lactose-crystalline cellulose spheres (Nonpareil 105T) | 22.5 mg |
| compound X | 22.5 mg |
| magnesium carbonate | 7.5 mg |
| low-substituted hydroxypropyl cellulose | 3.75 mg |
| hydroxypropyl cellulose | 7.5 mg |
| total | 63.75 mg |

Production Example 36

Production of Fine Granules Coated with Intermediate Layer

The pharmaceutically active ingredient-coated fine granules obtained in Production Example 35 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 252 g) and mannitol (252 g) in purified water (2700 g), and dispersing titanium oxide (108 g), talc (108 g) and low-substituted hydroxypropyl cellulose (L-HPC-32, 180 g) in the obtained solution. A predetermined amount (3000 g) of the intermediate layer coating solution (3600 g) was applied to the fine granules coated with pharmaceutically active ingredient (2550 g), which were obtained in Production Example 35, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

[Composition of fine granules coated with intermediate layer (82.5 mg)]

| | |
|---|---|
| fine granules coated with pharmaceutically active ingredient (Production Example 35) | 63.75 mg |
| hypromellose | 5.25 mg |
| low-substituted hydroxypropyl cellulose | 3.75 mg |
| talc | 2.25 mg |
| titanium oxide | 2.25 mg |
| mannitol | 5.25 mg |
| total | 82.5 mg |

Production Example 37

Production of Fine Granules Coated with Intermediate Layer

The pharmaceutically active ingredient-coated fine granules obtained in Production Example 36 was coated with an intermediate layer coating solution using a rotary fluidized bed coater (MP-10 TOKU-2 type, manufactured by POWREX CORPORATION) to give fine granules with the following composition. The intermediate layer coating solution was produced by dissolving hypromellose (TC-5E, 252 g) and mannitol (252 g) in purified water (2700 g), and dispersing titanium oxide (108 g), talc (108 g) and low-substituted hydroxypropyl cellulose (L-HPC-32, 180 g) in the obtained solution. A predetermined amount (900 g) of the intermediate layer coating solution (3600 g) was applied to the fine granules coated with intermediate layer (990 g), which were obtained in Production Example 36, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, fine granules coated with intermediate layer (1215 g) were obtained.

[Composition of fine granules coated with intermediate layer (101.25 mg)]

| | |
|---|---|
| fine granules coated with intermediate layer (Production Example 36) | 82.5 mg |
| hypromellose | 5.25 mg |
| low-substituted hydroxypropyl cellulose | 3.75 mg |
| talc | 2.25 mg |
| titanium oxide | 2.25 mg |
| mannitol | 5.25 mg |
| total | 101.25 mg |

Production Example 38

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, added to mixed dispersion (2430.5 g) of methacrylic acid-methyl acrylate-methyl methacrylate copolymer dispersion (Eudragit FS30D, manufactured by Evonik Roehm) (2309 g) and methacrylic acid-ethyl acrylate copolymer dispersion (Eudragit L30D-55, manufactured by Evonik Roehm) (121.5 g), and uniformly mixed to give a coating solution. A predetermined amount (3735 g) of the aforementioned coating solution (4270 g) was applied to the fine granules coated with intermediate layer (1215 g), which were obtained in Production Example 37, using a rotary fluidized bed coater (MP-10 TOKU-2 type, manufactured by POWREX CORPORATION). The coating conditions were: inlet air temperature about 40° C., product temperature about 26° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (160.575 mg)] | |
| --- | --- |
| fine granules coated with intermediate layer (Production Example 37) | 101.25 mg |
| methacrylic acid-methyl acrylate-methyl methacrylate copolymer | 48.09375 mg |
| methacrylic acid-ethyl acrylate copolymer | 2.53125 mg |
| polysorbate 80 | 1.0125 mg |
| glycerol monostearate | 2.53125 mg |
| triethyl citrate | 5.0625 mg |
| yellow ferric oxide | 0.046875 mg |
| ferric oxide | 0.046875 mg |
| total | 160.575 mg |

Production Example 39

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 38, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (168.075 mg)] | |
| --- | --- |
| polymer-coated fine granules (Production Example 38) | 160.575 mg |
| mannitol | 7.5 mg |
| total | 168.075 mg |

Production Example 40

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, and added to methacrylic acid-methyl acrylate-methyl methacrylate copolymer dispersion (Eudragit FS30D, manufactured by Evonik Roehm) (2430 g) and uniformly mixed to give a coating solution. A predetermined amount (3735 g) of the aforementioned coating solution (4270 g) was applied to the fine granules coated with intermediate layer (1215 g), which were obtained in Production Example 37, using a rotary fluidized bed coater (MP-10 TOKU-2 type, manufactured by POWREX CORPORATION). The coating conditions were: inlet air temperature about 40° C., product temperature about 26° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (160.575 mg)] | |
| --- | --- |
| fine granules coated with intermediate layer (Production Example 37) | 101.25 mg |
| methacrylic acid-methyl acrylate-methyl methacrylate copolymer | 50.625 mg |
| polysorbate 80 | 1.0125 mg |
| glycerol monostearate | 2.53125 mg |
| triethyl citrate | 5.0625 mg |
| yellow ferric oxide | 0.046875 mg |
| ferric oxide | 0.046875 mg |
| total | 160.575 mg |

Production Example 41

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 40, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (168.075 mg)] | |
| --- | --- |
| polymer-coated fine granules (Production Example 40) | 160.575 mg |
| mannitol | 7.5 mg |
| total | 168.075 mg |

Production Example 42

Production of Fine Granules Coated with Pharmaceutically Active Ingredient

Core granules to be the core of controlled release fine granules B were produced as follows. Hydroxypropyl cellulose (HPC-SL-T, 360 g) and mannitol (270 g) were dissolved in purified water (4680 g), talc (270 g), low-substituted hydroxypropyl cellulose (L-HPC-32, 180 g) and magnesium carbonate (360 g) were dispersed in this solution. Compound X (540 g) was uniformly dispersed in the obtained dispersion to give a coating solution. A predetermined amount (5550 g) of the compound X-containing coating solution (6660 g) was applied to lactose-crystalline cellulose spheres (Nonpareil 105T, 900 g) using a rotary fluidized bed coater (MP-10 TOKU-2 type, manufactured by POWREX CORPORATION). The coating conditions were: inlet air temperature about 70° C., product temperature about 31° C., spray air volume about 80 NL/min, rotor speed about 500 rpm, spray rate about 14 g/min, spray gun position tangential. After the completion of coating, core granules (2550 g) were obtained.

| [Composition of fine granules coated with pharmaceutically active ingredient (42.5 mg)] | |
|---|---|
| lactose-crystalline cellulose spheres (Nonpareil 105T) | 15 mg |
| compound X | 7.5 mg |
| mannitol | 3.75 mg |
| talc | 3.75 mg |
| magnesium carbonate | 5 mg |
| low-substituted hydroxypropyl cellulose | 2.5 mg |
| hydroxypropyl cellulose | 5 mg |
| total | 42.5 mg |

Production Example 43

Production of Fine Granules Coated with Intermediate Layer

The pharmaceutically active ingredient-coated fine granules obtained in Production Example 42 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 252 g) and mannitol (252 g) in purified water (2700 g), and dispersing titanium oxide (108 g), talc (108 g) and low-substituted hydroxypropyl cellulose (L-HPC-32, 180 g) in the obtained solution. A predetermined amount (3000 g) of the intermediate layer coating solution (3600 g) was applied to the fine granules coated with pharmaceutically active ingredient (2550 g), which were obtained in Production Example 42, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

| [Composition of fine granules coated with intermediate layer (55 mg)] | |
|---|---|
| fine granules coated with pharmaceutically active ingredient (Production Example 42) | 42.5 mg |
| hypromellose | 3.5 mg |
| low-substituted hydroxypropyl cellulose | 2.5 mg |
| talc | 1.5 mg |
| titanium oxide | 1.5 mg |
| mannitol | 3.5 mg |
| total | 55 mg |

Production Example 44

Production of Fine Granules Coated with Intermediate Layer

The fine granules coated with intermediate layer obtained in Production Example 43 was coated with an intermediate layer coating solution using a rotary fluidized bed coater (MP-10 TOKU-2 type, manufactured by POWREX CORPORATION) to give fine granules with the following composition. The intermediate layer coating solution was produced by dissolving hypromellose (TC-5E, 252 g) and mannitol (252 g) in purified water (2700 g), and dispersing titanium oxide (108 g), talc (108 g) and low-substituted hydroxypropyl cellulose (L-HPC-32, 180 g) in the obtained solution. A predetermined amount (900 g) of the intermediate layer coating solution (3600 g) was applied to the fine granules coated with intermediate layer (990 g), which were obtained in Production Example 43, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, fine granules coated with intermediate layer (1215 g) were obtained.

| [Composition of fine granules coated with intermediate layer (67.5 mg)] | |
|---|---|
| fine granules coated with intermediate layer (Production Example 43) | 55 mg |
| hypromellose | 3.5 mg |
| low-substituted hydroxypropyl cellulose | 2.5 mg |
| talc | 1.5 mg |
| titanium oxide | 1.5 mg |
| mannitol | 3.5 mg |
| total | 67.5 mg |

Production Example 45

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, and added to mixed dispersion (2430.5 g) of methacrylic acid-methyl acrylate-methyl methacrylate copolymer dispersion (Eudragit FS30D, manufactured by Evonik Roehm) (2309 g) and methacrylic acid-ethyl acrylate copolymer dispersion (Eudragit L30D-55, manufactured by Evonik Roehm) (121.5 g), and uniformly mixed to give a coating solution. A predetermined amount (3735 g) of the aforementioned coating solution (4270 g) was applied to the fine granules coated with intermediate layer (1215 g), which were obtained in Production Example 44, using a rotary fluidized bed coater (MP-10 TOKU-2 type, manufactured by POWREX CORPORATION). The coating conditions were: inlet air temperature about 40° C., product temperature about 40° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (107.05 mg)] | |
|---|---|
| fine granules coated with intermediate layer (Production Example 44) | 67.5 mg |
| methacrylic acid-methyl acrylate-methyl methacrylate copolymer | 28.6875 mg |
| methacrylic acid-ethyl acrylate copolymer | 5.0625 mg |
| polysorbate 80 | 0.675 mg |
| glycerol monostearate | 1.6875 mg |
| triethyl citrate | 3.375 mg |
| yellow ferric oxide | 0.03125 mg |
| ferric oxide | 0.03125 mg |
| total | 107.05 mg |

Production Example 46

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 45, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (112.05 mg)] | |
|---|---|
| polymer-coated fine granules (Production Example 45) | 107.05 mg |
| mannitol | 5 mg |
| total | 112.05 mg |

Production Example 47

Production of Outer Layer Component-Granulated Powder

Mannitol (3452 g), low-substituted hydroxypropyl cellulose (L-HPC-33, 544 g), crystalline cellulose (544 g) and crospovidone (272 g) were charged in a fluid bed granulator (FD-5S, manufactured by POWREX CORPORATION), and they were granulated while spraying an aqueous solution of mannitol (272 g) and anhydrous citric acid (54.4 g) in purified water (1488 g) and dried to give an outer layer component-granulated powder (5138 g).

| [Composition of outer layer component-granulated powder (302.275 mg)] | |
|---|---|
| mannitol | 219.075 mg |
| low-substituted hydroxypropyl cellulose | 32 mg |
| crystalline cellulose | 32 mg |
| crospovidone | 16 mg |
| anhydrous citric acid | 3.2 mg |
| total | 302.275 mg |

Example 11

Production of Orally-Disintegrating Solid Preparation

The mannitol-coated fine granules (1345 g) obtained in Production Example 39, the mannitol-coated fine granules (896.4 g) obtained in Production Example 46, the outer layer component-granulated powder (2418 g) obtained in Production Example 47, sucralose (76.8 g), flavor (STRAWBERRY DURAROME, Nihon Firmenich K.K.) (25.6 g) and magnesium stearate (38.4 g) were mixed using a tumbling mixer to give a mixed powder. The obtained mixed powder (4800 g) was tabletted using a rotary tabletting machine (AQUARIUS, manufactured by Kikusui Seisakusho Ltd.) (600 mg/tablet, a 12 mmφ punch, flat-faced with beveled edge, tabletting pressure 12.5 kN) to give the orally-disintegrating solid preparation (600 mg) containing compound X (30 mg) of the present invention. The hardness and the disintegration time in the oral cavity of the obtained tablet were 36 N and 37 seconds, respectively. The dissolution rate of the obtained tablet in 0.1N HCl in 2 hours was 1.3%, showing superior acid resistance.

| [Composition of orally-disintegrating solid preparation (600 mg)] | |
|---|---|
| mannitol-coated fine granules (Production Example 39) | 168.075 mg |
| mannitol-coated fine granules (Production Example 46) | 112.05 mg |
| outer layer component-granulated powder (Production Example 47) | 302.275 mg |
| sucralose | 9.6 mg |
| flavor | 3.2 mg |
| magnesium stearate | 4.8 mg |
| total | 600 mg |

Example 12

Production of Orally-Disintegrating Solid Preparation

The mannitol-coated fine granules (1345 g) obtained in Production Example 41, the mannitol-coated fine granules (896.4 g) obtained in Production Example 46, the outer layer component-granulated powder (2418 g) obtained in Production Example 47, sucralose (76.8 g), flavor (STRAWBERRY DURAROME, Nihon Firmenich K.K.) (25.6 g) and magnesium stearate (38.4 g) were mixed using a tumbling mixer to give a mixed powder. The obtained mixed powder (4800 g) was tabletted using a rotary tabletting machine (AQUARIUS, manufactured by Kikusui Seisakusho Ltd.) (600 mg/tablet, a 12 mmφ punch, flat-faced with beveled edge, tabletting pressure 12.5 kN) to give the orally-disintegrating solid preparation (600 mg) containing compound X (30 mg) of the present invention. The hardness and the disintegration time in the oral cavity of the obtained tablet were 37 N and 38 seconds, respectively. The dissolution rate of the obtained tablet in 0.1N HCl in 2 hours was 0.7%, showing superior acid resistance.

| [Composition of orally-disintegrating solid preparation (600 mg)] | |
|---|---|
| mannitol-coated fine granules (Production Example 41) | 168.075 mg |
| mannitol-coated fine granules (Production Example 46) | 112.05 mg |
| outer layer component-granulated powder (Production Example 47) | 302.275 mg |
| sucralose | 9.6 mg |
| flavor | 3.2 mg |
| magnesium stearate | 4.8 mg |
| total | 600 mg |

Production Example 48

Production of Fine Granules Coated with Intermediate Layer

The fine granules coated with pharmaceutically active ingredient obtained in Production Example 35 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 126 g) and mannitol (126 g) in purified water (1350 g), and dispersing titanium oxide (54 g), talc (54 g) and low-substituted hydroxypropyl cellulose (L-HPC-32, 90 g) in the obtained solution. A predetermined amount (1500 g) of the intermediate layer coating solution (1800 g) was applied to the fine granules coated with pharmaceutically active ingredient (2550 g), which were obtained in Production Example 35, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

| [Composition of fine granules coated with intermediate layer (73.125 mg)] | |
|---|---|
| fine granules coated with pharmaceutically active ingredient (Production Example 35) | 63.75 mg |
| hypromellose | 2.625 mg |
| low-substituted hydroxypropyl cellulose | 1.875 mg |
| talc | 1.125 mg |
| titanium oxide | 1.125 mg |
| mannitol | 2.625 mg |
| total | 73.125 mg |

Production Example 49

Production of Fine Granules Coated with Intermediate Layer

The fine granules coated with intermediate layer obtained in Production Example 48 was coated with an intermediate layer coating solution using a rotary fluidized bed coater (MP-10 TOKU-2 type, manufactured by POWREX CORPORATION) to give fine granules with the following composition. The intermediate layer coating solution was produced by dissolving hypromellose (TC-5E, 105 g) and mannitol (105 g) in purified water (1125 g), and dispersing titanium oxide (45 g), talc (45 g) and low-substituted hydroxypropyl cellulose (L-HPC-32, 75 g) in the obtained solution. A predetermined amount (500 g) of the intermediate layer coating solution (1500 g) was applied to the fine granules coated with intermediate layer (975 g), which were obtained in Production Example 48, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 16 g/min, spray gun position tangential. After the completion of coating, fine granules coated with intermediate layer (1100 g) were obtained.

| [Composition of fine granules coated with intermediate layer (82.5 mg)] | |
|---|---|
| fine granules coated with intermediate layer (Production Example 48) | 73.125 mg |
| hypromellose | 2.625 mg |
| low-substituted hydroxypropyl cellulose | 1.875 mg |
| talc | 1.125 mg |
| titanium oxide | 1.125 mg |
| mannitol | 2.625 mg |
| total | 82.5 mg |

Production Example 50

Production of Polymer-Coated Fine Granules

Purified water (1551.9 g) was heated to 80° C., and polysorbate 80 (13.2 g), glycerol monostearate (33 g), triethyl citrate (66 g), yellow ferric oxide (0.386 g) and ferric oxide (0.386 g) were dispersed therein. The suspension was cooled to room temperature, and added to methacrylic acid-methyl acrylate-methyl methacrylate copolymer dispersion (Eudragit FS30D, manufactured by Evonik Roehm) (2200 g) and uniformly mixed to give a coating solution. A predetermined amount (3382 g) of the aforementioned coating solution (3865 g) was applied to the fine granules coated with intermediate layer (1100 g), which were obtained in Production Example 49, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1744 g) were obtained.

[Composition of polymer-coated fine granules (130.811 mg)]

| | |
|---|---|
| fine granules coated with intermediate layer (Production Example 49) | 82.5 mg |
| methacrylic acid-methyl acrylate-methyl methacrylate copolymer | 41.25 mg |
| polysorbate 80 | 0.825 mg |
| glycerol monostearate | 2.0625 mg |
| triethyl citrate | 4.125 mg |
| yellow ferric oxide | 0.02415 mg |
| ferric oxide | 0.02415 mg |
| total | 130.811 mg |

Production Example 51

Production of Mannitol-Coated Fine Granules

Mannitol (150 g) was dissolved in purified water (900 g) to give a coating solution. A predetermined amount (700 g) of the aforementioned coating solution (1050 g) was applied to the polymer-coated fine granules (1744 g), which were obtained in Production Example 50, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol coated fine granules with a particle size of 250 µm-425 µm.

[Composition of mannitol-coated fine granules (138.311 mg)]

| | |
|---|---|
| polymer-coated fine granules (Production Example 50) | 130.811 mg |
| mannitol | 7.5 mg |
| total | 138.311 mg |

Production Example 52

Production of Polymer-Coated Fine Granules

Purified water (1551.9 g) was heated to 80° C., and polysorbate 80 (13.2 g), glycerol monostearate (33 g), triethyl citrate (66 g), yellow ferric oxide (0.386 g) and ferric oxide (0.386 g) were dispersed therein. The suspension was cooled to room temperature, and added to mixed dispersion (2200 g) of methacrylic acid-methyl acrylate-methyl methacrylate copolymer dispersion (Eudragit FS30D, manufactured by Evonik Roehm) (2090 g) and methacrylic acid-ethyl acrylate copolymer dispersion (Eudragit L30D-55, manufactured by Evonik Roehm) (110 g), and uniformly mixed to give a coating solution. A predetermined amount (3382 g) of the aforementioned coating solution (3865 g) was applied to the fine granules coated with intermediate layer (1100 g), which were obtained in Production Example 49, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1744 g) were obtained.

[Composition of polymer-coated fine granules (130.811 mg)]

| | |
|---|---|
| fine granules coated with intermediate layer (Production Example 49) | 82.5 mg |
| methacrylic acid-methyl acrylate-methyl methacrylate copolymer | 39.1875 mg |
| methacrylic acid-ethyl acrylate copolymer | 2.0625 mg |
| polysorbate 80 | 0.825 mg |
| glycerol monostearate | 2.0625 mg |
| triethyl citrate | 4.125 mg |
| yellow ferric oxide | 0.02415 mg |
| ferric oxide | 0.02415 mg |
| total | 130.811 mg |

Production Example 53

Production of Mannitol-Coated Fine Granules

Mannitol (150 g) was dissolved in purified water (900 g) to give a coating solution. A predetermined amount (700 g) of the aforementioned coating solution (1050 g) was applied to the polymer-coated fine granules (1744 g), which were obtained in Production Example 52, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 µm-425 µm.

[Composition of mannitol-coated fine granules (138.311 mg)]

| | |
|---|---|
| polymer-coated fine granules (Production Example 52) | 130.811 mg |
| mannitol | 7.5 mg |
| total | 138.311 mg |

Production Example 54

Production of Fine Granules Coated with Intermediate Layer

The fine granules coated with pharmaceutically active ingredient obtained in Production Example 42 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 126 g) and mannitol (126 g) in purified water (1350 g), and dispersing titanium oxide (54 g), talc (54 g) and low-substituted hydroxypropyl cellulose (L-HPC-32, 90 g) in the obtained solution. A predetermined amount (1500 g) of the intermediate layer coating solution (1800 g) was applied to the fine granules coated with pharmaceutically active ingredient (2550 g), which were obtained in Production Example 42, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

[Composition of fine granules coated with intermediate layer (48.75 mg)]

| | |
|---|---|
| fine granules coated with pharmaceutically active ingredient (Production Example 42) | 42.5 mg |
| hypromellose | 1.75 mg |
| low-substituted hydroxypropyl cellulose | 1.25 mg |
| talc | 0.75 mg |
| titanium oxide | 0.75 mg |
| mannitol | 1.75 mg |
| total | 48.75 mg |

Production Example 55

Production of Fine Granules Coated with Intermediate Layer

The fine granules coated with intermediate layer obtained in Production Example 54 was coated with an intermediate layer coating solution using a rotary fluidized bed coater (MP-10 TOKU-2 type, manufactured by POWREX CORPORATION) to give fine granules with the following composition. The intermediate layer coating solution was produced by dissolving hypromellose (TC-5E, 105 g) and mannitol (105 g) in purified water (1125 g), and dispersing titanium oxide (45 g), talc (45 g) and low-substituted hydroxypropyl cellulose (L-HPC-32, 75 g) in the obtained solution. A predetermined amount (500 g) of the intermediate layer coating solution (1500 g) was applied to the fine granules coated with intermediate layer (975 g), which were obtained in Production Example 54, using a rotary fluidized bed coater (MP-10 TOKU-2 type, manufactured by POWREX CORPORATION). The coating conditions were: inlet air temperature about 85° C., product temperature about 41° C., spray air volume about 100 NL/min, rotor speed about 550 rpm, spray rate about 16 g/min, spray gun position tangential. After the completion of coating, fine granules coated with intermediate layer (1100 g) were obtained.

[Composition of fine granules coated with intermediate layer (55 mg)]

| | |
|---|---|
| fine granules coated with intermediate layer (Production Example 54) | 48.75 mg |
| hypromellose | 1.75 mg |
| low-substituted hydroxypropyl cellulose | 1.25 mg |
| talc | 0.75 mg |
| titanium oxide | 0.75 mg |
| mannitol | 1.75 mg |
| total | 55 mg |

Production Example 56

Production of Polymer-Coated Fine Granules

Purified water (1551.9 g) was heated to 80° C., and polysorbate 80 (13.2 g), glycerol monostearate (33 g), triethyl citrate (66 g), yellow ferric oxide (0.386 g) and ferric oxide (0.386 g) were dispersed therein. The suspension was cooled to room temperature, and added to mixed dispersion (2200 g) of methacrylic acid-methyl acrylate-methyl methacrylate copolymer dispersion (Eudragit FS30D, manufactured by Evonik Roehm) (1870 g) and methacrylic acid-ethyl acrylate copolymer dispersion (Eudragit L30D-55, manufactured by Evonik Roehm) (330 g), and uniformly mixed to give a coating solution. A predetermined amount (3382 g) of the aforementioned coating solution (3865 g) was applied to the fine granules coated with intermediate layer (1100 g), which were obtained in Production Example 55, using a rotary fluidized bed coater (MP-10 TOKU-2 type, manufactured by POWREX CORPORATION). The coating conditions were: inlet air temperature about 45° C., product temperature about 26° C., spray air volume about 120 NL/min, rotor speed about 550 rpm, spray rate about 7 g/min, spray gun position tangential. After the completion of coating, polymer-coated fine granules (1744 g) were obtained.

[Composition of polymer-coated fine granules (87.21 mg)]

| | |
|---|---|
| fine granules coated with intermediate layer (Production Example 55) | 55 mg |
| methacrylic acid-methyl acrylate-methyl methacrylate copolymer | 23.375 mg |
| methacrylic acid-ethyl acrylate copolymer | 4.125 mg |
| polysorbate 80 | 0.55 mg |
| glycerol monostearate | 1.375 mg |
| triethyl citrate | 2.75 mg |
| yellow ferric oxide | 0.0161 mg |
| ferric oxide | 0.0161 mg |
| total | 87.21 mg |

Production Example 57

Production of Mannitol-Coated Fine Granules

Mannitol (150 g) was dissolved in purified water (900 g) to give a coating solution. A predetermined amount (700 g) of the aforementioned coating solution (1050 g) was applied to the polymer-coated fine granules (1744 g), which were obtained in Production Example 56, using a rotary fluidized bed coater (MP-10 TOKU-2 type, manufactured by POWREX CORPORATION). The coating conditions were: inlet air temperature about 70° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

[Composition of mannitol-coated fine granules (92.21 mg)]

| | |
|---|---|
| polymer-coated fine granules (Production Example 56) | 87.21 mg |
| mannitol | 5 mg |
| total | 92.21 mg |

Production Example 58

Production of Outer Layer Component-Granulated Powder

Mannitol (1890 g), low-substituted hydroxypropyl cellulose (L-HPC-33, 300 g), crystalline cellulose (300 g), crospovidone (150 g) and aspartame (90 g) were charged in a fluid bed granulator (FD-3S, manufactured by POWREX CORPORATION), and they were granulated while spraying an aqueous solution of mannitol (150 g) and anhydrous citric acid (30 g) in purified water (820 g) and dried to give an outer layer component-granulated powder (2910 g).

[Composition of outer layer component-granulated powder (165.2 mg)]

| | |
|---|---|
| mannitol | 115.9 mg |
| low-substituted hydroxypropyl cellulose | 17 mg |
| crystalline cellulose | 17 mg |
| crospovidone | 8.5 mg |
| anhydrous citric acid | 1.7 mg |
| aspartame | 5.1 mg |
| total | 165.2 mg |

Example 13

Production of Orally-Disintegrating Solid Preparation

The polymer-coated fine granules (276.6 g) obtained in Production Example 51, the polymer-coated fine granules (184.4 g) obtained in Production Example 57, the outer layer component-granulated powder (330.7 g) obtained in Production Example 58, flavor (STRAWBERRY DURAROME, Nihon Firmenich K.K.) (3.3 g) and magnesium stearate (5 g) were mixed in a bag to give a mixed powder. The obtained mixed powder (800 g) was tabletted using a rotary tabletting machine (Correct 19K AWC) (400 mg/tablet, a 12 mmφ punch, flat-faced with beveled edge, tabletting pressure 15 kN) to give the orally-disintegrating solid preparation (400 mg) containing compound X (30 mg) of the present invention. The hardness and the disintegration time in the oral cavity of the obtained tablet were 32 N and 40 seconds, respectively. The dissolution rate of the obtained tablet in 0.1N HCl in 2 hours was 2.5%, showing superior acid resistance.

[Composition of orally-disintegrating solid preparation (400 mg)]

| | |
|---|---|
| mannitol-coated fine granules (Production Example 51) | 138.311 mg |
| mannitol-coated fine granules (Production Example 57) | 92.21 mg |
| outer layer component-granulated powder (Production Example 58) | 165.2 mg |
| flavor | 1.7 mg |
| magnesium stearate | 2.5 mg |
| total | 400 mg |

Example 14

Production of Orally-Disintegrating Solid Preparation

The polymer-coated fine granules (276.6 g) obtained in Production Example 51, the polymer-coated fine granules (184.4 g) obtained in Production Example 57, the outer layer component-granulated powder (428.2 g) obtained in Production Example 58, flavor (STRAWBERRY DURAROME, Nihon Firmenich K.K.) (4.3 g) and magnesium stearate (6.4 g) were mixed in a bag to give a mixed powder. The obtained mixed powder (900 g) was tabletted using a rotary tabletting machine (Correct 19K AWC) (450 mg/tablet, a 12 mmφ punch, flat-faced with beveled edge, tabletting pressure 14 kN) to give the orally-disintegrating solid preparation (450 mg) containing compound X (30 mg) of the present invention. The hardness and the disintegration time in the oral cavity of the obtained tablet were 33 N and 38 seconds, respectively. The dissolution rate of the obtained tablet in 0.1N HCl in 2 hours was 1.9%, showing superior acid resistance.

[Composition of orally-disintegrating solid preparation (450 mg)]

| | |
|---|---|
| mannitol-coated fine granules (Production Example 51) | 138.311 mg |
| mannitol-coated fine granules (Production Example 57) | 92.21 mg |
| outer layer component-granulated powder (Production Example 58) | 214.1 mg |
| flavor | 2.1 mg |
| magnesium stearate | 3.2 mg |
| total | 450 mg |

Example 15

Production of Orally-Disintegrating Solid Preparation

The polymer-coated fine granules (276.6 g) obtained in Production Example 51, the polymer-coated fine granules (184.4 g) obtained in Production Example 57, the outer layer component-granulated powder (525.9 g) obtained in Production Example 58, flavor (STRAWBERRY DURAROME, Nihon Firmenich K.K.) (5.3 g) and magnesium stearate (7.9 g) were mixed in a bag to give a mixed powder. The obtained mixed powder (1000 g) was tabletted using a rotary tabletting machine (Correct 19K AWC) (500 mg/tablet, a 12 mmφ punch, flat-faced with beveled edge, tabletting pressure 13 kN) to give the orally-disintegrating solid preparation (500 mg) containing compound X (30 mg) of the present invention. The hardness and the disintegration time in the oral cavity of the obtained tablet were 34 N and 39 seconds, respectively. The dissolution rate of the obtained tablet in 0.1N HCl in 2 hours was 1.6%, showing superior acid resistance.

[Composition of orally-disintegrating solid preparation (500 mg)]

| | |
|---|---|
| mannitol-coated fine granules (Production Example 51) | 138.311 mg |
| mannitol-coated fine granules (Production Example 57) | 92.21 mg |
| outer layer component-granulated powder (Production Example 58) | 262.9 mg |
| flavor | 2.6 mg |
| magnesium stearate | 3.9 mg |
| total | 500 mg |

Example 16

Production of Orally-Disintegrating Solid Preparation

The polymer-coated fine granules (276.6 g) obtained in Production Example 53, the polymer-coated fine granules (184.4 g) obtained in Production Example 57, the outer layer component-granulated powder (330.7 g) obtained in Production Example 58, flavor (STRAWBERRY DURAROME, Nihon Firmenich K.K.) (3.3 g) and magnesium stearate (5 g) were mixed in a bag to give a mixed powder. The obtained mixed powder (800 g) was tabletted using a rotary tabletting machine (Correct 19K AWC) (400 mg/tablet, a 12 mmφ punch, flat-faced with beveled edge, tabletting pressure 14 kN) to give the orally-disintegrating solid preparation (400 mg) containing compound X (30 mg) of the present invention. The hardness and the disintegration time in the oral cavity of the obtained tablet were 37 N and 43 seconds, respectively. The dissolution rate of the obtained tablet in 0.1N HCl in 2 hours was 2.2%, showing superior acid resistance.

[Composition of orally-disintegrating solid preparation (400 mg)]

| | |
|---|---|
| mannitol-coated fine granules (Production Example 53) | 138.311 mg |
| mannitol-coated fine granules (Production Example 57) | 92.21 mg |
| outer layer component-granulated powder (Production Example 58) | 165.2 mg |
| flavor | 1.7 mg |
| magnesium stearate | 2.5 mg |
| total | 400 mg |

Example 17

Production of Orally-Disintegrating Solid Preparation

The polymer-coated fine granules (276.6 g) obtained in Production Example 53, the polymer-coated fine granules (184.4 g) obtained in Production Example 57, the outer layer component-granulated powder (428.2 g) obtained in Production Example 58, flavor (STRAWBERRY DURAROME, Nihon Firmenich K.K.) (4.3 g) and magnesium stearate (6.4 g) were mixed in a bag to give a mixed powder. The obtained mixed powder (900 g) was tabletted using a rotary tabletting machine (Correct 19K AWC) (450 mg/tablet, a 12 mmφ punch, flat-faced with beveled edge, tabletting pressure 13 kN) to give the orally-disintegrating solid preparation (450 mg) containing compound X (30 mg) of the present invention. The hardness and the disintegration time in the oral cavity of the obtained tablet were 38 N and 35 seconds, respectively. The dissolution rate of the obtained tablet in 0.1N HCl in 2 hours was 1.6%, showing superior acid resistance.

[Composition of orally-disintegrating solid preparation (450 mg)]

| | |
|---|---|
| mannitol-coated fine granules (Production Example 53) | 138.311 mg |
| mannitol-coated fine granules (Production Example 57) | 92.21 mg |
| outer layer component-granulated powder (Production Example 58) | 214.1 mg |
| flavor | 2.1 mg |
| magnesium stearate | 3.2 mg |
| total | 450 mg |

Example 18

Production of Orally-Disintegrating Solid Preparation

The polymer-coated fine granules (276.6 g) obtained in Production Example 53, the polymer-coated fine granules (184.4 g) obtained in Production Example 57, the outer layer component-granulated powder (525.9 g) obtained in Production Example 58, flavor (STRAWBERRY DURAROME, Nihon Firmenich K.K.) (5.3 g) and magnesium stearate (7.9 g) were mixed in a bag to give a mixed powder. The obtained mixed powder (1000 g) was tabletted using a rotary tabletting machine (Correct 19K AWC) (500 mg/tablet, a 12 mmφ punch, flat-faced with beveled edge, tabletting pressure 11 kN) to give the orally-disintegrating solid preparation (500 mg) containing compound X (30 mg) of the present invention. The hardness and the disintegration time in the oral cavity of the obtained tablet were 36 N and 31 seconds, respectively. The dissolution rate of the obtained tablet in 0.1N HCl in 2 hours was 1.6%, showing superior acid resistance.

[Composition of orally-disintegrating solid preparation (500 mg)]

| | |
|---|---|
| mannitol-coated fine granules (Production Example 53) | 138.311 mg |
| mannitol-coated fine granules (Production Example 57) | 92.21 mg |
| outer layer component-granulated powder (Production Example 58) | 262.9 mg |
| flavor | 2.6 mg |
| magnesium stearate | 3.9 mg |
| total | 500 mg |

Example 19

Production of Orally-Disintegrating Solid Preparation

The polymer-coated fine granules (276.6 g) obtained in Production Example 51, the polymer-coated fine granules (184.4 g) obtained in Production Example 57, the outer layer component-granulated powder (428.2 g) obtained in Production Example 58, flavor (STRAWBERRY DURAROME, Nihon Firmenich K.K.) (4.3 g) and magnesium stearate (6.4 g) were mixed in a bag to give a mixed powder. The obtained mixed powder (900 g) was tabletted using a rotary tabletting machine (Correct 19K AWC) (900 mg/tablet, a 13 mmφ punch, flat-faced with beveled edge, tabletting pressure 14 kN) to give the orally-disintegrating solid preparation (900 mg) containing compound X (60 mg) of the present invention.

[Composition of orally-disintegrating solid preparation (900 mg)]

| | |
|---|---|
| mannitol-coated fine granules (Production Example 51) | 276.622 mg |
| mannitol-coated fine granules (Production Example 57) | 184.42 mg |
| outer layer component-granulated powder (Production Example 58) | 428.2 mg |
| flavor | 4.2 mg |
| magnesium stearate | 6.4 mg |
| total | 900 mg |

Example 20

Production of Orally-Disintegrating Solid Preparation

The polymer-coated fine granules (276.6 g) obtained in Production Example 51, the polymer-coated fine granules (184.4 g) obtained in Production Example 57, the outer layer component-granulated powder (525.9 g) obtained in Production Example 58, flavor (STRAWBERRY DURAROME, Nihon Firmenich K.K.) (5.3 g) and magnesium stearate (7.9 g) were mixed in a bag to give a mixed powder. The obtained mixed powder (1000 g) was tabletted using a rotary tabletting machine (Correct 19K AWC) (1000 mg/tablet, a 13 mm$\phi$ punch, flat-faced with beveled edge, tabletting pressure 13 kN) to give the orally-disintegrating solid preparation (1000 mg) containing compound X (60 mg) of the present invention.

[Composition of orally-disintegrating solid preparation (1000 mg)]

| | |
|---|---|
| mannitol-coated fine granules (Production Example 51) | 276.622 mg |
| mannitol-coated fine granules (Production Example 57) | 184.42 mg |
| outer layer component-granulated powder (Production Example 58) | 525.8 mg |
| flavor | 5.2 mg |
| magnesium stearate | 7.8 mg |
| total | 1000 mg |

Example 21

Production of Orally-Disintegrating Solid Preparation

The polymer-coated fine granules (276.6 g) obtained in Production Example 53, the polymer-coated fine granules (184.4 g) obtained in Production Example 57, the outer layer component-granulated powder (428.2 g) obtained in Production Example 58, flavor (STRAWBERRY DURAROME, Nihon Firmenich K.K.) (4.3 g) and magnesium stearate (6.4 g) were mixed in a bag to give a mixed powder. The obtained mixed powder (900 g) was tabletted using a rotary tabletting machine (Correct 19K AWC) (900 mg/tablet, a 13 mm$\phi$ punch, flat-faced with beveled edge, tabletting pressure 13 kN) to give the orally-disintegrating solid preparation (900 mg) containing compound X (60 mg) of the present invention.

[Composition of orally-disintegrating solid preparation (900 mg)]

| | |
|---|---|
| mannitol-coated fine granules (Production Example 53) | 276.622 mg |
| mannitol-coated fine granules (Production Example 57) | 184.42 mg |
| outer layer component-granulated powder (Production Example 58) | 428.2 mg |
| flavor | 4.2 mg |
| magnesium stearate | 6.4 mg |
| total | 900 mg |

Example 22

Production of Orally-Disintegrating Solid Preparation

The polymer-coated fine granules (276.6 g) obtained in Production Example 53, the polymer-coated fine granules (184.4 g) obtained in Production Example 57, the outer layer component-granulated powder (525.9 g) obtained in Production Example 58, flavor (STRAWBERRY DURAROME, Nihon Firmenich K.K.) (5.3 g) and magnesium stearate (7.9 g) were mixed in a bag to give a mixed powder. The obtained mixed powder (1000 g) was tabletted using a rotary tabletting machine (Correct 19K AWC) (1000 mg/tablet, a 13 mm$\phi$ punch, flat-faced with beveled edge, tabletting pressure 11 kN) to give the orally-disintegrating solid preparation (1000 mg) containing compound X (60 mg) of the present invention.

[Composition of orally-disintegrating solid preparation (1000 mg)]

| | |
|---|---|
| mannitol-coated fine granules (Production Example 53) | 276.622 mg |
| mannitol-coated fine granules (Production Example 57) | 184.42 mg |
| outer layer component-granulated powder (Production Example 58) | 525.8 mg |
| flavor | 5.2 mg |
| magnesium stearate | 7.8 mg |
| total | 1000 mg |

Production Example 59

Production of Fine Granules Coated with Intermediate Layer

The fine granules coated with pharmaceutically active ingredient obtained in Production Example 35 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 504 g) and mannitol (504 g) in purified water (5400 g), and dispersing titanium oxide (216 g), talc (216 g) and low-substituted hydroxypropyl cellulose (L-HPC-32, 360 g) in the obtained solution. A predetermined amount (6000 g) of the intermediate layer coating solution (7200 g) was applied to the fine granules coated with pharmaceutically active ingredient (2550 g), which were obtained in Production Example 35, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

[Composition of fine granules coated with intermediate layer (101.25 mg)]

| | |
|---|---|
| fine granules coated with pharmaceutically active ingredient (Production Example 35) | 63.75 mg |
| hypromellose | 10.5 mg |
| low-substituted hydroxypropyl cellulose | 7.5 mg |
| talc | 4.5 mg |
| titanium oxide | 4.5 mg |
| mannitol | 10.5 mg |
| total | 101.25 mg |

Production Example 60

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, and added to mixed dispersion (2430.5 g) of methacrylic acid-methyl acrylate-methyl methacrylate copolymer dispersion (Eudragit FS30D, manufactured by Evonik Roehm) (2309 g) and methacrylic acid-ethyl acrylate copolymer dispersion (Eudragit L30D-55, manufactured by Evonik Roehm) (121.5 g), and uniformly mixed to give a coating solution. A predetermined amount (3735 g) of the aforementioned coating solution (4270 g) was applied to the fine granules coated with intermediate layer (1215 g), which were obtained in Production Example 59, using a rotary fluidized bed coater (MP-10 TOKU-2 type, manufactured by POWREX CORPORATION). The coating conditions were: inlet air temperature about 40° C., product temperature about 26° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (160.575 mg)] | |
|---|---|
| fine granules coated with intermediate layer (Production Example 59) | 101.25 mg |
| methacrylic acid-methyl acrylate-methyl methacrylate copolymer | 48.09375 mg |
| methacrylic acid-ethyl acrylate copolymer | 2.53125 mg |
| polysorbate 80 | 1.0125 mg |
| glycerol monostearate | 2.53125 mg |
| triethyl citrate | 5.0625 mg |
| yellow ferric oxide | 0.046875 mg |
| ferric oxide | 0.046875 mg |
| total | 160.575 mg |

Production Example 61

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 60, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (168.075 mg)] | |
|---|---|
| polymer-coated fine granules (Production Example 60) | 160.575 mg |
| mannitol | 7.5 mg |
| total | 168.075 mg |

Production Example 62

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, and added to methacrylic acid-methyl acrylate-methyl methacrylate copolymer dispersion (Eudragit FS30D, manufactured by Evonik Roehm) (2430 g) and uniformly mixed to give a coating solution. A predetermined amount (3735 g) of the aforementioned coating solution (4270 g) was applied to the fine granules coated with intermediate layer (1215 g), which were obtained in Production Example 59, using a rotary fluidized bed coater (MP-10 TOKU-2 type, manufactured by POWREX CORPORATION). The coating conditions were: inlet air temperature about 40° C., product temperature about 26° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (160.575 mg)] | |
|---|---|
| fine granules coated with intermediate layer (Production Example 59) | 101.25 mg |
| methacrylic acid-methyl acrylate-methyl methacrylate copolymer | 50.625 mg |
| polysorbate 80 | 1.0125 mg |
| glycerol monostearate | 2.53125 mg |
| triethyl citrate | 5.0625 mg |
| yellow ferric oxide | 0.046875 mg |
| ferric oxide | 0.046875 mg |
| total | 160.575 mg |

Production Example 63

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 62, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (168.075 mg)] | |
|---|---|
| polymer-coated fine granules (Production Example 62) | 160.575 mg |
| mannitol | 7.5 mg |
| total | 168.075 mg |

Production Example 64

Production of Fine Granules Coated with Intermediate Layer

The fine granules coated with pharmaceutically active ingredient obtained in Production Example 42 was coated with an intermediate layer coating solution using a rotary fluidized bed coater (MP-10 TOKU-2 type, manufactured by POWREX CORPORATION), and directly dried to give fine granules with the following composition. The intermediate layer coating solution was produced by dissolving hypromellose (TC-5E, 504 g) and mannitol (504 g) in purified water (5400 g), and dispersing titanium oxide (216 g), talc (216 g) and low-substituted hydroxypropyl cellulose (L-HPC-32, 360 g) in the obtained solution. A predetermined amount (6000 g) of the intermediate layer coating solution (7200 g) was applied to the fine granules coated with pharmaceutically active ingredient (2550 g), which were obtained in Production Example 42, using a rotary fluidized bed coater (MP-10 TOKU-2 type, manufactured by POWREX CORPORATION). The coating conditions were: inlet air temperature about 70° C., product temperature about 41° C., spray air volume about 100 NL/min, rotor speed about 550 rpm, spray rate about 16 g/min, spray gun position tangential. After the completion of coating, the obtained fine granules were dried for about 40 min and passed through a round sieve to give fine granules coated with intermediate layer with a particle size of 150 μm-355 μm.

| [Composition of fine granules coated with intermediate layer (67.5 mg)] | |
|---|---|
| fine granules coated with pharmaceutically active ingredient (Production Example 42) | 42.5 mg |
| hypromellose | 7 mg |
| low-substituted hydroxypropyl cellulose | 5 mg |
| talc | 3 mg |
| titanium oxide | 3 mg |
| mannitol | 7 mg |
| total | 67.5 mg |

Production Example 65

Production of Polymer-Coated Fine Granules

Purified water (1714.4 g) was heated to 80° C., and polysorbate 80 (14.58 g), glycerol monostearate (36.45 g), triethyl citrate (72.9 g), yellow ferric oxide (0.675 g) and ferric oxide (0.675 g) were dispersed therein. The suspension was cooled to room temperature, and added to mixed dispersion (2430.5 g) of methacrylic acid-methyl acrylate-methyl methacrylate copolymer dispersion (Eudragit FS30D, manufactured by Evonik Roehm) (2309 g) and methacrylic acid-ethyl acrylate copolymer dispersion (Eudragit L30D-55, manufactured by Evonik Roehm) (121.5 g), and uniformly mixed to give a coating solution. A predetermined amount (3735 g) of the aforementioned coating solution (4270 g) was applied to the fine granules coated with intermediate layer (1215 g), which were obtained in Production Example 64, using a rotary fluidized bed coater (MP-10 TOKU-2 type, manufactured by POWREX CORPORATION). The coating conditions were: inlet air temperature about 40° C., product temperature about 26° C., spray air volume about 120 NL/min, rotor speed about 550 rpm, spray rate about 7 g/min, spray gun position tangential. After the completion of coating, polymer-coated fine granules (1927 g) were obtained.

| [Composition of polymer-coated fine granules (107.05 mg)] | |
|---|---|
| fine granules coated with intermediate layer (Production Example 64) | 67.5 mg |
| methacrylic acid-methyl acrylate-methyl methacrylate copolymer | 28.6875 mg |
| methacrylic acid-ethyl acrylate copolymer | 5.0625 mg |
| polysorbate 80 | 0.675 mg |
| glycerol monostearate | 1.6875 mg |
| triethyl citrate | 3.375 mg |
| yellow ferric oxide | 0.03125 mg |
| ferric oxide | 0.03125 mg |
| total | 107.05 mg |

Production Example 66

Production of Mannitol-Coated Fine Granules

Mannitol (150 g) was dissolved in purified water (900 g) to give a coating solution. A predetermined amount (630 g) of the aforementioned coating solution (1050 g) was applied to the polymer-coated fine granules (1927 g), which were obtained in Production Example 65, using a rotary fluidized bed coater (MP-10 TOKU-2 type, manufactured by POWREX CORPORATION). The coating conditions were: inlet air temperature about 60° C., product temperature about 34° C., spray air volume about 120 NL/min, rotor speed about 550 rpm, spray rate about 10 g/min, spray gun position tangential. After the completion of coating, the obtained fine granules were dried for about 40 min and passed through a round sieve to give mannitol-coated fine granules with a particle size of 250 μm-425 μm.

| [Composition of mannitol-coated fine granules (112.05 mg)] | |
|---|---|
| polymer-coated fine granules (Production Example 65) | 107.05 mg |
| mannitol | 5 mg |
| total | 112.05 mg |

Example 23

Production of Orally-Disintegrating Solid Preparation

The mannitol-coated fine granules (1345 g) obtained in Production Example 61, the mannitol-coated fine granules (896.4 g) obtained in Production Example 66, the outer layer component-granulated powder (2418 g) obtained in Production Example 47, sucralose (76.8 g), flavor (STRAWBERRY DURAROME, Nihon Firmenich K.K.) (25.6 g) and magnesium stearate (38.4 g) were mixed using a tumbling mixer to give a mixed powder. The obtained mixed powder (4800 g) was tabletted using a rotary tabletting machine (AQUARIUS, manufactured by Kikusui Seisakusho Ltd.) (600 mg/tablet, a 12 mmφ punch, flat-faced with beveled edge, tabletting pressure 12.5 kN) to give the orally-disintegrating solid preparation (600 mg) containing compound X (30 mg) of the present invention.

| [Composition of orally-disintegrating solid preparation (600 mg)] | |
| --- | --- |
| mannitol-coated fine granules (Production Example 61) | 168.075 mg |
| mannitol-coated fine granules (Production Example 66) | 112.05 mg |
| outer layer component-granulated powder (Production Example 47) | 302.275 mg |
| sucralose | 9.6 mg |
| flavor | 3.2 mg |
| magnesium stearate | 4.8 mg |
| total | 600 mg |

Example 24

Production of Orally-Disintegrating Solid Preparation

The mannitol-coated fine granules (1345 g) obtained in Production Example 63, the mannitol-coated fine granules (896.4 g) obtained in Production Example 66, the outer layer component-granulated powder (2418 g) obtained in Production Example 47, sucralose (76.8 g), flavor (STRAWBERRY DURAROME, Nihon Firmenich K.K.) (25.6 g) and magnesium stearate (38.4 g) were mixed using a tumbling mixer to give a mixed powder. The obtained mixed powder (4800 g) was tabletted using a rotary tabletting machine (AQUARIUS, manufactured by Kikusui Seisakusho Ltd.) (600 mg/tablet, a 12 mmϕ punch, flat-faced with beveled edge, tabletting pressure 12.5 kN) to give the orally-disintegrating solid preparation (600 mg) containing compound X (30 mg) of the present invention.

| [Composition of orally-disintegrating solid preparation (600 mg)] | |
| --- | --- |
| mannitol-coated fine granules (Production Example 63) | 168.075 mg |
| mannitol-coated fine granules (Production Example 66) | 112.05 mg |
| outer layer component-granulated powder (Production Example 47) | 302.275 mg |
| sucralose | 9.6 mg |
| flavor | 3.2 mg |
| magnesium stearate | 4.8 mg |
| total | 600 mg |

INDUSTRIAL APPLICABILITY

The orally-disintegrating solid preparation of the present invention comprising fine granules comprising a pharmaceutically active ingredient, particularly, a pharmaceutically active ingredient unstable to acid, the release of the pharmaceutically active ingredient in the presence of acid, for example, in the stomach, can be improved to achieve a desired elution profile. In addition, variation of elution profiles for preparations or lots (elution variation) can also be improved. Since the preparation can control release of the pharmaceutically active ingredient for a long time, a therapeutically effective concentration can be maintained for a prolonged time, administration frequency can be reduced, an effective treatment with a small dose can be realized, and effects such as reduction of side effects caused by slow rise of blood concentration and the like can be achieved. Since the preparation shows superior disintegration property or dissolution property in the oral cavity, it is used for the treatment or prophylaxis of various diseases as a preparation conveniently taken by elderly persons and children even without water. In addition, since the fine granules comprising the pharmaceutically active ingredient having a size preventing dusty texture are blended, a preparation smooth in the mouth and comfortable during use can be provided.

This application is based on application Nos. 2008-061673 (filed on Mar. 11, 2008) and 2008-334920 (filed on Dec. 26, 2008) filed in Japan, the contents of which are incorporated hereinto by reference.

The invention claimed is:

1. An orally-disintegrating solid preparation comprising:
(1) fine granules A, comprising core granules comprising R-lansoprazole or a salt thereof as a pharmaceutically active ingredient; an intermediate coating layer on the core granules, the intermediate layer comprising at least one selected from the group consisting of low-substituted hydroxypropyl cellulose, hydroxypropyl cellulose, hypromellose, polyvinylpyrrolidone, polyvinyl alcohol, methylcellulose and hydroxyethylmethylcellulose, the fine granules A comprising the intermediate coating layer in an amount of 0.02 part by weight-1.5 part by weight per 1 part by weight of the core granules; and a controlled release film over the intermediate coating layer, wherein the controlled release film comprises a methacrylic acid-methyl acrylate-methyl methacrylate copolymer capable of affording a casting film having an elongation at break of 100%-700%,
wherein the amount of the pharmaceutically active ingredient dissolved from the fine granules A is not more than 10% in 2 hours as expressed by the dissolution rate in a pH 1.2 solution, and not more than 5% in 1 hour as expressed by the dissolution rate in a pH 6.8 solution, and
wherein the fine granules have an average particle size of 500 μm or below; and
(2) fine granules B comprising the same pharmaceutically active ingredient with a different release rate relative to the fine granules A,
wherein the fine granules B are enteric fine granules coated with a coating layer comprising an enteric polymer that is soluble at pH less than 6.0, but not at pH less than 5.0,
wherein the enteric coating layer comprises an aqueous enteric polymer base and a sustained-release substrate,
wherein the aqueous enteric polymer base is at least one selected from the group consisting of, methacrylic acid ethyl acrylate copolymer, hydroxypropyl methylcellulose acetate succinate and carboxymethyl ethyl cellulose, and the sustained-release substrate is at least one selected from the group consisting of methyl methacrylate-ethyl acrylate copolymer and ethylcellulose,
wherein the preparation is in the form of a tablet.

2. The preparation of claim 1, wherein the fine granules B have an average particle size of 500 μm or below.

3. The preparation of claim 1, wherein the fine granules A and the fine granules B comprise the pharmaceutically active ingredient at a weight ratio of 1:10-10:1.

4. The preparation of claim 1, further comprising an additive.

5. The preparation of claim 4, wherein the additive comprises a water-soluble sugar alcohol.

6. The preparation of claim 4, wherein the additive comprises a disintegrant.

7. The preparation of claim 4, comprising
10-50 wt % fine granules A,
10-30 wt % fine granules B, and
20-80 wt % additive.

8. The preparation of claim 1, wherein the total weight of the preparation is 1000 mg or below.

9. The preparation of claim 1, wherein the oral disintegration time is 90 seconds or less.

10. The preparation of claim 1, which is capable of achieving an average pH in the stomach of not less than 4 at 0.5 hours after oral administration and maintaining said pH or higher pH for 14 hours or longer.

11. The preparation of claim 1, wherein the pharmaceutically active ingredient is R-lansoprazole or a salt thereof, which reaches the maximum blood drug concentration in 5 hours and maintains the maximum blood drug concentration of not less than 100 ng/mL for 4 hours or longer, when 30 mg of the pharmaceutically active ingredient is administered orally.

* * * * *